(12) United States Patent
Townsend et al.

(10) Patent No.: US 10,765,616 B2
(45) Date of Patent: Sep. 8, 2020

(54) ORAL FORMULATION OF POLYGLUCOSAMINE DERIVATIVES IN COMBINATION WITH A NON-FERMENTABLE SUGAR

(71) Applicant: SYNEDGEN, INC., Claremont, CA (US)

(72) Inventors: Stacy M. Townsend, Rancho Cucamonga, CA (US); Shenda M. Baker, Upland, CA (US); William P. Wiesmann, Chevy Chase, MD (US)

(73) Assignee: SYNEDGEN, INC., Claremont, CA (US)

( * ) Notice: Subject to any disclaimer, the term of this patent is extended or adjusted under 35 U.S.C. 154(b) by 0 days.

(21) Appl. No.: 15/948,446

(22) Filed: Apr. 9, 2018

(65) Prior Publication Data

US 2018/0289609 A1     Oct. 11, 2018

Related U.S. Application Data

(63) Continuation of application No. 14/775,679, filed as application No. PCT/US2014/024864 on Mar. 12, 2014.

(60) Provisional application No. 61/778,077, filed on Mar. 12, 2013.

(51) Int. Cl.
| | |
|---|---|
| *A61K 8/73* | (2006.01) |
| *A61K 8/49* | (2006.01) |
| *A61K 8/92* | (2006.01) |
| *A61K 8/368* | (2006.01) |
| *A61Q 17/00* | (2006.01) |
| *A61C 17/20* | (2006.01) |
| *A61K 31/155* | (2006.01) |
| *A61K 31/4164* | (2006.01) |
| *A61K 31/726* | (2006.01) |
| *A61K 8/34* | (2006.01) |
| *A61K 31/047* | (2006.01) |
| *A61K 31/722* | (2006.01) |
| *A61K 45/06* | (2006.01) |
| *A61Q 11/00* | (2006.01) |

(52) U.S. Cl.
CPC ............ *A61K 8/736* (2013.01); *A61C 17/20* (2013.01); *A61K 8/345* (2013.01); *A61K 8/368* (2013.01); *A61K 8/4993* (2013.01); *A61K 8/922* (2013.01); *A61K 31/047* (2013.01); *A61K 31/155* (2013.01); *A61K 31/4164* (2013.01); *A61K 31/722* (2013.01); *A61K 31/726* (2013.01); *A61K 45/06* (2013.01); *A61Q 11/00* (2013.01); *A61Q 17/005* (2013.01)

(58) Field of Classification Search
CPC ...... A61K 8/736; A61K 8/345; A61K 31/722; A61K 31/047; A61K 31/726; A61K 31/155; A61Q 17/005; A61Q 11/00

USPC .......................................................... 514/54
See application file for complete search history.

(56) References Cited

U.S. PATENT DOCUMENTS

| | | | |
|---|---|---|---|
| 4,229,430 A | 10/1980 | Fahim et al. | |
| 4,512,968 A | 4/1985 | Komiyama et al. | |
| 5,541,165 A * | 7/1996 | Turgeon | A61K 36/48 424/49 |
| 6,723,305 B2 | 4/2004 | DePierro et al. | |
| 8,119,780 B2 | 2/2012 | Baker et al. | |
| 8,399,635 B2 | 3/2013 | Baker et al. | |
| 8,658,775 B2 | 2/2014 | Baker et al. | |
| 8,916,542 B2 | 12/2014 | Baker et al. | |
| 9,012,429 B2 | 4/2015 | Baker et al. | |
| 9,029,351 B2 | 5/2015 | Baker et al. | |
| 9,234,050 B2 | 1/2016 | Baker et al. | |
| 9,439,925 B2 | 9/2016 | Baker et al. | |
| 9,732,164 B2 | 8/2017 | Baker et al. | |
| 2004/0103821 A1 | 6/2004 | Shobu et al. | |
| 2004/0151774 A1* | 8/2004 | Pauletti | A61K 9/0034 424/486 |
| 2005/0084551 A1 | 4/2005 | Jensen et al. | |
| 2005/0163727 A1 | 7/2005 | Doyle et al. | |
| 2006/0286044 A1 | 12/2006 | Robinson et al. | |
| 2007/0281904 A1 | 12/2007 | Baker et al. | |
| 2008/0024794 A1 | 1/2008 | Miyazaki et al. | |
| 2008/0248508 A1 | 10/2008 | Baker et al. | |
| 2010/0056474 A1 | 3/2010 | Baker et al. | |
| 2010/0130443 A1* | 5/2010 | Baker | A61K 31/722 514/55 |
| 2010/0286080 A1 | 11/2010 | Badwan et al. | |
| 2012/0295355 A1 | 11/2012 | Baker et al. | |
| 2012/0301408 A1 | 11/2012 | Baker et al. | |
| 2012/0329751 A1 | 12/2012 | Baker et al. | |
| 2014/0080785 A1 | 3/2014 | Baker et al. | |

(Continued)

FOREIGN PATENT DOCUMENTS

| | | | | |
|---|---|---|---|---|
| JP | 2007314505 A | | 12/2007 | |
| NL | 9301837 | * | 5/1995 | ............. A61K 8/345 |

(Continued)

OTHER PUBLICATIONS

Aksoy et al, Archives of Oral Biology, 2006, 51, 476-481.*

(Continued)

Primary Examiner — Ganapathy Krishnan
(74) Attorney, Agent, or Firm — Goodwin Procter LLP

(57) ABSTRACT

Described herein are methods and compositions that contain a soluble polyglucosamine or polyglucosamine derivative for use in oral health. The compositions are useful for, e.g., reducing bacteria (e.g., by clumping and removing) or disrupting a biofilm in the mouth of a subject, reducing dry mouth, and reducing oral inflammation.

4 Claims, 20 Drawing Sheets

(56) References Cited

U.S. PATENT DOCUMENTS

| | | |
|---|---|---|
| 2014/0221308 A1 | 8/2014 | Baker et al. |
| 2015/0031610 A1 | 1/2015 | Baker et al. |
| 2015/0224044 A1 | 8/2015 | Baker et al. |
| 2016/0022564 A1 | 1/2016 | Townsend et al. |
| 2016/0022730 A1 | 1/2016 | Baker et al. |
| 2017/0119810 A1 | 5/2017 | Baker et al. |
| 2017/0136056 A1 | 5/2017 | Baker et al. |

FOREIGN PATENT DOCUMENTS

| | | |
|---|---|---|
| NL | 9301837 A | 5/1995 |
| WO | WO-2006005211 A1 | 1/2006 |
| WO | WO-2008063503 A2 | 5/2008 |
| WO | WO-2010081204 A2 | 7/2010 |
| WO | WO-2011127144 A1 | 10/2011 |

OTHER PUBLICATIONS

Addy, M., "Chlorhexidine compared with other locally delivered antimicrobials", J Clin Periodontol 13: 957-964. (1986).

Arslan, SY., et al., "The Effect of Lactoferrin on Oral Bacterial Attachment", Oral Microbio Immunol, 24: pp. 411-416, (2009).

Beenken, K.E., Blevins, J.S., and Smeltzer, M.S. (2003) Mutation of sarA in *Staphylococcus aureus* limits biofilm formation. Infect Immun 71 :4206-4211.

Charles, C., Mostler, K., Bartels, L., and Mankodi, S. (2004) Comparative antiplaque and antigingivits effectiveness of a chlorhexidine and an essential oil mouthrinse: 6-month clinical trial. J Clin Periodontol 31 :878-884.

Corbin, A., Pitts, B., Parker, A., and Stewart, P.S. (2011) Antimicrobial penetration and efficacy in an in vitro oral biofilm model. Antimicrob Agents Chemother. 55(7):3338-3344.

Costa, E.M., et al., "Evaluation and insights into chitosan antimicrobial activity against anaerobic oral pathogens", Anaerobe 18:305-309. (2012).

Costerton, J.W., Stewart, P.S., and Greenberg, E.P. (1999) Bacterial biofilms: a common cause of persistent infections. Science 284:1318-1322.

Database GNPD [Online] MINTEL; Jun. 2000 (Jun. 2000), Optima Healthcare: "Aloe Toothpaste Range", XP002742494, Database accession No. 26767 *Product Description and ingredients*.

Decker et al., "Effect of Xylitol/Chlorhexidine Versus Xylitol or Chlorhexidine as Single Rinses on Initial Biofilm Formation of Cariogenic Streptococci", Quintessence International, vol. 39, No. 7, (2008).

Eick et al., "Efficacy of Chlorhexidine Digluconate—Containing Formulations and other Mouthrinses Against Periodontopathogenic Microorganisms", Quintessence International, vol. 42, No. 8, (2011).

Eley, "Antibacterial agents in the control of supragingival plaque—a review" British Dental Journal, vol. 186, No. 6, Mar. 27, 1999.

Ernst, et al., "Clinical Study on the Effectiveness and Side Effects of Hexetidine and Chlorhexidine Mouthrinses Versus a Negative Control", Quintessence International, vol. 36, No. 8, (2005).

Extended European Search Report from Corresponding EP10814537.6 dated Aug. 24, 2015.

Fan, A., Turro, N.J., and Somasundaran, P. (2000) A study of duel polymer flocculation. Colloids and Surfaces A: Physicochem Eng Aspects 162:141-148.

Gale, K., "Soluble Chitosan Derivatives Control Oral Biofilms", Reuters Health [URL accessed at: http://www.drbicuspid.com/index.aspx?sec=sup&sub=hyg&pag-dis&ItemID-304765 on Sep 4, 2012], (2010).

Gibson, F.C., Hong, C., Chou, H-H., et al. (2004) Innate immune recognition of invasive bacteria accelerates atherosclerosis in apolipoprotein E-deficient mice. Circulation 109:2801-2806.

Giertsen, "Effects of Mouthrinses with Triclosan, Zinc Ions, Copolymer, and Soduim Lauryl Sulphate Combined with Flouride on Acid Formation be Dental Plaque in vivo", Caries Res, pp. 430-435, vol. 38, 2004.

Hanning et al., Influence of a mouthwash containing hydroxyapatite microclusters on bacterial adherence in situ, Clin Oral Invest, 2012.

Harrison, J.J., Turner, R.J., and Geri, H. (2005) High-throughput metal susceptibility testing of microbial biofilms. Environ Microbiol 7 :981-994.

Hashibe, M., Brennan, P., Benhamou, S., et al. (2007) Alcohol drinking in never users of tobacco, cigarette smoking in never drinkers, and the risk of head and neck cancer: pooled analysis in the International Head and Neck Cancer Epidemiology Consortium. J Natl Cancer Inst 99(10):777-789.

Hayashi, Y. et al., "Chewing chitosan-containing gum effectively inhibits the growth of cariogenic bacteria", J Arch Oral Bio 52:290-294. (2006).

Howlader, N., Noone, A.M., Krapcho, M., et al. SEER Cancer Statistics Review, 1975-2009 (Vintage 2009 Populations), National Cancer Institute. Bethesda, MD.

Ikinci, G., Senel, S., Akincibay, H., et al. (2002) Effect of chitosan on a periodontal pathogen Porphyromonas gingivalis. Int J Pharm 235:121-127.

International Search Report and Written Opinion for International Application No. PCTUS14/24864 dated Nov. 5, 2014.

International Search Report and Written Opinion for International Application No. PCTUS2010/047759 dated Oct. 28, 2010.

Jackson, L.A., "The science and technology of industrial water treatment", CRC Press pp. 465- 479. (2010).

Jae-Young Je et al: "Chitosan Derivatives Killed Bacteria by Disrupting the Outer and Inner Membrane", Journal of Agricultural and Food Chemistry, vol. 54, No. 18, Sep. 1, 2006 {Sep. 1, 2006 ), pp. 6629-6633, XP055203350, US ISSN: 0021-8561, DOI: 10.1021/jf061310p *abstract*.

Ji, Q.X., et al., "In vitro evaluation of the biomedical properties of chitosan and quaternized chitosan for dental applications", Carbohydr Res 344:1297-1302. (2009).

Laskey, Jen, A Guide to Nighttime Oral Care. Sep. 3, 2007. <http://www.everydayhealth.com/dental-health/nighttime-oralcare/guide-to-nighttime-oral-health.aspx>.

Leung, K.P. et al., "Control of oral biofilm formation by an antimicrobial decapeptide", J Den Res 84(12): 1172-1177. (2005).

Loesche, W.J. {1986). Role of *Streptococcus mutans* in Human Dental Decay. Micro Rev 50(4): 353-380.

Malhorta et al., "Comparative in Vitro Evaluation of Efficacy of Mouthrinses Against *Streptococcus mutans*, Lactobacilli and Candida albicans", Oral Health Prey Dent, vol. 9, No. 3, pp. 261-268, (2011).

Mandel, "Antimicrobial Mouthrinses: Overview and Update", J Am Dent Assoc, vol. 125, pp. 2S-10S, (1994).

Mandel, "Chemotherapeutic Agents for Controlling Plaque and Gingivitis", J Clin Periodontal, vol. 15, pp. 488-498, (1988).

Mealey, "Periodontal disease and diabetes: A two-way street", JADA, vol. 137, p. 26S-31S, 2006.

Menendez, A., Li, F., Michalek, S.M., et al. (2005) Comparative analysis of the antibacterial effects of combined mouthrinses on *Streptococcus mutans*. Oral Microbiol Immunol 20:31-34.

National Institute of Dental and Craniofacial Research, Bethesda, MD. Periodontal Diseases (2010) [URL accessed at http://http://report.nih.gov/NI HfactsheetsNiewFactSheet.aspx?csid=111&key=P#P on Oct. 1, 2012].

Pan, P.C., Harper, S., Ricci-Nittel, D., Lux, R., and Shi, W. (2010) In-vitro evidence for efficacy of antimicrobial mouthrinses. J Dent 38 Suppl 1 :S16-20.

Periodontal Disease in Adults (Age 20 to 64) US NIDCR, 2006.

Ramsey and Whiteley, "Polymicrobial interactions stimulate resistance to host innate immunity through metabolite perception", PNAS, vol. 106, No. 5, pp. 1578-1583, 2009.

Romero, et al. "Relationship Between Periodontal Disease in Pregnant Women and the Nutritional Condition of their Newborns", J Periodontol, pp. 1177-1183, vol. 73, No. 10, 2002.

Santos A. {2003) Evidence-based control of plaque and gingivitis. J Clin Periodontol 30:13-16.

Shanmugham , J.R., Zavras, A.I., Rosner, B.A., and Giovannucci, E.L. (2010) Alcohol-folate interactions in the risk of oral cancer in women: a prospective cohort study. Cancer Epidemiol Biomarkers Prey 19(10): 2516-2524.

(56) References Cited

OTHER PUBLICATIONS

Sreenivasan, P. et al., "Anti plaque biocides and bacterial resistance: a review", J Clin Periodontol 29(11):965-974. (2002).
Tang, et al., "Antibacterial Action of a Novel Functionalized Chitosan-Arginine Against Gram-Negative Bacteria", Acta Biomater, 6(7), pp. 2562-2571, (2010).
Written Opinion for International Application No. PCTUS1424864 dated Nov. 5, 2014.
Xavier, J.B., Picioreanu, C., Rani, S.A., van Loosdrecht M.C.M., and Stewart, P.S. (2005) Biofilm-control strategies based on enzymic disruption of the extracellular polymeric substance matrix—a modeling study. Microbiology 151 :3817-3832.
Zheng et al., "Effects of Chlorhexidine, Listerine, and Fluoride Listerine Mouthrinses on Four Putative Root-caries Pathogens in the Biofilm", Chin J Dent Res vol. 14, No. 2, pp. 135-140, (2011).
Sano et al, "Effect of chitosan rinsing on reduction of dental plaque formation," Bull Tokyo Dent Coll, 2003, vol. 44, No. 1, pp. 9-16.
Merck Manual 18th Edition, Japanese Edition, first print, Apr. 25, 2007, third issue, pp. 850-851 and 891-895.
Iwano et al, "Relationship between periodontitis and dental caries," Medical Online, 2008, vol. 50, pp. 132.

\* cited by examiner

ORAL FORMULATION OF POLYGLUCOSAMINE DERIVATIVES IN COMBINATION WITH A NON-FERMENTABLE SUGAR

RELATED APPLICATIONS

This application is a continuation application of U.S. non-provisional application Ser. No. 14/775,679, filed Sep. 12, 2015, which is a U.S. national phase application under 35 U.S.C. § 371 of International Application No. PCT/US2014/024864, filed Mar. 12, 2014, which claims priority under 35 U.S.C. § 119(e) to U.S. provisional patent application No. 61/778,077, filed Mar. 12, 2013, the contents of each of which is incorporated herein by reference.

BACKGROUND OF INVENTION

Oral disease is a serious public health concern due to its significant impact on overall general health and its chronic nature. In the United States, about 4 out of five people suffer from gum disease, and about a fifth of the population has periodontitis (US NIDCR, 2006). Periodontal disease is an infectious disease caused by oral biofilms that are often resistant to treatment, contributing to the chronic nature that can be associated with oral disease. Specifically, periodontal disease is a known risk factor for diabetes (Mealey, 2006), premature or low birth weight in neonates (Romero et al., 2002), and lung and heart disease (Costerton, et al., 1999; Gibson, et al., 2011). Mechanical oral hygiene methods for plaque removal alone do not sufficiently control biofilm accumulation. Further, poor oral hygiene practices in general contribute to poor disease outcome. Numerous studies support the use of an oral rinse for plaque control in addition to mechanical hygiene methods (i.e., toothbrushing), and have shown various degrees of effectiveness dependent on the active ingredients (Decker et al., 2008; Eick et al., 2011; Giertsen, 2004; Hanning et al., 2012; Malhotra et al., 2011; Menendez et al., 2005; Zheng and Wang, 2011). Poor salivary flow leading to xerostomia (i.e., dry mouth) can also lead to poor oral clearance of plaque and excessive cavities. An oral rinse treatment that facilitates the removal of oral biofilms and is well tolerated by sensitive mucosal tissues with minimal side effects would increase patient compliance and support oral health.

Oral bacteria, such as *Streptococcus mutans*, produce extracellular glucans that facilitate bacterial adhesion to the surface of the tooth. This initial adhesion supports persistent colonization in a nutrient-rich environment (the oral cavity) and facilitates the development of biofilms, which can make treatment more difficult because biofilms are more resistant to antimicrobial agents, biocides, and the host immune response (Loesche, et al., 1986). Biofilms in the mouth are called plaque. Calculus or tartar is a form of hardened dental plaque that is caused by the continual accumulation of minerals from saliva on plaque on the teeth. Oral rinse treatments targeted to remove biofilms may have a greater overall positive impact on the maintenance of good oral hygiene to prevent periodontal disease and associated general health concerns (Costerton, 1999; Ramsey and Whiteley, 2009). Additionally, disagreeable side effects of some products currently in use are: tooth, tongue and restoration discoloration, burning sensation, irritation of mucosal tissue, disturbance of taste, and potentially increased supra-gingival calculus build-up (Charles, et al., 2004; Eley, 1999; Ernst, et al., 2005; Mandel, 1988; Mandel, 1994; Santos, 2003). These undesirable side effects significantly impact patient compliance that may limit the effectiveness of treatment. There remains a need for a safe, well tolerated, and practical aid to reduce the formation of and to remove oral biofilms.

Oral formulations, or mouthwashes or mouth rinses, are often recommended and routinely used by consumers as part of their oral care hygiene regimens. The benefits include control of plaque and calculus formation, removal and prevention of stains, tooth whitening, breath freshening, and overall improvements in mouth feel, impression and aesthetics. Therapeutic benefits include caries prevention through the use of fluoride salts and gingivitis prevention by the use of antimicrobial agents. Other therapeutic benefits of oral rinses include prevention or treatment of infection. Poly (acetyl, arginyl) glucosamine (PAAG) is a novel polycationic biopolymer with unique properties to facilitate the removal of oral biofilms while limiting imbalance of the oral flora and damage to oral mucosa (by current therapies having known cytotoxic ingredients (Baker et al., 2007)). The mechanism of action of PAAG is thought to be similar to other polycationic polymers that work by binding the bacterial cell membrane and disrupting biofilm extracellular polymeric substance (EPS) matrix through interactions with negatively charged phospholipids and structural polymers. PAAG has been shown to rapidly aggregate bacteria. Further, the positive charge allows the PAAG oral rinse formulation to be soluble and active at pH 7, reducing possible irritation and enamel etching, which may be caused by other acidic oral products.

The present invention relates to an oral formulation of PAAG that, alone or in combination with a non-fermentable sugar (e.g., a plurality of non-fermentable sugars), and other inactive ingredients, improves efficacy in prevention of plaque formation and improved plaque and bacterial removal. Surprisingly, when used in combination with a non-fermentable sugar, lower concentrations of PAAG may be used (relative to a formulation without a non-fermentable sugar) to reach a therapeutically effective amount. Therapeutic formulations (e.g., of PAAG, alone or in combination with a non-fermentable sugar (e.g., a plurality of non-fermentable sugars)) may prevent and treat gingivitis, periodontitis, xerostomia and other oral diseases, including infection and from complications after tooth extraction or oral surgery. In addition, the formulation may be effective for the treatment and prophylaxis of mucositis and stomatitis of the oral cavity.

SUMMARY OF INVENTION

Oral care compositions comprising a derivatized polyglucosamine and a non-fermentable sugar (e.g., a plurality of non-fermentable sugars) are described herein. Exemplary methods using the compositions described herein include methods of treating or preventing oral disease or a symptom of an oral disease, removing plaque, treating or preventing inflammation (e.g., gingivitis or periodontitis), treating or preventing halitosis, disrupting or reducing the viscosity of or dissolving a preformed biofilm in the mouth, treating dry mouth conditions and restricting the growth of biofilms or plaque in the mouth. In some embodiments, a composition described herein can be used to treat or prevent a disorder (e.g., a disorder in the mouth of a subject).

In one aspect, the invention features an oral care composition comprising a non-fermentable sugar (e.g., sorbitol, xylitol) and a poly (acetyl, arginyl) glucosamine (PAAG), wherein the molecular weight of the PAAG is from 20 to 200 kDa.

In some embodiments, the composition further comprises a thickener (e.g., glycerin, glycerol), a surfactant (e.g., Polysorbate 20), a flavoring agent, or a preservative (e.g., benzoic acid). In some embodiments, the composition further comprises at least two of the following: a thickener (e.g., glycerin), a surfactant (e.g., Polysorbate 20), a flavoring agent, and a preservative (e.g., benzoic acid). In some embodiments, the composition further comprises at least three of the following: a thickener (e.g., glycerin), a surfactant (e.g., Polysorbate 20), a flavoring agent, and a preservative (e.g., benzoic acid). In some embodiments, the composition further comprises all of the following: a thickener (e.g., glycerin), a surfactant (e.g., Polysorbate 20), a flavoring agent, and a preservative (e.g., benzoic acid).

In some embodiments, the non-fermentable sugar comprises a plurality of non-fermentable sugars. In some aspects of these embodiments, the non-fermentable sugars are selected from a group consisting of sorbitol, xylitol, mannitol, glycerin, and erythritol. In some aspects of these embodiments, the non-fermentable sugars and PAAG are present in the composition at an amount of about 15% to about 70% w/v.

In some embodiments, the PAAG is present in the composition at an amount of at least 0.003% w/v of PAAG. In some aspects of these embodiments, the PAAG is present in the composition at an amount of at least 0.003% to about 0.05% w/v of PAAG. In some aspects of these embodiments, the PAAG is present in the composition at an amount of at least 0.003% to about 0.02% w/v of PAAG. In some aspects of these embodiments, the PAAG is present in the composition at an amount of at least 0.003% to about 0.01% w/v of PAAG. In some embodiments, the PAAG is present in the composition at an amount of at least 0.004% w/v of PAAG. In some aspects of these embodiments, the PAAG is present in the composition at an amount of at least 0.004% to about 0.05% w/v of PAAG. In some aspects of these embodiments, the PAAG is present in the composition at an amount of at least 0.004% to about 0.02% w/v of PAAG. In some aspects of these embodiments, the PAAG is present in the composition at an amount of at least 0.01% w/v of PAAG. In some aspects of these embodiments, the PAAG is present in the composition at an amount of at least 0.01% to about 0.05% w/v of PAAG. In some aspects of these embodiments, the PAAG is present in the composition at an amount of at least 0.01% to about 0.02% w/v of PAAG.

In some embodiments, the non-fermentable sugars are present in the composition at about 5% to about 65% w/v (e.g., about 10% to about 65% w/v, about 17% to about 65% w/v) and PAAG is present in the composition at at least 0.003% w/v. In some embodiments, the non-fermentable sugars are present in the composition at about 5% to about 65% w/v (e.g., about 10% to about 65% w/v, about 17% to about 65% w/v) and PAAG is present in the composition at at least 0.004% w/v. In some embodiments, the non-fermentable sugars are present in the composition at about 5% to about 65% w/v (e.g., about 10% to about 65% w/v, about 17% to about 65% w/v) and PAAG is present in the composition at about 0.003% w/v. In some embodiments, the non-fermentable sugars are present in the composition at about 5% to about 65% w/v (e.g., about 10% to about 65% w/v, about 17% to about 65% w/v) and PAAG is present in the composition at about 0.004% w/v. In some embodiments, the non-fermentable sugars are present in the composition at about 5% to about 65% w/v (e.g., about 10% to about 65% w/v, about 17% to about 65% w/v) and PAAG is present in the composition at about 0.015% to about 0.20% w/v (e.g., about 0.018% w/v). In some aspects of these embodiments, the amount of PAAG present in the composition is reduced relative to a composition without non-fermentable sugars. In some aspects of these embodiments, one of the non-fermentable sugars is sorbitol. In some aspects of these embodiments, sorbitol is present in the composition at an amount between about 5% to about 35% by weight. In some aspects of these embodiments, sorbitol is present in the composition at an amount between about 10% to about 35% by weight. In some aspects of these embodiments, sorbitol is present in the composition at an amount between about 17% to about 35% by weight. In some aspects of these embodiments, one of the non-fermentable sugars is xylitol. In some aspects of these embodiments, xylitol is present in the composition at an amount between about 2% to about 15% by weight. In some aspects of these embodiments, xylitol is present in the composition at about 2.5% by weight.

In some embodiments, the surfactant is a nonionic surfactant. In some aspects of these embodiments, the nonionic surfactant is a polysorbate, e.g., Polysorbate 20 or Polysorbate 80. In a preferred embodiment, the polysorbate is Polysorbate 20. In some aspects of this embodiment, the Polysorbate 20 is present in the composition at an amount of about 0.5% to about 2.5% by weight (e.g., about 0.5% to about 1.5%, about 1%).

In some embodiments, the thickener is glycerin. In some aspects of these embodiments, the glycerin is present in the composition at an amount of about 1% to about 20% by weight. In some aspects of these embodiments, the glycerin is present in the composition at about 10% to about 15% by weight (e.g., about 12.5%). In some aspects of these embodiments, the amount of PAAG present in the composition is reduced relative to a composition without glycerin.

In some embodiments, the flavoring agent is anethole, anise oil, bay oil, benzaldehyde, bergamot oil, bitter almond, camphor, cedar leaf oil, chlorothymol, cinnamic aldehyde, cinnamon oil, citronella oil, clove oil, coal tar, eucalyptol, eucaltyptus oil, eugenol, guaiacol, lavender oil, menthol, mustard oil, peppermint oil, phenol, phenyl salicyclate, pine oil, pine needle oil, rosemary oil, *sassafras* oil, spearmint oil, spike lavender oil, storax, thyme oil, thymol, tolu balsam, turpentine oil, wintergreen oil, or boric acid. In a preferred embodiment, the flavoring agent is peppermint oil. In some aspects of this embodiment, the peppermint oil is present in the composition at an amount of about 0.01% to about 0.3% by weight. In some aspects of these embodiments, the amount of PAAG present in the composition is reduced relative to a composition without flavoring agent.

In some embodiments, the preservative is benzoic acid. In some aspects of this embodiment, the benzoic acid is present in the composition at an amount of about 0.01% to about 4% by weight.

In some embodiments, the composition comprises an anti-caries agent. In some aspects of this embodiment, the anti-caries agent is a fluoride, e.g., sodium fluoride. In some aspects of this embodiment, the sodium fluoride is present in the composition at an amount of 0% to about 0.1% by weight.

In some embodiments, the composition further comprises sodium hydroxide. In some aspects of this embodiment, the sodium hydroxide is present in the composition at an amount of less than 0.25 by weight (e.g., less than 0.1%).

In some embodiments, the composition is an aqueous composition (e.g., comprising water).

In some embodiments, the composition is substantially free of artificial colors, artificial flavors, artificial preservatives, artificial sweeteners (e.g., saccharin), ethylene glycol, gluten, grapefruit seed extract, parabens, peroxides, phthalates, triclosan, sodium lauryl sulfate, or any agents that would damage the oral mucosa. In some embodiments, the composition is substantially free of one or more of alcohols.

In some embodiments, PAAG comprises the following formula (I):

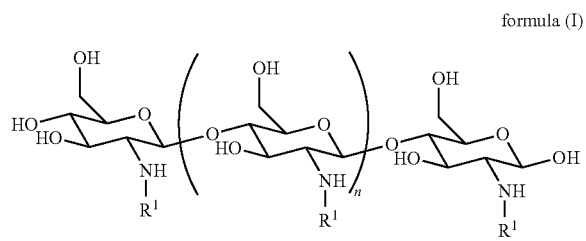

formula (I)

wherein:
n is an integer between 20 and 6000; and
each R¹ is independently selected for each occurrence from hydrogen, acetyl,

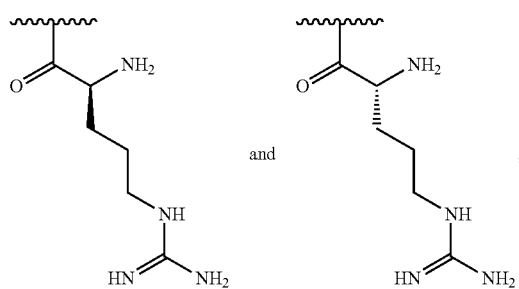

and wherein at least 25% of R¹ substituents are H, at least 1% of R¹ substituents are acetyl, and at least 2% of R¹ substituents are

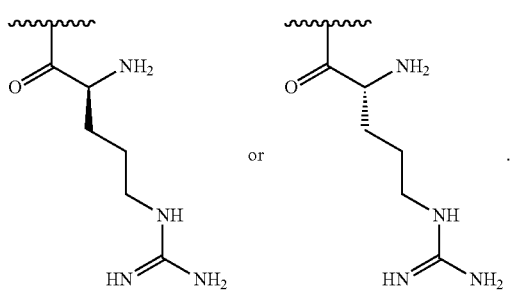 [SMILES: *C(=O)[C@@H](N)CCCNC(=N)N ; *C(=O)[C@H](N)CCCNC(=N)N]

or

In some embodiments, the functionalized polyglucosamine of formula (I) may be further derivatized on the free hydroxyl moieties.

In some embodiments, the molecular weight of the derivatized polyglucosamine is between 20 and 200 kDa. In some preferred embodiments, the molecular weight of the derivatized polyglucosamine is between 30 and 150 kDa.

In some embodiments, the derivatized polyglucosamine is soluble in aqueous solution (e.g., prepared in aqueous solution) between pH 3 and 11. In some embodiments, the derivatized polyglucosamine is soluble in aqueous solution (e.g., prepared in aqueous solution) between pH 2 and 10. In some embodiments, the derivatized polyglucosamine is soluble in aqueous solution (e.g., prepared in aqueous solution) between pH 5 and 9. In some embodiments, the derivatized polyglucosamine is soluble in aqueous solution (e.g., prepared in aqueous solution) between pH 6 and pH 8. In some embodiments, the derivatized polyglucosamine is soluble in aqueous solution (e.g., prepared in aqueous solution) between pH 6.5 and pH 8. In some embodiments, the derivatized polyglucosamine is soluble in aqueous solution (e.g., prepared in aqueous solution) between pH 7 and pH 8.

In some embodiments, the polyglucosamine is functionalized at between 5% and 50%. In some preferred embodiments, the polyglucosamine is functionalized at between 15% and 30%. In some preferred embodiments, the polyglucosamine is functionalized at between 18% and 30%.

In some embodiments, the degree of deacetylation (% DDA) of the derivatized polyglucosamine is between 75% and 99%. In some embodiments, the degree of deacetylation (% DDA) of the derivatized polyglucosamine is between 80% and 98%.

In some embodiments, the polydispersity index (PDI) of the derivatized polyglucosamine is between 1.0 and 2.5. In some embodiments, the polydispersity index (PDI) of the derivatized polyglucosamine is between 1.2 and 2.5. In some embodiments, the polydispersity index (PDI) of the derivatized polyglucosamine is between 1.5 and 2.0.

In some embodiments, the functionalized polyglucosamine is substantially free of other impurities.

In one aspect, the invention features an oral care composition comprising a non-fermentable sugar (e.g., sorbitol, xylitol) and a poly (acetyl, arginyl) glucosamine (PAAG), wherein the PAAG is present in the composition at an amount of at least 0.003% w/v. In some embodiments, the PAAG is present in the composition at an amount of at least 0.003% w/v to about 0.02% w/v of PAAG. In some embodiments, the PAAG is present in the composition at an amount of at least 0.003% w/v to about 0.01% w/v of PAAG.

In some embodiments, the composition further comprises a thickener (e.g., glycerin, glycerol), a surfactant (e.g., Polysorbate 20), a flavoring agent, or a preservative (e.g., benzoic acid). In some embodiments, the composition further comprises at least two of the following: a thickener (e.g., glycerin), a surfactant (e.g., Polysorbate 20), a flavoring agent, and a preservative (e.g., benzoic acid). In some embodiments, the composition further comprises at least three of the following: a thickener (e.g., glycerin), a surfactant (e.g., Polysorbate 20), a flavoring agent, and a preservative (e.g., benzoic acid). In some embodiments, the composition further comprises all of the following: a thickener (e.g., glycerin), a surfactant (e.g., Polysorbate 20), a flavoring agent, and a preservative (e.g., benzoic acid).

In some embodiments, the non-fermentable sugar comprises a plurality of non-fermentable sugars. In some aspects of these embodiments, the non-fermentable sugars are selected from a group consisting of sorbitol, xylitol, mannitol, glycerin, and erythritol. In some aspects of these embodiments, the non-fermentable sugars and PAAG are present in the composition at an amount of about 15% to about 70% w/v.

In some aspects of these embodiments, the PAAG is present in the composition at an amount of at least 0.003% to about 0.01% w/v of PAAG. In some aspects of these embodiments, the PAAG is present in the composition at an amount of at least 0.01% w/v of PAAG.

In some embodiments, the non-fermentable sugars are present in the composition at about 5% to about 65% w/v (e.g., about 10% to about 65% w/v, about 17% to about 65% w/v) and PAAG is present in the composition at at least 0.003% w/v. In some embodiments, the non-fermentable sugars are present in the composition at about 5% to about 65% w/v (e.g., about 10% to about 65% w/v, about 17% to about 65% w/v) and PAAG is present in the composition at at least 0.004% w/v. In some embodiments, the non-fermentable sugars are present in the composition at about 5% to about 65% w/v (e.g., about 10% to about 65% w/v, about 17% to about 65% w/v) and PAAG is present in the composition at about 0.003% w/v. In some embodiments, the non-fermentable sugars are present in the composition at about 5% to about 65% w/v (e.g., about 10% to about 65% w/v, about 17% to about 65% w/v) and PAAG is present in the composition at about 0.004% w/v. In some embodiments, the non-fermentable sugars are present in the composition at about 5% to about 65% w/v (e.g., about 10% to about 65% w/v, about 65% w/v, about 17% to about 65% w/v) and PAAG is present in the composition at about 0.015% to about 0.20% w/v (e.g., about 0.018% w/v). In some aspects of these embodiments, the amount of PAAG present in the composition is reduced relative to a composition without non-fermentable sugars. In some aspects of these embodiments, one of the non-fermentable sugars is sorbitol. In some aspects of these embodiments, sorbitol is present in the composition at an amount between about 5% to about 35% by weight. In some aspects of these embodiments, sorbitol is present in the composition at an amount between about 10% to about 35% by weight. In some aspects of these embodiments, sorbitol is present in the composition at an amount between about 17% to about 35% by weight. In some aspects of these embodiments, one of the non-fermentable sugars is xylitol. In some aspects of these embodiments, xylitol is present in the composition at an amount between about 2% to about 15% by weight. In some aspects of these embodiments, xylitol is present in the composition at about 2.5% by weight.

In some embodiments, the surfactant is a nonionic surfactant. In some aspects of these embodiments, the nonionic surfactant is a polysorbate, e.g., Polysorbate 20 or Polysorbate 80. In a preferred embodiment, the polysorbate is Polysorbate 20. In some aspects of this embodiment, the Polysorbate 20 is present in the composition at an amount of about 0.5% to about 2.5% by weight. (e.g., about 0.5% to about 1.5%, about 1%).

In some embodiments, the thickener is glycerin. In some aspects of these embodiments, the glycerin is present in the composition at an amount of about 1% to about 20% by weight. In some aspects of these embodiments, the glycerin is present in the composition at about 10% to about 15% by weight (e.g., about 12.5%). In some aspects of these embodiments, the amount of PAAG present in the composition is reduced relative to a composition without glycerin.

In some embodiments, the flavoring agent is anethole, anise oil, bay oil, benzaldehyde, bergamot oil, bitter almond, camphor, cedar leaf oil, chlorothymol, cinnamic aldehyde, cinnamon oil, citronella oil, clove oil, coal tar, eucalyptol, eucaltyptus oil, eugenol, guaiacol, lavender oil, menthol, mustard oil, peppermint oil, phenol, phenyl salicyclate, pine oil, pine needle oil, rosemary oil, *sassafras* oil, spearmint oil, spike lavender oil, storax, thyme oil, thymol, tolu balsam, turpentine oil, wintergreen oil, or boric acid. In a preferred embodiment, the flavoring agent is peppermint oil. In some aspects of this embodiment, the peppermint oil is present in the composition at an amount of about 0.01% to about 0.3% by weight. In some aspects of these embodiments, the amount of PAAG present in the composition is reduced relative to a composition without flavoring agent.

In some embodiments, the preservative is benzoic acid. In some aspects of this embodiment, the benzoic acid is present in the composition at an amount of about 0.01% to about 4% by weight.

In some embodiments, the composition comprises an anti-caries agent. In some aspects of this embodiment, the anti-caries agent is a fluoride, e.g., sodium fluoride. In some aspects of this embodiment, the sodium fluoride is present in the composition at an amount of 0% to about 0.1% by weight.

In some embodiments, the composition further comprises sodium hydroxide. In some aspects of this embodiment, the sodium hydroxide is present in the composition at an amount of less than 0.25% by weight (e.g., less than 0.1%).

In some embodiments, the composition is an aqueous composition (e.g., comprising water).

In some embodiments, the composition is substantially free of artificial colors, artificial flavors, artificial preservatives, artificial sweeteners (e.g., saccharin), ethylene glycol, gluten, grapefruit seed extract, parabens, peroxides, phthalates, triclosan, sodium lauryl sulfate, or any agents that would damage the oral mucosa. In some embodiments, the composition is substantially free of one or more of alcohols.

In some embodiments, PAAG comprises the following formula (I):

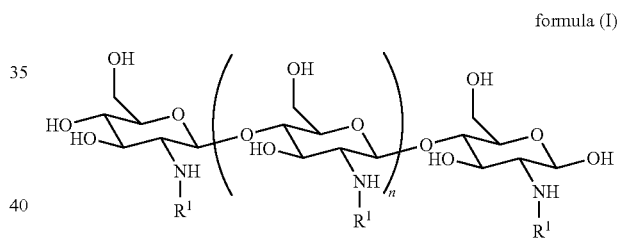

formula (I)

wherein:

n is an integer between 20 and 6000; and each $R^1$ is independently selected for each occurrence from hydrogen, acetyl,

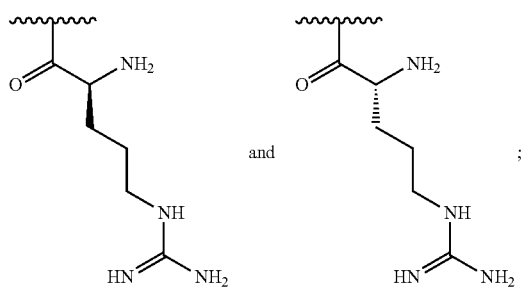 [SMILES: *C(=O)[C@@H](N)CCCNC(=N)N ; *C(=O)[C@H](N)CCCNC(=N)N]

and

;

wherein at least 25% of $R^1$ substituents are H, at least 1% of $R^1$ substituents are acetyl, and at least 2% of $R^1$ substituents are

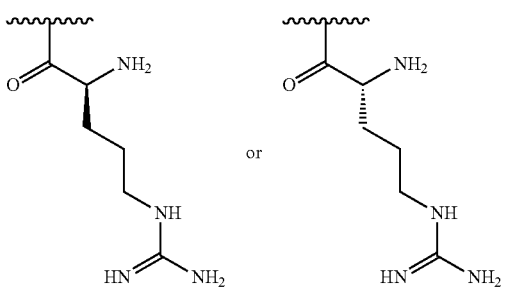

In some embodiments, the functionalized polyglucosamine of formula (I) may be further derivatized on the free hydroxyl moieties.

In some embodiments, the molecular weight of the derivatized polyglucosamine is between 20 and 200 kDa. In some preferred embodiments, the molecular weight of the derivatized polyglucosamine is between 30 and 150 kDa.

In some embodiments, the derivatized polyglucosamine is soluble in aqueous solution (e.g., prepared in aqueous solution) between pH 3 and 11. In some embodiments, the derivatized polyglucosamine is soluble in aqueous solution (e.g., prepared in aqueous solution) between pH 2 and 10. In some embodiments, the derivatized polyglucosamine is soluble in aqueous solution (e.g., prepared in aqueous solution) between pH 5 and 9. In some embodiments, the derivatized polyglucosamine is soluble in aqueous solution (e.g., prepared in aqueous solution) between pH 6 and pH 8. In some embodiments, the derivatized polyglucosamine is soluble in aqueous solution (e.g., prepared in aqueous solution) between pH 6.5 and pH 8. In some embodiments, the derivatized polyglucosamine is soluble in aqueous solution (e.g., prepared in aqueous solution) between pH 7 and pH 8.

In some embodiments, the polyglucosamine is functionalized at between 5% and 50%. In some preferred embodiments, the polyglucosamine is functionalized at between 15% and 30%. In some preferred embodiments, the polyglucosamine is functionalized at between 18% and 30%.

In some embodiments, the degree of deacetylation (% DDA) of the derivatized polyglucosamine is between 75% and 99%. In some embodiments, the degree of deacetylation (% DDA) of the derivatized polyglucosamine is between 80% and 98%.

In some embodiments, the polydispersity index (PDI) of the derivatized polyglucosamine is between 1.0 and 2.5. In some embodiments, the polydispersity index (PDI) of the derivatized polyglucosamine is between 1.2 and 2.5. In some embodiments, the polydispersity index (PDI) of the derivatized polyglucosamine is between 1.5 and 2.0.

In some embodiments, the functionalized polyglucosamine is substantially free of other impurities.

In one aspect, the invention features an oral care composition comprising a non-fermentable sugar (e.g., sorbitol and xylitol) in an amount from about 5% to about 65% w/v, glycerin in an amount from about 1% to about 20% w/v, Polysorbate 20 in an amount from about 0.5% to about 2.5% w/v, peppermint oil in an amount from about 0.01% to about 0.3% w/v, benzoic acid in an amount from about 0.01% to about 4.0% w/v, and PAAG in an amount from about 0.001 to about 0.8% w/v.

In some embodiments, the non-fermentable sugar comprises a plurality of non-fermentable sugars. In some aspects of these embodiments, the non-fermentable sugars are selected from a group consisting of sorbitol, xylitol, mannitol, glycerin, and erythritol. In some aspects of these embodiments, the non-fermentable sugars and PAAG are present in the composition at an amount of about 15% to about 70% w/v.

In some embodiments, the PAAG is present in the composition at an amount of at least 0.003% w/v of PAAG. In some aspects of these embodiments, the PAAG is present in the composition at an amount of at least 0.003% to about 0.05% w/v of PAAG. In some aspects of these embodiments, the PAAG is present in the composition at an amount of at least 0.003% to about 0.02% w/v of PAAG. In some aspects of these embodiments, the PAAG is present in the composition at an amount of at least 0.003% to about 0.01% w/v of PAAG. In some embodiments, the PAAG is present in the composition at an amount of at least 0.004% w/v of PAAG. In some aspects of these embodiments, the PAAG is present in the composition at an amount of at least 0.004% to about 0.05% w/v of PAAG. In some aspects of these embodiments, the PAAG is present in the composition at an amount of at least 0.004% to about 0.02% w/v of PAAG. In some aspects of these embodiments, the PAAG is present in the composition at an amount of at least 0.01% w/v of PAAG. In some aspects of these embodiments, the PAAG is present in the composition at an amount of at least 0.01% to about 0.05% w/v of PAAG. In some aspects of these embodiments, the PAAG is present in the composition at an amount of at least 0.01% to about 0.02% w/v of PAAG.

In some embodiments, the non-fermentable sugars are present in the composition at about 5% to about 65% w/v (e.g., about 10% to about 65% w/v, about 17% to about 65% w/v) and PAAG is present in the composition at at least 0.003% w/v. In some embodiments, the non-fermentable sugars are present in the composition at about 5% to about 65% w/v (e.g., about 10% to about 65% w/v, about 17% to about 65% w/v) and PAAG is present in the composition at at least 0.004% w/v. In some embodiments, the non-fermentable sugars are present in the composition at about 5% to about 65% w/v (e.g., about 10% to about 65% w/v, about 17% to about 65% w/v) and PAAG is present in the composition at about 0.003% w/v. In some embodiments, the non-fermentable sugars are present in the composition at about 5% to about 65% w/v (e.g., about 10% to about 65% w/v, about 17% to about 65% w/v) and PAAG is present in the composition at about 0.004% w/v. In some embodiments, the non-fermentable sugars are present in the composition at about 5% to about 65% w/v (e.g., about 10% to about 65% w/v, about 17% to about 65% w/v) and PAAG is present in the composition at about 0.015% to about 0.20% w/v (e.g., about 0.018% w/v). In some aspects of these embodiments, the amount of PAAG present in the composition is reduced relative to a composition without non-fermentable sugars. In some aspects of these embodiments, one of the non-fermentable sugars is sorbitol. In some aspects of these embodiments, sorbitol is present in the composition at an amount between about 5% to about 35% by weight. In some aspects of these embodiments, sorbitol is present in the composition at an amount between about 10% to about 35% by weight. In some aspects of these embodiments, sorbitol is present in the composition at an amount between about 17% to about 35% by weight. In some aspects of these embodiments, one of the non-fermentable sugars is xylitol. In some aspects of these embodiments, xylitol is present in the composition at an amount between about 2% to about 15% by weight. In some aspects of these embodiments, xylitol is present in the composition at about 2.5% by weight.

In some embodiments, the surfactant is a nonionic surfactant. In some aspects of these embodiments, the nonionic surfactant is a polysorbate, e.g., Polysorbate 20 or Polysorbate 80. In a preferred embodiment, the polysorbate is Polysorbate 20. In some aspects of this embodiment, the Polysorbate 20 is present in the composition at an amount of about 0.5% to about 2.5% by weight (e.g., about 0.5% to about 1.5%, about 1%).

In some embodiments, the thickener is glycerin. In some aspects of these embodiments, the glycerin is present in the composition at an amount of about 1% to about 20% by weight. In some aspects of these embodiments, the glycerin is present in the composition at about 10% to about 15% by weight (e.g., about 12.5%). In some aspects of these embodiments, the amount of PAAG present in the composition is reduced relative to a composition without glycerin.

In some embodiments, the flavoring agent is anethole, anise oil, bay oil, benzaldehyde, bergamot oil, bitter almond, camphor, cedar leaf oil, chlorothymol, cinnamic aldehyde, cinnamon oil, citronella oil, clove oil, coal tar, eucalyptol, eucaltyptus oil, eugenol, guaiacol, lavender oil, menthol, mustard oil, peppermint oil, phenol, phenyl salicyclate, pine oil, pine needle oil, rosemary oil, sassafras oil, spearmint oil, spike lavender oil, storax, thyme oil, thymol, tolu balsam, turpentine oil, wintergreen oil, or boric acid. In a preferred embodiment, the flavoring agent is peppermint oil. In some aspects of this embodiment, the peppermint oil is present in the composition at an amount of about 0.01% to about 0.3% by weight. In some aspects of these embodiments, the amount of PAAG present in the composition is reduced relative to a composition without flavoring agent.

In some embodiments, the preservative is benzoic acid. In some aspects of this embodiment, the benzoic acid is present in the composition at an amount of about 0.01% to about 4% by weight.

In some embodiments, the composition comprises an anti-caries agent. In some aspects of this embodiment, the anti-caries agent is a fluoride, e.g., sodium fluoride. In some aspects of this embodiment, the sodium fluoride is present in the composition at an amount of 0% to about 0.1% by weight.

In some embodiments, the composition further comprises sodium hydroxide. In some aspects of this embodiment, the sodium hydroxide is present in the composition at an amount of less than 0.25% by weight (e.g., less than 0.1%).

In some embodiments, the composition is an aqueous composition (e.g., comprising water).

In some embodiments, the composition is substantially free of artificial colors, artificial flavors, artificial preservatives, artificial sweeteners (e.g., saccharin), ethylene glycol, gluten, grapefruit seed extract, parabens, peroxides, phthalates, triclosan, sodium lauryl sulfate, or any agents that would damage the oral mucosa. In some embodiments, the composition is substantially free of one or more of alcohols.

In some embodiments, PAAG comprises the following formula (I):

formula (I)

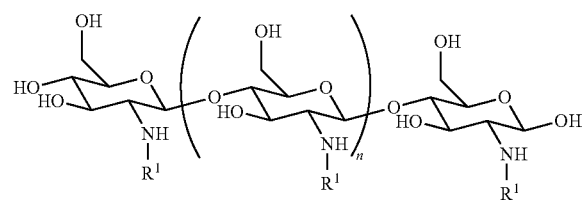

wherein:
n is an integer between 20 and 6000; and
each $R^1$ is independently selected for each occurrence from hydrogen, acetyl,

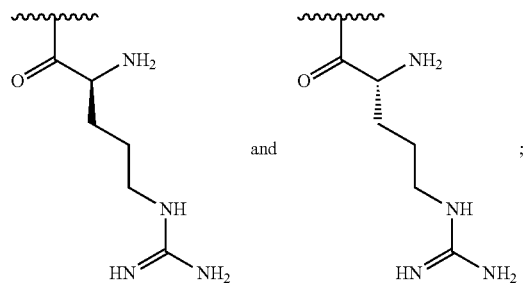 [SMILES: *C(=O)[C@@H](N)CCCNC(=N)N ; *C(=O)[C@H](N)CCCNC(=N)N]

and

;

wherein at least 25% of $R^1$ substituents are H, at least 1% of $R^1$ substituents are acetyl, and at least 2% of $R^1$ substituents an

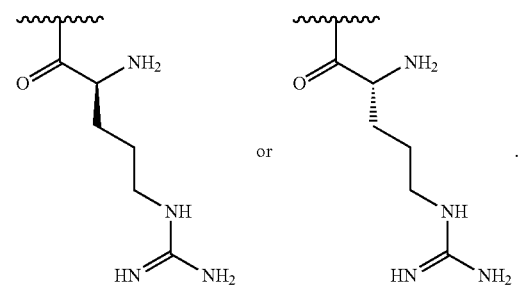

or

.

In some embodiments, the functionalized polyglucosamine of formula (I) may be further derivatized on the free hydroxyl moieties.

In some embodiments, the molecular weight of the derivatized polyglucosamine is between 20 and 200 kDa. In some preferred embodiments, the molecular weight of the derivatized polyglucosamine is between 30 and 150 kDa.

In some embodiments, the derivatized polyglucosamine is soluble in aqueous solution (e.g., prepared in aqueous solution) between pH 3 and 11. In some embodiments, the derivatized polyglucosamine is soluble in aqueous solution (e.g., prepared in aqueous solution) between pH 2 and 10. In some embodiments, the derivatized polyglucosamine is soluble in aqueous solution (e.g., prepared in aqueous solution) between pH 5 and 9. In some embodiments, the derivatized polyglucosamine is soluble in aqueous solution (e.g., prepared in aqueous solution) between pH 6 and pH 8. In some embodiments, the derivatized polyglucosamine is soluble in aqueous solution (e.g., prepared in aqueous solution) between pH 6.5 and pH 8. In some embodiments, the derivatized polyglucosamine is soluble in aqueous solution (e.g., prepared in aqueous solution) between pH 7 and pH 8.

In some embodiments, the polyglucosamine is functionalized at between 5% and 50%. In some preferred embodiments, the polyglucosamine is functionalized at between 15% and 30%. In some preferred embodiments, the polyglucosamine is functionalized at between 18% and 30%.

In some embodiments, the degree of deacetylation (% DDA) of the derivatized polyglucosamine is between 75% and 99%. In some embodiments, the degree of deacetylation (% DDA) of the derivatized polyglucosamine is between 80% and 98%.

In some embodiments, the polydispersity index (PDI) of the derivatized polyglucosamine is between 1.0 and 2.5. In some embodiments, the polydispersity index (PDI) of the derivatized polyglucosamine is between 1.2 and 2.5. In some embodiments, the polydispersity index (PDI) of the derivatized polyglucosamine is between 1.5 and 2.0.

In some embodiments, the functionalized polyglucosamine is substantially free of other impurities.

In one aspect, the invention features an oral care composition comprising a non-fermentable sugar (e.g., sorbitol and xylitol) in an amount from about 10% to about 65% w/v, glycerin in an amount from about 1% to about 20% w/v, Polysorbate 20 in an amount from about 0.5% to about 2.5% w/v, peppermint oil in an amount from about 0.01% to about 0.3% w/v, benzoic acid in an amount from about 0.01% to about 4.0% w/v, and PAAG in an amount from about 0.001 to about 0.8% w/v.

In some embodiments, the non-fermentable sugar comprises a plurality of non-fermentable sugars. In some aspects of these embodiments, the non-fermentable sugars are selected from a group consisting of sorbitol, xylitol, mannitol, glycerin, and erythritol. In some aspects of these embodiments, the non-fermentable sugars and PAAG are present in the composition at an amount of about 15% to about 70% w/v.

In some embodiments, the PAAG is present in the composition at an amount of at least 0.003% w/v of PAAG. In some aspects of these embodiments, the PAAG is present in the composition at an amount of at least 0.003% to about 0.05% w/v of PAAG. In some aspects of these embodiments, the PAAG is present in the composition at an amount of at least 0.003% to about 0.02% w/v of PAAG. In some aspects of these embodiments, the PAAG is present in the composition at an amount of at least 0.003% to about 0.01% w/v of PAAG. In some embodiments, the PAAG is present in the composition at an amount of at least 0.004% w/v of PAAG. In some aspects of these embodiments, the PAAG is present in the composition at an amount of at least 0.004% to about 0.05% w/v of PAAG. In some aspects of these embodiments, the PAAG is present in the composition at an amount of at least 0.004% to about 0.02% w/v of PAAG. In some aspects of these embodiments, the PAAG is present in the composition at an amount of at least 0.01% w/v of PAAG. In some aspects of these embodiments, the PAAG is present in the composition at an amount of at least 0.01% to about 0.05% w/v of PAAG. In some aspects of these embodiments, the PAAG is present in the composition at an amount of at least 0.01% to about 0.02% w/v of PAAG.

In some embodiments, the non-fermentable sugars are present in the composition at about 10% to about 65% w/v (about 17% to about 65% w/v) and PAAG is present in the composition at least 0.003% w/v. In some embodiments, the non-fermentable sugars are present in the composition at about 10% to about 65% w/v (about 17% to about 65% w/v) and PAAG is present in the composition at at least 0.004% w/v. In some embodiments, the non-fermentable sugars are present in the composition at about 10% to about 65% w/v (about 17% to about 65% w/v) and PAAG is present in the composition at about 0.003% w/v. In some embodiments, the non-fermentable sugars are present in the composition at about 10% to about 65% w/v (about 17% to about 65% w/v) and PAAG is present in the composition at about 0.004% w/v. In some embodiments, the non-fermentable sugars are present in the composition at about 10% to about 65% w/v (about 17% to about 65% w/v) and PAAG is present in the composition at about 0.015% to about 0.20% w/v (e.g., about 0.018% w/v). In some aspects of these embodiments, the amount of PAAG present in the composition is reduced relative to a composition without non-fermentable sugars. In some embodiments, one of the non-fermentable sugars is sorbitol. In some aspects of these embodiments, sorbitol is present in the composition at an amount between about 5% to about 35% by weight. In some aspects of these embodiments, sorbitol is present in the composition at an amount between about 10% to about 35% by weight. In some aspects of these embodiments, sorbitol is present in the composition at an amount between about 17% to about 35% by weight. In some aspects of these embodiments, one of the non-fermentable sugars is xylitol. In some aspects of these embodiments, xylitol is present in the composition at an amount between about 2% to about 15% by weight. In some aspects of these embodiments, xylitol is present in the composition at about 2.5% by weight.

In some embodiments, the surfactant is a nonionic surfactant. In some aspects of these embodiments, the nonionic surfactant is a polysorbate, e.g., Polysorbate 20 or Polysorbate 80. In a preferred embodiment, the polysorbate is Polysorbate 20. In some aspects of this embodiment, the Polysorbate 20 is present in the composition at an amount of about 0.5% to about 2.5% by weight (e.g., about 0.5% to about 1.5%, about 1%).

In some embodiments, the thickener is glycerin. In some aspects of these embodiments, the glycerin is present in the composition at an amount of about 1% to about 20% by weight. In some aspects of these embodiments, the glycerin is present in the composition at about 10% to about 15% by weight (e.g., about 12.5%). In some aspects of these embodiments, the amount of PAAG present in the composition is reduced relative to a composition without glycerin.

In some embodiments, the flavoring agent is anethole, anise oil, bay oil, benzaldehyde, bergamot oil, bitter almond, camphor, cedar leaf oil, chlorothymol, cinnamic aldehyde, cinnamon oil, citronella oil, clove oil, coal tar, eucalyptol, eucaltyptus oil, eugenol, guaiacol, lavender oil, menthol, mustard oil, peppermint oil, phenol, phenyl salicyclate, pine oil, pine needle oil, rosemary oil, *sassafras* oil, spearmint oil, spike lavender oil, storax, thyme oil, thymol, tolu balsam, turpentine oil, wintergreen oil, or boric acid. In a preferred embodiment, the flavoring agent is peppermint oil. In some aspects of this embodiment, the peppermint oil is present in the composition at an amount of about 0.01% to about 0.3% by weight. In some aspects of these embodiments, the amount of PAAG present in the composition is reduced relative to a composition without flavoring agent.

In some embodiments, the preservative is benzoic acid. In some aspects of this embodiment, the benzoic acid is present in the composition at an amount of about 0.01% to about 4% by weight.

In some embodiments, the composition comprises an anti-caries agent. In some aspects of this embodiment, the anti-caries agent is a fluoride, e.g., sodium fluoride. In some aspects of this embodiment, the sodium fluoride is present in the composition at an amount of 0% to about 0.1% by weight.

In some embodiments, the composition further comprises sodium hydroxide. In some aspects of this embodiment, the sodium hydroxide is present in the composition at an amount of less than 0.25% by weight (e.g., less than 0.1%).

In some embodiments, the composition is an aqueous composition (e.g., comprising water).

In some embodiments, the composition is substantially free of artificial colors, artificial flavors, artificial preservatives, artificial sweeteners (e.g., saccharin), ethylene glycol, gluten, grapefruit seed extract, parabens, peroxides, phthalates, triclosan, sodium lauryl sulfate, or any agents that would damage the oral mucosa. In some embodiments, the composition is substantially free of one or more of alcohols.

In some embodiments, PAAG comprises the following formula (I):

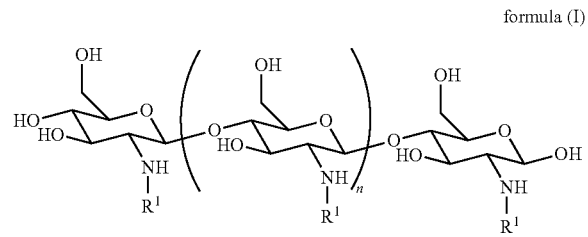

formula (I)

wherein:
n is an integer between 20 and 6000; and
each $R^1$ is independently selected for each occurrence from hydrogen, acetyl,

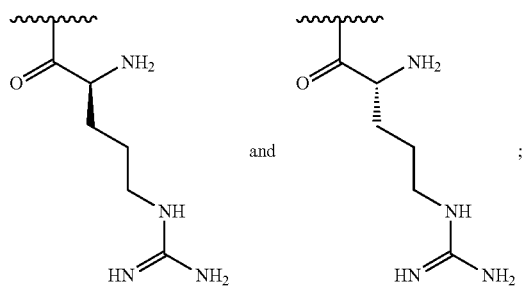

and ;

wherein at least 25% of $R^1$ substituents are H, at least 1% of $R^1$ substituents are acetyl, and at least 2% of $R^1$ substituents are

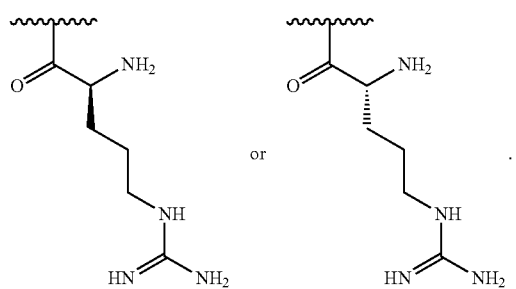 [SMILES: *C(=O)[C@@H](N)CCCNC(=N)N ; *C(=O)[C@H](N)CCCNC(=N)N]

or .

In some embodiments, the functionalized polyglucosamine of formula (I) may be further derivatized on the free hydroxyl moieties.

In some embodiments, the molecular weight of the derivatized polyglucosamine is between 20 and 200 kDa. In some preferred embodiments, the molecular weight of the derivatized polyglucosamine is between 30 and 150 kDa.

In some embodiments, the derivatized polyglucosamine is soluble in aqueous solution (e.g., prepared in aqueous solution) between pH 3 and 11. In some embodiments, the derivatized polyglucosamine is soluble in aqueous solution (e.g., prepared in aqueous solution) between pH 2 and 10. In some embodiments, the derivatized polyglucosamine is soluble in aqueous solution (e.g., prepared in aqueous solution) between pH 5 and 9. In some embodiments, the derivatized polyglucosamine is soluble in aqueous solution (e.g., prepared in aqueous solution) between pH 6 and pH 8. In some embodiments, the derivatized polyglucosamine is soluble in aqueous solution (e.g., prepared in aqueous solution) between pH 6.5 and pH 8. In some embodiments, the derivatized polyglucosamine is soluble in aqueous solution (e.g., prepared in aqueous solution) between pH 7 and pH 8.

In some embodiments, the polyglucosamine is functionalized at between 5% and 50%. In some preferred embodiments, the polyglucosamine is functionalized at between 15% and 30%. In some preferred embodiments, the polyglucosamine is functionalized at between 18% and 30%.

In some embodiments, the degree of deacetylation (% DDA) of the derivatized polyglucosamine is between 75% and 99%. In some embodiments, the degree of deacetylation (% DDA) of the derivatized polyglucosamine is between 80% and 98%.

In some embodiments, the polydispersity index (PDI) of the derivatized polyglucosamine is between 1.0 and 2.5. In some embodiments, the polydispersity index (PDI) of the derivatized polyglucosamine is between 1.2 and 2.5. In some embodiments, the polydispersity index (PDI) of the derivatized polyglucosamine is between 1.5 and 2.0.

In some embodiments, the functionalized polyglucosamine is substantially free of other impurities.

In one aspect, the invention features an oral care composition comprising a non-fermentable sugar (e.g., sorbitol and xylitol) in an amount from about 17% to about 65% w/v, glycerin in an amount from about 1% to about 20% w/v, Polysorbate 20 in an amount from about 0.5% to about 2.5% w/v, peppermint oil in an amount from about 0.01% to about 0.3% w/v, benzoic acid in an amount from about 0.01% to about 4.0% w/v, and PAAG in an amount from about 0.001 to about 0.8% w/v.

In some embodiments, the non-fermentable sugar comprises a plurality of non-fermentable sugars. In some aspects of these embodiments, the non-fermentable sugars are selected from a group consisting of sorbitol, xylitol, mannitol, glycerin, and erythritol. In some aspects of these embodiments, the non-fermentable sugars and PAAG are present in the composition at an amount of about 17% to about 70% w/v (e.g., about 17% to about 65% w/v).

In some embodiments, the PAAG is present in the composition at an amount of at least 0.003% w/v of PAAG. In some aspects of these embodiments, the PAAG is present in the composition at an amount of at least 0.003% to about 0.05% w/v of PAAG. In some aspects of these embodiments, the PAAG is present in the composition at an amount of at least 0.003% to about 0.02% w/v of PAAG. In some aspects of these embodiments, the PAAG is present in the composition at an amount of at least 0.003% to about 0.01% w/v of PAAG. In some embodiments, the PAAG is present in the composition at an amount of at least 0.004% w/v of PAAG. In some aspects of these embodiments, the PAAG is present in the composition at an amount of at least 0.004% to about 0.05% w/v of PAAG. In some aspects of these embodiments, the PAAG is present in the composition at an amount of at least 0.004% to about 0.02% w/v of PAAG. In some aspects of these embodiments, the PAAG is present in the composition at an amount of at least 0.01% w/v of PAAG. In some aspects of these embodiments, the PAAG is present in the composition at an amount of at least 0.01% to about 0.05% w/v of PAAG. In some aspects of these embodiments, the PAAG is present in the composition at an amount of at least 0.01% to about 0.02% w/v of PAAG.

In some embodiments, the non-fermentable sugars are present in the composition at about 17% to about 65% w/v and PAAG is present in the composition at at least 0.003% w/v. In some embodiments, the non-fermentable sugars are present in the composition at about 17% to about 65% w/v and PAAG is present in the composition at at least 0.004% w/v. In some embodiments, the non-fermentable sugars are present in the composition at about 17% to about 65% w/v and PAAG is present in the composition at about 0.003% w/v. In some embodiments, the non-fermentable sugars are present in the composition at about about 17% to about 65% w/v and PAAG is present in the composition at about 0.004% w/v. In some embodiments, the non-fermentable sugars are present in the composition at about about 17% to about 65% w/v and PAAG is present in the composition at about 0.015% to about 0.20% w/v (e.g., about 0.018% w/v). In some aspects of these embodiments, the amount of PAAG present in the composition is reduced relative to a composition without non-fermentable sugars. In some aspects of these embodiments, one of the non-fermentable sugars is sorbitol. In some aspects of these embodiments, sorbitol is present in the composition at an amount between about 5% to about 35% by weight. In some aspects of these embodiments, sorbitol is present in the composition at an amount between about 10% to about 35% by weight. In some aspects of these embodiments, sorbitol is present in the composition at an amount between about 17% to about 35% by weight. In some aspects of these embodiments, one of the non-fermentable sugars is xylitol. In some aspects of these embodiments, xylitol is present in the composition at an amount between about 2% to about 15% by weight. In some aspects of these embodiments, xylitol is present in the composition at about 2.5% by weight.

In some embodiments, the surfactant is a nonionic surfactant. In some aspects of these embodiments, the nonionic surfactant is a polysorbate, e.g., Polysorbate 20 or Polysorbate 80. In a preferred embodiment, the polysorbate is Polysorbate 20. In some aspects of this embodiment, the Polysorbate 20 is present in the composition at an amount of about 0.5% to about 2.5% by weight (e.g., about 0.5% to about 1.5%, about 1%).

In some embodiments, the thickener is glycerin. In some aspects of these embodiments, the glycerin is present in the composition at an amount of about 1% to about 20% by weight. In some aspects of these embodiments, the glycerin is present in the composition at about 10% to about 15% by weight (e.g., about 12.5%). In some aspects of these embodiments, the amount of PAAG present in the composition is reduced relative to a composition without glycerin.

In some embodiments, the flavoring agent is anethole, anise oil, bay oil, benzaldehyde, bergamot oil, bitter almond, camphor, cedar leaf oil, chlorothymol, cinnamic aldehyde, cinnamon oil, citronella oil, clove oil, coal tar, eucalyptol, eucaltyptus oil, eugenol, guaiacol, lavender oil, menthol, mustard oil, peppermint oil, phenol, phenyl salicyclate, pine oil, pine needle oil, rosemary oil, *sassafras* oil, spearmint oil, spike lavender oil, storax, thyme oil, thymol, tolu balsam, turpentine oil, wintergreen oil, or boric acid. In a preferred embodiment, the flavoring agent is peppermint oil. In some aspects of this embodiment, the peppermint oil is present in the composition at an amount of about 0.01% to about 0.3% by weight. In some aspects of these embodiments, the amount of PAAG present in the composition is reduced relative to a composition without flavoring agent.

In some embodiments, the preservative is benzoic acid. In some aspects of this embodiment, the benzoic acid is present in the composition at an amount of about 0.01% to about 4% by weight.

In some embodiments, the composition comprises an anti-caries agent. In some aspects of this embodiment, the anti-caries agent is a fluoride, e.g., sodium fluoride. In some aspects of this embodiment, the sodium fluoride is present in the composition at an amount of 0% to about 0.1% by weight.

In some embodiments, the composition further comprises sodium hydroxide. In some aspects of this embodiment, the sodium hydroxide is present in the composition at an amount of less than 0.25% by weight (e.g., less than 0.1%).

In some embodiments, the composition is an aqueous composition (e.g., comprising water).

In some embodiments, the composition is substantially free of artificial colors, artificial flavors, artificial preservatives, artificial sweeteners (e.g., saccharin), ethylene glycol, gluten, grapefruit seed extract, parabens, peroxides, phthalates, triclosan, sodium lauryl sulfate, or any agents that would damage the oral mucosa. In some embodiments, the composition is substantially free of one or more of alcohols.

In some embodiments, PAAG comprises the following formula (I):

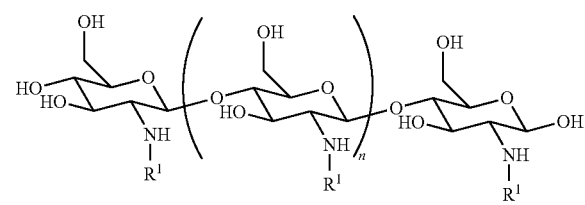

formula (I)

wherein:
n is an integer between 20 and 6000; and
each R¹ is independently selected for each occurrence from hydrogen, acetyl,

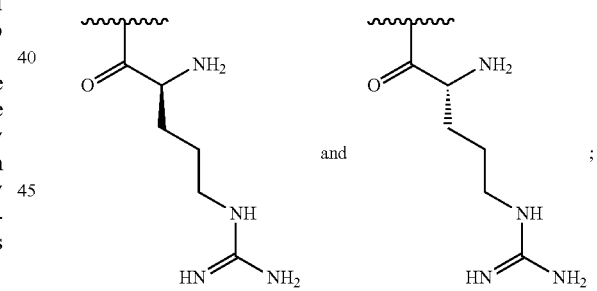

and ;

wherein at least 25% of R¹ substituents are H, at least 1% of R¹ substituents are acetyl, and at least 2% of R¹ substituents are

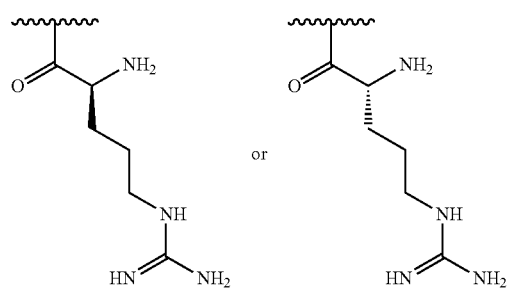

or .

In some embodiments, the functionalized polyglucosamine of formula (I) may be further derivatized on the free hydroxyl moieties.

In some embodiments, the molecular weight of the derivatized polyglucosamine is between 20 and 200 kDa. In some preferred embodiments, the molecular weight of the derivatized polyglucosamine is between 30 and 150 kDa.

In some embodiments, the derivatized polyglucosamine is soluble in aqueous solution (e.g., prepared in aqueous solution) between pH 3 and 11. In some embodiments, the derivatized polyglucosamine is soluble in aqueous solution (e.g., prepared in aqueous solution) between pH 2 and 10. In some embodiments, the derivatized polyglucosamine is soluble in aqueous solution (e.g., prepared in aqueous solution) between pH 5 and 9. In some embodiments, the derivatized polyglucosamine is soluble in aqueous solution (e.g., prepared in aqueous solution) between pH 6 and pH 8. In some embodiments, the derivatized polyglucosamine is soluble in aqueous solution (e.g., prepared in aqueous solution) between pH 6.5 and pH 8. In some embodiments, the derivatized polyglucosamine is soluble in aqueous solution (e.g., prepared in aqueous solution) between pH 7 and pH 8.

In some embodiments, the polyglucosamine is functionalized at between 5% and 50%. In some preferred embodiments, the polyglucosamine is functionalized at between 15% and 30%. In some preferred embodiments, the polyglucosamine is functionalized at between 18% and 30%.

In some embodiments, the degree of deacetylation (% DDA) of the derivatized polyglucosamine is between 75% and 99%. In some embodiments, the degree of deacetylation (% DDA) of the derivatized polyglucosamine is between 80% and 98%.

In some embodiments, the polydispersity index (PDI) of the derivatized polyglucosamine is between 1.0 and 2.5. In some embodiments, the polydispersity index (PDI) of the derivatized polyglucosamine is between 1.2 and 2.5. In some embodiments, the polydispersity index (PDI) of the derivatized polyglucosamine is between 1.5 and 2.0.

In some embodiments, the functionalized polyglucosamine is substantially free of other impurities.

In one aspect, the invention features an oral care composition comprising a non-fermentable sugar (e.g., sorbitol and xylitol) in an amount from about 22% to about 33% w/v (e.g., about 27.5% w/v), glycerin in an amount from about 5% to about 15% w/v (e.g., about 12.5% w/v), polysorbate 20 in an amount from about 1% to about 2% w/v (e.g., about 1% w/v), peppermint oil in an amount from about 0.1% to about 0.3% w/v (e.g., about 0.2% w/v), benzoic acid in an amount from about 0.01% to about 0.4% w/v (e.g., about 0.1% w/v), and a PAAG in an amount from about 0.001 to about 0.01% w/v (e.g., about 0.003% w/v, about 0.004% w/v).

In some embodiments, the non-fermentable sugar comprises a plurality of non-fermentable sugars. In some aspects of these embodiments, the non-fermentable sugars are selected from a group consisting of sorbitol, xylitol, mannitol, glycerin, and erythritol. In some aspects of these embodiments, the non-fermentable sugars and PAAG are present in the composition at an amount of about 22% to about 35% w/v.

In some aspects of these embodiments, the amount of PAAG present in the composition is reduced relative to a composition without non-fermentable sugars. In some aspects of these embodiments, one of the non-fermentable sugars is sorbitol. In some aspects of these embodiments, sorbitol is present in the composition at an amount between about 5% to about 35% by weight. In some aspects of these embodiments, sorbitol is present in the composition at an amount between about 10% to about 35% by weight. In some aspects of these embodiments, sorbitol is present in the composition at an amount between about 17% to about 35% by weight. In some aspects of these embodiments, one of the non-fermentable sugars is xylitol. In some aspects of these embodiments, xylitol is present in the composition at an amount between about 2% to about 15% by weight. In some aspects of these embodiments, xylitol is present in the composition at about 2.5% by weight.

In some embodiments, the composition comprises an anti-caries agent. In some aspects of this embodiment, the anti-caries agent is a fluoride, e.g., sodium fluoride. In some aspects of this embodiment, the sodium fluoride is present in the composition at an amount of 0% to about 0.1% by weight.

In some embodiments, the composition further comprises sodium hydroxide. In some aspects of this embodiment, the sodium hydroxide is present in the composition at an amount of less than 0.25% by weight (e.g., less than 0.1%).

In some embodiments, the composition is an aqueous composition (e.g., comprising water).

In some embodiments, the composition is substantially free of artificial colors, artificial flavors, artificial preservatives, artificial sweeteners (e.g., saccharin), ethylene glycol, gluten, grapefruit seed extract, parabens, peroxides, phthalates, triclosan, sodium lauryl sulfate, or any agents that would damage the oral mucosa. In some embodiments, the composition is substantially free of one or more of alcohols.

In some embodiments, PAAG comprises the following formula (I):

formula (I)

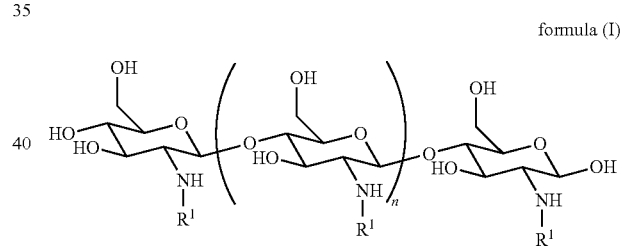

wherein:

n is an integer between 20 and 6000; and each $R^1$ is independently selected for each occurrence from hydrogen, acetyl,

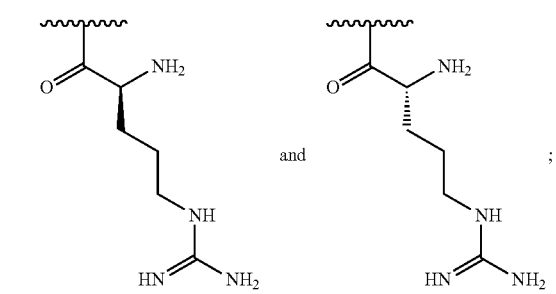 [SMILES: *C(=O)[C@@H](N)CCCNC(=N)N ; *C(=O)[C@H](N)CCCNC(=N)N]

and ;

wherein at least 25% of $R^1$ substituents are H, at least 1% of $R^1$ substituents are acetyl, and at least 2% of $R^1$ substituents are

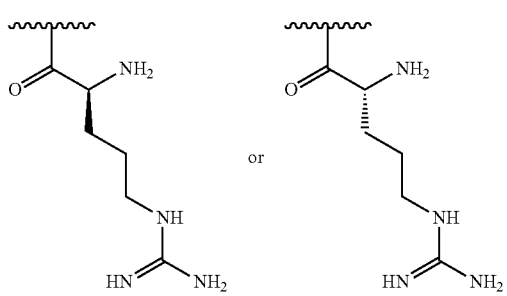

In some embodiments, the functionalized polyglucosamine of formula (I) may be further derivatized on the free hydroxyl moieties.

In some embodiments, the molecular weight of the derivatized polyglucosamine is between 20 and 200 kDa. In some preferred embodiments, the molecular weight of the derivatized polyglucosamine is between 30 and 150 kDa.

In some embodiments, the derivatized polyglucosamine is soluble in aqueous solution (e.g., prepared in aqueous solution) between pH 3 and 11. In some embodiments, the derivatized polyglucosamine is soluble in aqueous solution (e.g., prepared in aqueous solution) between pH 2 and 10. In some embodiments, the derivatized polyglucosamine is soluble in aqueous solution (e.g., prepared in aqueous solution) between pH 5 and 9. In some embodiments, the derivatized polyglucosamine is soluble in aqueous solution (e.g., prepared in aqueous solution) between pH 6 and pH 8. In some embodiments, the derivatized polyglucosamine is soluble in aqueous solution (e.g., prepared in aqueous solution) between pH 6.5 and pH 8. In some embodiments, the derivatized polyglucosamine is soluble in aqueous solution (e.g., prepared in aqueous solution) between pH 7 and pH 8.

In some embodiments, the polyglucosamine is functionalized at between 5% and 50%. In some preferred embodiments, the polyglucosamine is functionalized at between 15% and 30%. In some preferred embodiments, the polyglucosamine is functionalized at between 18% and 30%.

In some embodiments, the degree of deacetylation (% DDA) of the derivatized polyglucosamine is between 75% and 99%. In some embodiments, the degree of deacetylation (% DDA) of the derivatized polyglucosamine is between 80% and 98%.

In some embodiments, the polydispersity index (PDI) of the derivatized polyglucosamine is between 1.0 and 2.5. In some embodiments, the polydispersity index (PDI) of the derivatized polyglucosamine is between 1.2 and 2.5. In some embodiments, the polydispersity index (PDI) of the derivatized polyglucosamine is between 1.5 and 2.0.

In some embodiments, the functionalized polyglucosamine is substantially free of other impurities.

In one aspect, the invention features an oral care composition comprising a non-fermentable sugar (e.g., sorbitol and xylitol) in an amount from about 22% to about 33% w/v (e.g., about 27.5% w/v), glycerin in an amount from about 5% to about 15% w/v (e.g., about 12.5%), polysorbate 20 in an amount from about 1% to about 2% w/v (e.g., about 1% w/v), peppermint oil in an amount from about 0.1% to about 0.3% w/v (e.g., about 0.2% w/v), benzoic acid in an amount from about 0.01% to about 0.4% w/v (e.g., about 0.1% w/v), and a PAAG in an amount from about 0.001 to about 0.005% w/v (e.g., about 0.003% w/v, about 0.004% w/v).

In some embodiments, the non-fermentable sugar comprises a plurality of non-fermentable sugars. In some aspects of these embodiments, the non-fermentable sugars are selected from a group consisting of sorbitol, xylitol, mannitol, glycerin, and erythritol. In some aspects of these embodiments, the non-fermentable sugars and PAAG are present in the composition at an amount of about 22% to about 35% w/v.

In some aspects of these embodiments, the amount of PAAG present in the composition is reduced relative to a composition without non-fermentable sugars. In some aspects of these embodiments, one of the non-fermentable sugars is sorbitol. In some aspects of these embodiments, sorbitol is present in the composition at an amount between about 5% to about 35% by weight. In some aspects of these embodiments, sorbitol is present in the composition at an amount between about 10% to about 35% by weight. In some aspects of these embodiments, sorbitol is present in the composition at an amount between about 17% to about 35% by weight. In some aspects of these embodiments, one of the non-fermentable sugars is xylitol. In some aspects of these embodiments, xylitol is present in the composition at an amount between about 2% to about 15% by weight. In some aspects of these embodiments, xylitol is present in the composition at about 2.5% by weight.

In some embodiments, the composition comprises an anti-caries agent. In some aspects of this embodiment, the anti-caries agent is a fluoride, e.g., sodium fluoride. In some aspects of this embodiment, the sodium fluoride is present in the composition at an amount of 0% to about 0.1% by weight.

In some embodiments, the composition further comprises sodium hydroxide. In some aspects of this embodiment, the sodium hydroxide is present in the composition at an amount of less than 0.25% by weight (e.g., less than 0.1%).

In some embodiments, the composition is an aqueous composition (e.g., comprising water).

In some embodiments, the composition is substantially free of artificial colors, artificial flavors, artificial preservatives, artificial sweeteners (e.g., saccharin), ethylene glycol, gluten, grapefruit seed extract, parabens, peroxides, phthalates, triclosan, sodium lauryl sulfate, or any agents that would damage the oral mucosa. In some embodiments, the composition is substantially free of one or more of alcohols.

In some embodiments, PAAG comprises the following formula (I):

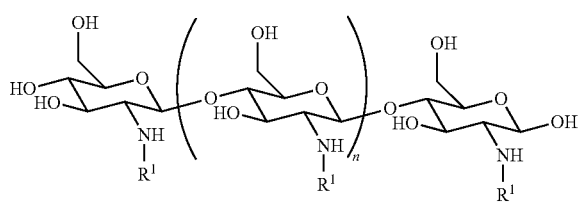

formula (I)

wherein:

n is an integer between 20 and 6000; and each $R^1$ is independently selected for each occurrence from hydrogen, acetyl,

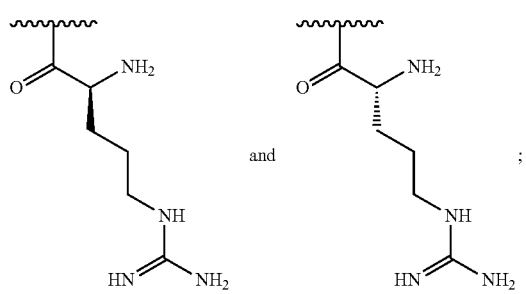 [SMILES: *C(=O)[C@@H](N)CCCNC(=N)N ; *C(=O)[C@H](N)CCCNC(=N)N]

wherein at least 25% of $R^1$ substituents are H, at least 1% of $R^1$ substituents are acetyl, and at least 2% of $R^1$ substituents are

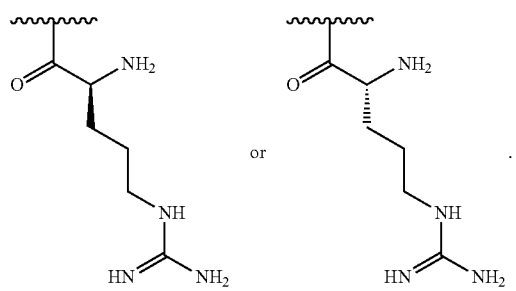 [SMILES: *C(=O)[C@@H](N)CCCNC(=N)N ; *C(=O)[C@H](N)CCCNC(=N)N]

In some embodiments, the functionalized polyglucosamine of formula (I) may be further derivatized on the free hydroxyl moieties.

In some embodiments, the molecular weight of the derivatized polyglucosamine is between 20 and 200 kDa. In some preferred embodiments, the molecular weight of the derivatized polyglucosamine is between 30 and 150 kDa.

In some embodiments, the derivatized polyglucosamine is soluble in aqueous solution (e.g., prepared in aqueous solution) between pH 3 and 11. In some embodiments, the derivatized polyglucosamine is soluble in aqueous solution (e.g., prepared in aqueous solution) between pH 2 and 10. In some embodiments, the derivatized polyglucosamine is soluble in aqueous solution (e.g., prepared in aqueous solution) between pH 5 and 9. In some embodiments, the derivatized polyglucosamine is soluble in aqueous solution (e.g., prepared in aqueous solution) between pH 6 and pH 8. In some embodiments, the derivatized polyglucosamine is soluble in aqueous solution (e.g., prepared in aqueous solution) between pH 6.5 and pH 8. In some embodiments, the derivatized polyglucosamine is soluble in aqueous solution (e.g., prepared in aqueous solution) between pH 7 and pH 8.

In some embodiments, the polyglucosamine is functionalized at between 5% and 50%. In some preferred embodiments, the polyglucosamine is functionalized at between 15% and 30%. In some preferred embodiments, the polyglucosamine is functionalized at between 18% and 30%.

In some embodiments, the degree of deacetylation (% DDA) of the derivatized polyglucosamine is between 75% and 99%. In some embodiments, the degree of deacetylation (% DDA) of the derivatized polyglucosamine is between 80% and 98%.

In some embodiments, the polydispersity index (PDI) of the derivatized polyglucosamine is between 1.0 and 2.5. In some embodiments, the polydispersity index (PDI) of the derivatized polyglucosamine is between 1.2 and 2.5. In some embodiments, the polydispersity index (PDI) of the derivatized polyglucosamine is between 1.5 and 2.0.

In some embodiments, the functionalized polyglucosamine is substantially free of other impurities.

In one aspect, the invention features an oral care composition comprising a non-fermentable sugar (e.g., sorbitol and xylitol) in an amount from about 22% to about 33% w/v (e.g., about 27.5% w/v), glycerin in an amount from about 5% to about 15% w/v (e.g., about 12.5% w/v), polysorbate 20 in an amount from about 1% to about 2% w/v (e.g., about 1% w/v), peppermint oil in an amount from about 0.1% to about 0.3% w/v (e.g., about 0.2% w/v), benzoic acid in an amount from about 0.01% to about 0.4% w/v (e.g., about 0.1% w/v), and a PAAG in an amount from about 0.003 to about 0.01% w/v (e.g., about 0.003% w/v, about 0.004% w/v).

In some embodiments, the non-fermentable sugar comprises a plurality of non-fermentable sugars. In some aspects of these embodiments, the non-fermentable sugars are selected from a group consisting of sorbitol, xylitol, mannitol, glycerin, and erythritol. In some aspects of these embodiments, the non-fermentable sugars and PAAG are present in the composition at an amount of about 22% to about 35% w/v.

In some aspects of these embodiments, the amount of PAAG present in the composition is reduced relative to a composition without non-fermentable sugars. In some aspects of these embodiments, one of the non-fermentable sugars is sorbitol. In some aspects of these embodiments, sorbitol is present in the composition at an amount between about 5% to about 35% by weight. In some aspects of these embodiments, sorbitol is present in the composition at an amount between about 10% to about 35% by weight. In some aspects of these embodiments, sorbitol is present in the composition at an amount between about 17% to about 35% by weight. In some aspects of these embodiments, one of the non-fermentable sugars is xylitol. In some aspects of these embodiments, xylitol is present in the composition at an amount between about 2% to about 15% by weight. In some aspects of these embodiments, xylitol is present in the composition at about 2.5% by weight.

In some embodiments, the composition comprises an anti-caries agent. In some aspects of this embodiment, the anti-caries agent is a fluoride, e.g., sodium fluoride. In some aspects of this embodiment, the sodium fluoride is present in the composition at an amount of 0% to about 0.1% by weight.

In some embodiments, the composition further comprises sodium hydroxide. In some aspects of this embodiment, the sodium hydroxide is present in the composition at an amount of less than 0.25% by weight (e.g., less than 0.1%).

In some embodiments, the composition is an aqueous composition (e.g., comprising water).

In some embodiments, the composition is substantially free of artificial colors, artificial flavors, artificial preservatives, artificial sweeteners (e.g., saccharin), ethylene glycol, gluten, grapefruit seed extract, parabens, peroxides, phthalates, triclosan, sodium lauryl sulfate, or any agents that would damage the oral mucosa. In some embodiments, the composition is substantially free of one or more of alcohols.

In some embodiments, PAAG comprises the following formula (I):

formula (I)

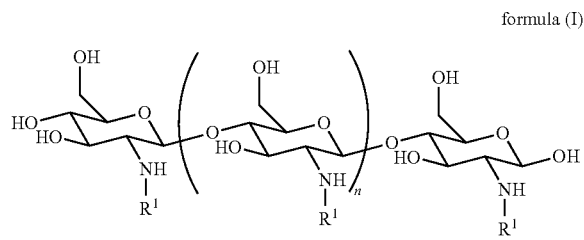

wherein:
n is an integer between 20 and 6000; and
each R¹ is independently selected for each occurrence from hydrogen, acetyl,

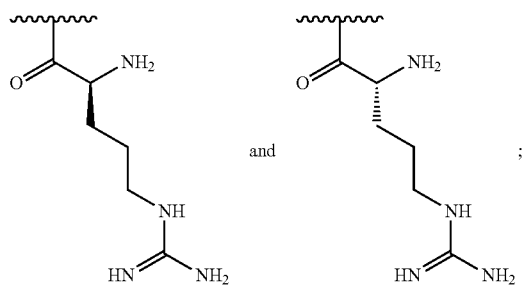 [SMILES: *C(=O)[C@@H](N)CCCNC(=N)N ; *C(=O)[C@H](N)CCCNC(=N)N]

wherein at least 25% of R¹ substituents are H, at least 1% of R¹ substituents are acetyl, and at least 2% of R¹ substituents are

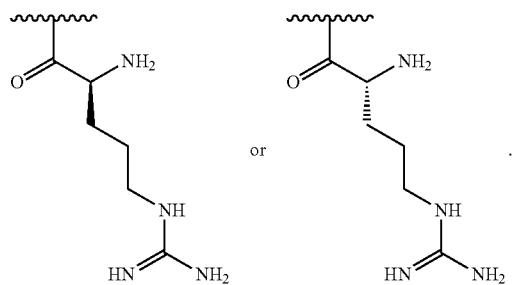 [SMILES: *C(=O)[C@@H](N)CCCNC(=N)N ; *C(=O)[C@H](N)CCCNC(=N)N]

In some embodiments, the functionalized polyglucosamine of formula (I) may be further derivatized on the free hydroxyl moieties.

In some embodiments, the molecular weight of the derivatized polyglucosamine is between 20 and 200 kDa. In some preferred embodiments, the molecular weight of the derivatized polyglucosamine is between 30 and 150 kDa.

In some embodiments, the derivatized polyglucosamine is soluble in aqueous solution (e.g., prepared in aqueous solution) between pH 3 and 11. In some embodiments, the derivatized polyglucosamine is soluble in aqueous solution (e.g., prepared in aqueous solution) between pH 2 and 10. In some embodiments, the derivatized polyglucosamine is soluble in aqueous solution (e.g., prepared in aqueous solution) between pH 5 and 9. In some embodiments, the derivatized polyglucosamine is soluble in aqueous solution (e.g., prepared in aqueous solution) between pH 6 and pH 8. In some embodiments, the derivatized polyglucosamine is soluble in aqueous solution (e.g., prepared in aqueous solution) between pH 6.5 and pH 8. In some embodiments, the derivatized polyglucosamine is soluble in aqueous solution (e.g., prepared in aqueous solution) between pH 7 and pH 8.

In some embodiments, the polyglucosamine is functionalized at between 5% and 50%. In some preferred embodiments, the polyglucosamine is functionalized at between 18% and 30%.

In some embodiments, the degree of deacetylation (% DDA) of the derivatized polyglucosamine is between 75% and 99%. In some embodiments, the degree of deacetylation (% DDA) of the derivatized polyglucosamine is between 80% and 98%.

In some embodiments, the polydispersity index (PDI) of the derivatized polyglucosamine is between 1.0 and 2.5. In some embodiments, the polydispersity index (PDI) of the derivatized polyglucosamine is between 1.2 and 2.5. In some embodiments, the polydispersity index (PDI) of the derivatized polyglucosamine is between 1.5 and 2.0.

In some embodiments, the functionalized polyglucosamine is substantially free of other impurities.

In one aspect, the invention features an oral care composition comprising a plurality non-fermentable sugars (e.g., sorbitol and xylitol) in an amount of about 27.5% w/v, glycerin in an amount of about 12.5% w/v, polysorbate 20 in an amount of about 1% w/v, peppermint oil in an amount of about 0.18% w/v, benzoic acid in an amount of about 0.1% w/v, and a PAAG in an amount of about 0.004% w/v.

In some embodiments, the non-fermentable sugar comprises a plurality of non-fermentable sugars. In some aspects of these embodiments, the non-fermentable sugars are selected from a group consisting of sorbitol, xylitol, mannitol, glycerin, and erythritol.

In some aspects of these embodiments, the amount of PAAG present in the composition is reduced relative to a composition without non-fermentable sugars. In some aspects of these embodiments, one of the non-fermentable sugars is sorbitol. In some aspects of these embodiments, sorbitol is present in the composition at an amount between about 5% to about 27.5% by weight (e.g., about 10% to about 27.5% by weight, about 17% to about 27.5% by weight, about 25% by weight). In some aspects of these embodiments, one of the non-fermentable sugars is xylitol. In some aspects of these embodiments, xylitol is present in the composition at an amount between about 2% to about 15% by weight. In some aspects of these embodiments, xylitol is present in the composition at about 2.5% by weight.

In some embodiments, the composition comprises an anti-caries agent. In some aspects of this embodiment, the anti-caries agent is a fluoride, e.g., sodium fluoride. In some aspects of this embodiment, the sodium fluoride is present in the composition at an amount of 0% to about 0.1% by weight.

In some embodiments, the composition further comprises sodium hydroxide. In some aspects of this embodiment, the sodium hydroxide is present in the composition at an amount of less than 0.25% by weight (e.g., less than 0.1%).

In some embodiments, the composition is an aqueous composition (e.g., comprising water).

In some embodiments, the composition is substantially free of artificial colors, artificial flavors, artificial preservatives, artificial sweeteners (e.g., saccharin), ethylene glycol, gluten, grapefruit seed extract, parabens, peroxides, phthalates, triclosan, sodium lauryl sulfate, or any agents that would damage the oral mucosa. In some embodiments, the composition is substantially free of one or more of alcohols.

In some embodiments, PAAG comprises the following formula (I):

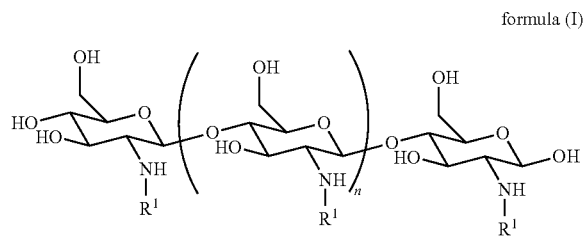

formula (I)

wherein:
n is an integer between 20 and 6000; and
each $R^1$ is independently selected for each occurrence from hydrogen, acetyl,

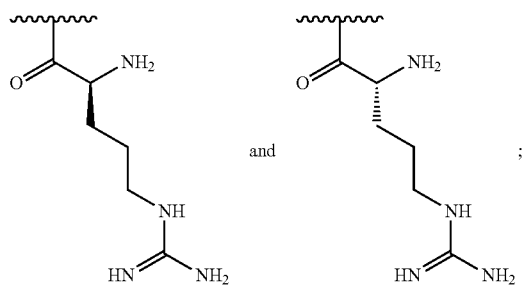 [SMILES: *C(=O)[C@@H](N)CCCNC(=N)N ; *C(=O)[C@H](N)CCCNC(=N)N]

and wherein at least 25% of $R^1$ substituents are H, at least 1% of $R^1$ substituents are acetyl, and at least 2% of $R^1$ substituents are

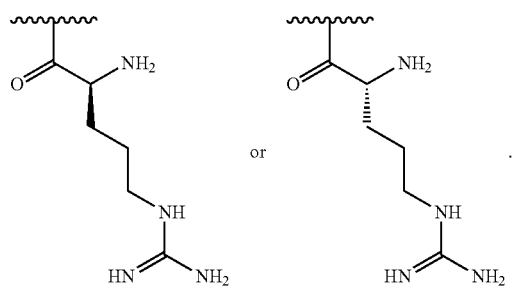 [SMILES: *C(=O)[C@@H](N)CCCNC(=N)N ; *C(=O)[C@H](N)CCCNC(=N)N]

or

.

In some embodiments, the functionalized polyglucosamine of formula (I) may be further derivatized on the free hydroxyl moieties.

In some embodiments, the molecular weight of the derivatized polyglucosamine is between 20 and 200 kDa. In some preferred embodiments, the molecular weight of the derivatized polyglucosamine is between 30 and 150 kDa.

In some embodiments, the derivatized polyglucosamine is soluble in aqueous solution (e.g., prepared in aqueous solution) between pH 3 and 11. In some embodiments, the derivatized polyglucosamine is soluble in aqueous solution (e.g., prepared in aqueous solution) between pH 2 and 10. In some embodiments, the derivatized polyglucosamine is soluble in aqueous solution (e.g., prepared in aqueous solution) between pH 5 and 9. In some embodiments, the derivatized polyglucosamine is soluble in aqueous solution (e.g., prepared in aqueous solution) between pH 6 and pH 8. In some embodiments, the derivatized polyglucosamine is soluble in aqueous solution (e.g., prepared in aqueous solution) between pH 6.5 and pH 8. In some embodiments, the derivatized polyglucosamine is soluble in aqueous solution (e.g., prepared in aqueous solution) between pH 7 and pH 8.

In some embodiments, the polyglucosamine is functionalized at between 5% and 50%. In some preferred embodiments, the polyglucosamine is functionalized at between 18% and 30%.

In some embodiments, the degree of deacetylation (% DDA) of the derivatized polyglucosamine is between 75% and 99%. In some embodiments, the degree of deacetylation (% DDA) of the derivatized polyglucosamine is between 80% and 98%.

In some embodiments, the polydispersity index (PDI) of the derivatized polyglucosamine is between 1.0 and 2.5. In some embodiments, the polydispersity index (PDI) of the derivatized polyglucosamine is between 1.2 and 2.5. In some embodiments, the polydispersity index (PDI) of the derivatized polyglucosamine is between 1.5 and 2.0.

In some embodiments, the functionalized polyglucosamine is substantially free of other impurities.

In one aspect, the invention features a method of treating or preventing an oral disease or a symptom of oral disease, the method comprising administering to the subject an effective amount of an oral care composition comprising PAAG. In some embodiments, the oral disease is periodontitis; gingivitis; dental caries; dental plaque; halitosis; swollen gums; mouth sores, oral lesions; bright-red, or purple gums; shiny gums; swollen gums that emit pus; severe oral odor; gums that are painless, except when pressure is applied; gums that bleed easily, even with gentle brushing, and especially when flossing; gums that itch with varying degrees of severity; or toothache. In some embodiments, the subject has oral diseases or conditions characterized by the presence of one or more of the bacteria from the group consisting of *Streptococcus mutans, Streptococcus sanguis, Treponema denticola, Porphyromonas gingivalis, Aggregatibacter actinomycetemcomitans, Fusospirochetes, Veillonella*, and some forms of pathogenic *Lactobacilli, Actinomyces viscosus*, or *Nocardia* spp.

In some embodiments, the method further comprises a step of administering an antibiotic or antiseptic to a subject, in a dosage to achieve a synergistic effect. In some aspects of these embodiments, the antibiotic or antiseptic is metronidazole, hydrogen peroxide, cetylpryridinium chloride, hypochlorite, chlorine dioxide, xylitol, or chlorhexidine.

In some embodiments, the method further comprises a step of physically removing superficial layers of bacteria, plaque and related debris from the mouth through use of mechanical or ultrasonic debridement.

In some embodiments, the composition contacts the mouth for about 0.5 to about 2 minutes. In some embodiments, the subject rinses the mouth with the composition for a period of at least 15 seconds. In some embodiments, the subject rinses the mouth with the composition for a period of at least 15 seconds to about 5 minutes. In some embodiments, the composition is not ingested by the subject. In some embodiments, the composition is ingested by the subject.

In some embodiments, the composition is used 1 to 6 times daily. In some embodiments, the composition is used 1 to 4 times daily. In some embodiments, the composition is used 1 to 2 times daily.

In some embodiments, the effective amount is about 5 to about 30 mL of the composition. In some embodiments, the effective amount is about 10 mL of the composition.

In one aspect, the invention features a method of removing plaque in the mouth of a subject, the method comprising administering to the subject an effective amount of an oral care composition comprising PAAG.

In some embodiments, the method further comprises a step of administering an antibiotic or antiseptic to a subject, in a dosage to achieve a synergistic effect. In some aspects of these embodiments, the antibiotic or antiseptic is metronidazole, hydrogen peroxide, cetylpryridinium chloride, hypochlorite, chlorine dioxide, xylitol, or chlorhexidine.

In some embodiments, the method further comprises a step of physically removing superficial layers of bacteria, plaque and related debris from the mouth through use of mechanical or ultrasonic debridement. In some embodiments, the composition contacts the mouth for about 0.5 to about 2 minutes. In some embodiments, the subject rinses the mouth with the composition for a period of at least 15 seconds. In some embodiments, the subject rinses the mouth with the composition for a period of at least 15 seconds to about 5 minutes. In some embodiments, the composition is not ingested by the subject. In some embodiments, the composition is ingested by the subject.

In some embodiments, the composition is used 1 to 6 times daily. In some embodiments, the composition is used 1 to 4 times daily. In some embodiments, the composition is used 1 to 2 times daily.

In some embodiments, the effective amount is about 5 to about 30 mL of the composition. In some embodiments, the effective amount is about 10 mL of the composition.

In one aspect, the invention features a method of reducing the formation of a biofilm or plaque in the mouth of a subject, the method comprising administering to the subject an effective amount of an oral care composition comprising poly (acetyl, arginyl) glucosamine (PAAG) (e.g., a composition as described herein, e.g., an oral care composition comprising a non-fermentable sugar and PAAG). In some embodiments, the method reduces the biofilm or plaque in the mouth of the subject by at least 10% compared to the amount of biofilm or plaque that would grow in the absence of use of the oral care composition comprising poly (acetyl, arginyl) glucosamine (PAAG).

In some embodiments, the method further comprises a step of administering an antibiotic or antiseptic to a subject, in a dosage to achieve a synergistic effect. In some aspects of these embodiments, the antibiotic or antiseptic is metronidazole, hydrogen peroxide, cetylpryridinium chloride, hypochlorite, chlorine dioxide, xylitol, or chlorhexidine.

In some embodiments, the method further comprises a step of physically removing superficial layers of bacteria, plaque and related debris from the mouth through use of mechanical or ultrasonic debridement.

In some embodiments, the composition contacts the mouth for about 0.5 to about 2 minutes. In some embodiments, the subject rinses the mouth with the composition for a period of at least 15 seconds. In some embodiments, the subject rinses the mouth with the composition for a period of at least 15 seconds to about 5 minutes. In some embodiments, the composition is not ingested by the subject. In some embodiments, the composition is ingested by the subject.

In some embodiments, the composition is used 1 to 6 times daily. In some embodiments, the composition is used 1 to 4 times daily. In some embodiments, the composition is used 1 to 2 times daily.

In some embodiments, the effective amount is about 5 to about 30 mL of the composition. In some embodiments, the effective amount is about 10 mL of the composition.

In one aspect, the invention features a method of treating or preventing gingivitis or periodontitis in a subject, the method comprising administering to the subject an effective amount of an oral care composition comprising PAAG.

In some embodiments, the method further comprises a step of administering an antibiotic or antiseptic to a subject, in a dosage to achieve a synergistic effect. In some aspects of these embodiments, the antibiotic or antiseptic is metronidazole, hydrogen peroxide, cetylpryridinium chloride, hypochlorite, chlorine dioxide, xylitol, or chlorhexidine.

In some embodiments, the method further comprises a step of physically removing superficial layers of bacteria, plaque and related debris from the mouth through use of mechanical or ultrasonic debridement.

In some embodiments, the composition contacts the mouth for about 0.5 to about 2 minutes. In some embodiments, the subject rinses the mouth with the composition for a period of at least 15 seconds. In some embodiments, the subject rinses the mouth with the composition for a period of at least 15 seconds to about 5 minutes. In some embodiments, the composition is not ingested by the subject. In some embodiments, the composition is ingested by the subject.

In some embodiments, the composition is used 1 to 6 times daily. In some embodiments, the composition is used 1 to 4 times daily. In some embodiments, the composition is used 1 to 2 times daily.

In some embodiments, the effective amount is about 5 to about 30 mL of the composition. In some embodiments, the effective amount is about 10 mL of the composition.

In one aspect, the invention features a method of treating or preventing halitosis in a subject, the method comprising administering to the subject an effective amount of an oral care composition comprising PAAG.

In some embodiments, the method further comprises a step of administering an antibiotic or antiseptic to a subject, in a dosage to achieve a synergistic effect. In some aspects of these embodiments, the antibiotic or antiseptic is metronidazole, hydrogen peroxide, cetylpryridinium chloride, hypochlorite, chlorine dioxide, xylitol, or chlorhexidine.

In some embodiments, the method further comprises a step of physically removing superficial layers of bacteria, plaque and related debris from the mouth through use of mechanical or ultrasonic debridement.

In some embodiments, the composition contacts the mouth for about 0.5 to about 2 minutes. In some embodiments, the subject rinses the mouth with the composition for a period of at least 15 seconds. In some embodiments, the subject rinses the mouth with the composition for a period of at least 15 seconds to about 5 minutes. In some embodiments, the composition is not ingested by the subject. In some embodiments, the composition is ingested by the subject.

In some embodiments, the composition is used 1 to 6 times daily. In some embodiments, the composition is used 1 to 4 times daily. In some embodiments, the composition is used 1 to 2 times daily.

In some embodiments, the effective amount is about 5 to about 30 mL of the composition. In some embodiments, the effective amount is about 10 mL of the composition.

In one aspect, the invention features a method of disrupting, reducing the viscosity of, or dissolving a preformed biofilm in the mouth of a subject, the method comprising administering to the subject an effective amount of an oral care composition comprising poly (acetyl, arginyl) glucosamine (PAAG) (e.g., a composition as described herein, e.g., an oral care composition comprising a non-fermentable sugar and PAAG). In some embodiments, the amount of preformed biofilm in the mouth of the subject is reduced by at least 10% compared to the amount of the bacteria that has not been contacted with the composition.

In some embodiments, the method further comprises a step of administering an antibiotic or antiseptic to a subject, in a dosage to achieve a synergistic effect. In some aspects of these embodiments, the antibiotic or antiseptic is metronidazole, hydrogen peroxide, cetylpryridinium chloride, hypochlorite, chlorine dioxide, xylitol, or chlorhexidine.

In some embodiments, the method further comprises a step of physically removing superficial layers of bacteria, plaque and related debris from the mouth through use of mechanical or ultrasonic debridement.

In some embodiments, the composition contacts the mouth for about 0.5 to about 2 minutes. In some embodiments, the subject rinses the mouth with the composition for a period of at least 15 seconds. In some embodiments, the subject rinses the mouth with the composition for a period of at least 15 seconds to about 5 minutes. In some embodiments, the composition is not ingested by the subject. In some embodiments, the composition is ingested by the subject.

In some embodiments, the composition is used 1 to 6 times daily. In some embodiments, the composition is used 1 to 4 times daily. In some embodiments, the composition is used 1 to 2 times daily.

In some embodiments, the effective amount is about 5 to about 30 mL of the composition. In some embodiments, the effective amount is about 10 mL of the composition.

In one aspect, the invention features a method of treating xerostomia in a subject, the method comprising administering to the subject an effective amount of an oral care composition comprising PAAG. In some embodiments, the method alleviates one or more symptoms of xerostomia.

In some embodiments, the method further comprises a step of administering an antibiotic or antiseptic to a subject, in a dosage to achieve a synergistic effect. In some aspects of these embodiments, the antibiotic or antiseptic is metronidazole, hydrogen peroxide, cetylpryridinium chloride, hypochlorite, chlorine dioxide, xylitol, or chlorhexidine.

In some embodiments, the method further comprises a step of physically removing superficial layers of bacteria, plaque and related debris from the mouth through use of mechanical or ultrasonic debridement.

In some embodiments, the composition contacts the mouth for about 0.5 to about 2 minutes. In some embodiments, the subject rinses the mouth with the composition for a period of at least 15 seconds. In some embodiments, the subject rinses the mouth with the composition for a period of at least 15 seconds to about 5 minutes. In some embodiments, the composition is not ingested by the subject. In some embodiments, the composition is ingested by the subject.

In some embodiments, the composition is used 1 to 6 times daily. In some embodiments, the composition is used 1 to 4 times daily. In some embodiments, the composition is used 1 to 2 times daily.

In some embodiments, the effective amount is about 5 to about 30 mL of the composition. In some embodiments, the effective amount is about 10 mL of the composition.

In one aspect, the invention features a method of moistening a mouth of a subject, the method comprising administering to the subject an effective amount of an oral care composition comprising PAAG. In some embodiments, the method replaces salivary flow.

In some embodiments, the method further comprises a step of administering an antibiotic or antiseptic to a subject, in a dosage to achieve a synergistic effect. In some aspects of these embodiments, the antibiotic or antiseptic is metronidazole, hydrogen peroxide, cetylpryridinium chloride, hypochlorite, chlorine dioxide, xylitol, or chlorhexidine.

In some embodiments, the method further comprises a step of physically removing superficial layers of bacteria, plaque and related debris from the mouth through use of mechanical or ultrasonic debridement.

In some embodiments, the composition contacts the mouth for about 0.5 to about 2 minutes. In some embodiments, the subject rinses the mouth with the composition for a period of at least 15 seconds. In some embodiments, the subject rinses the mouth with the composition for a period of at least 15 seconds to about 5 minutes. In some embodiments, the composition is not ingested by the subject. In some embodiments, the composition is ingested by the subject.

In some embodiments, the composition is used 1 to 6 times daily. In some embodiments, the composition is used 1 to 4 times daily. In some embodiments, the composition is used 1 to 2 times daily.

In some embodiments, the effective amount is about 5 to about 30 mL of the composition. In some embodiments, the effective amount is about 10 mL of the composition.

In one aspect, the invention features a method of cleaning teeth and gums in a subject, the method comprising administering to the subject an effective amount of an oral care composition comprising PAAG.

In some embodiments, the method further comprises a step of administering an antibiotic or antiseptic to a subject, in a dosage to achieve a synergistic effect. In some aspects of these embodiments, the antibiotic or antiseptic is metronidazole, hydrogen peroxide, cetylpryridinium chloride, hypochlorite, chlorine dioxide, xylitol, or chlorhexidine.

In some embodiments, the method further comprises a step of physically removing superficial layers of bacteria, plaque and related debris from the mouth through use of mechanical or ultrasonic debridement.

In some embodiments, the composition contacts the mouth for about 0.5 to about 2 minutes. In some embodiments, the subject rinses the mouth with the composition for a period of at least 15 seconds. In some embodiments, the subject rinses the mouth with the composition for a period of at least 15 seconds to about 5 minutes. In some embodiments, the composition is not ingested by the subject. In some embodiments, the composition is ingested by the subject.

In some embodiments, the composition is used 1 to 6 times daily. In some embodiments, the composition is used 1 to 4 times daily. In some embodiments, the composition is used 1 to 2 times daily.

In some embodiments, the effective amount is about 5 to about 30 mL of the composition. In some embodiments, the effective amount is about 10 mL of the composition.

DETAILED DESCRIPTION OF THE INVENTION

Described herein are methods and compositions that contain a soluble polyglucosamine or polyglucosamine derivative for use in oral health. The compositions are generally useful for reducing bacteria (e.g., by clumping and removing) or disrupting a biofilm in the mouth of a subject.

All percentages and ratios used hereinafter are by weight of a component used per volume of total composition, unless otherwise indicated. All percentages, ratios, and levels of ingredients referred to herein are based on the actual amount of the ingredient, and do not include solvents, fillers, or other materials with which the ingredient may be combined as commercially available product, unless otherwise indicated.

Compositions

Described herein are compositions comprising a soluble polyglucosamine or a derivatized polyglucosamine. In some embodiments, the composition is a liquid, solid, or semisolid composition. In some embodiments, the composition is an oral rinse (i.e., a mouth rise, mouth wash or oral wash).

In some embodiments, the composition further comprises one or more additional compound or agent. In some embodiments, the second compound or agent is a non-fermentable sugar, e.g., erythritol, mannitol, sorbitol, glycerin, xylitol, isomalt, lactitol, maltitol, or polyglycitol. In some embodiments, the non-fermentable sugars used in the composition are sorbitol and xylitol.

Described herein are also compositions containing a combination of a soluble polyglucosamine or a derivatized polyglucosamine described herein and a non-fermentable sugar, and methods of using a soluble polyglucosamine or a derivatized polyglucosamine in combination with a non-fermentable sugar for treating or preventing a disease or symptom of a disease described herein, e.g., an oral disease or a symptom of an oral disease, e.g., gingivitis, dental caries, dental plaque, halitosis.

In some embodiments, the combination of a soluble polyglucosamine or a derivatized polyglucosamine and a non-fermentable sugar results in a synergistic effect, e.g., a reduced effective concentration of either the soluble polyglucosamine or derivatized polyglucosamine or the non-fermentable sugar, or both. In some embodiments, the combination of a soluble polyglucosamine or a derivatized polyglucosamine and a non-fermentable sugar results in a synergistic effect, e.g., biofilm reduction at lower concentrations of either the soluble polyglucosamine or derivatized polyglucosamine or the non-fermentable sugar, or both.

In some embodiments, the composition has less than about 20%, 15%, 10%, 5%, 2%, or 1% by weight, or is substantially free, of a polyglucosamine polymer having a molecular weight of less than 15 kDa, 10 kDa, or 5 kDa.

Oral Rinse Compositions and Components

The compositions and components described herein can be provided in the form of an oral rinse. Ingredients of such an oral rinse typically include one or more of an active ingredient (e.g., a soluble polyglucosamine or derivatized polyglucosamine described herein e.g., from at least 0.0008%, from at least 0.001%, at least 0.003%, at least 0.004%, from about 0.001% to about 0.8%, from about 0.001% to about 0.005%, from about 0.003% to about 0.8%, from about 0.003% to about 0.02%, from about 0.003% to about 0.01%, from about 0.004% to about 0.8%, from about 0.004% to about 0.02%, from about 0.004% to about 0.01%), a non-fermentable sugar (e.g., from about 1% to about 70%, about 5% to about 70%, about 10% to about 70%, about 17% to about 70%, about 1% to about 65%, about 5% to about 70%, about 10% to about 70%, about 17% to about 65%, about 22% to about 33%), a thickener (e.g., from about 1% to about 20%, about 5% to about 15%, about 10% to about 15%, about 12.5%), a surfactant (e.g., from about 0.1% to about 2%, about 0.5% to about 2.5%, about 1% to about 2%, about 1%), a preservative (e.g., from about 0.01% to about 4%, from about 0.01 to about 0.4%, from about 0.01 to about 0.2%, from about 0.2% to about 0.4%, about 0.1%), and a flavoring agent (e.g., from about 0.01% to about 2%, about 0.01% to about 0.3%, about 0.2%). Such oral rinses may optionally include one or more of an anti-caries agent (from about 0% to about 0.1% as fluoride ion), an anti-calculus agent (from about 0.1% to about 3%), an antiseptic agent (e.g., thymol), an anesthetic agent (e.g., a local anesthetic agent (e.g., menthol)), a cleaning agent (e.g., methyl salicylate), a whitening agent (e.g., hydrogen peroxide), a base (e.g., sodium hydroxide), and a desensitizing agent (e.g., potassium nitrate). Examples of suitable oral rinse ingredients are described below.

Non Fermentable Sugars

Non-fermentable sugars or sugar alcohols are composed of a variety of monosaccharides or multimers that are not digested as a food source for some or all bacteria and typically not digested as a primary energy source by humans.

In some embodiments, the non-fermentable sugar is erythritol, mannitol, sorbitol, glycerin, xylitol, isomalt, lactitol, maltitol, or polyglycitol. In a preferred embodiment, the non-fermentable sugars used in the composition are sorbitol and xylitol. In some embodiments, the non-fermentable sugars are present in the composition at about 1% to about 65% w/v. In some embodiments, the non-fermentable sugars are present in the composition at about 17% to about 65% w/v. In some embodiments, the non-fermentable sugars are present in the composition at about 22% to about 33% w/v. In some embodiments, one of the non-fermentable sugars is sorbitol. In some embodiments, the sorbitol is present in the composition at an amount between about 1% to about 35% w/v. In some embodiments, the sorbitol is present in the composition at an amount between about 17% to about 35% w/v. In some embodiments, one of the non-fermentable sugars is xylitol. In some embodiments, the xylitol is present in the composition at an amount between about 2% to about 15% w/v.

Soluble Polyglucosamines and Polyglucosamines Derivatives

Compounds and compositions containing a soluble polyglucosamine or a derivatized polyglucosamine for treating or preventing a disease or symptom of a disease described herein, e.g., an oral disease or a symptom of an oral disease, e.g., gingivitis, dental caries, dental plaque, halitosis. Polyglucosamines can be derived from chitin or chitosan. Chitosan is an insoluble polymer derived from the deacetylation of chitin, which is a polymer of N-acetylglucosamine, that is the main component of the exoskeletons of crustaceans (e.g., shrimp, crab, lobster). Chitosan is generally a $\beta(1\rightarrow4)$ polyglucosamine that is less than 50% acetylated while chitin is generally considered to be more than 50% acetylated. Polyglucosamines are also found in various fungi and arthropods. Synthetic sources and alternate sources of $\beta(1\rightarrow4)$ polyglucosamines may serve as the starting material for polyglucosamine derivatives. Polyglucosamines, as opposed to polyacetylglucosamines, are defined herein to be less than 50% acetylated. If greater than 50% of the amino groups are acetylated, the polymer is considered a polyacetylglucosamine.

A soluble polyglucosamine described herein refers to a neutral pH, water soluble polyglucosamine or polyglucosamine that is not derivatized on the hydroxyl or amine moieties other than with acetyl groups. A soluble polyglucosamine comprises glucosamine and acetylglucosamine monomers. Generally, a water soluble polyglucosamine (at neutral pH) has a molecular weight of less than or equal to about 5,000 kDa and a degree of deacetylation equal to or greater than 80%.

A polyglucosamine derivative described herein is generated by functionalizing the free hydroxyl or amine groups with positively charged or neutral moieties. The percent of functionalization is defined as the total percent of monomers on the polyglucosamine backbone that have been functionalized with a positively charged or neutral moiety. The degrees of deacetylation and functionalization impart a specific charge density to the functionalized polyglucosamine derivative. The resulting charge density affects solubility and effectiveness of treatment. Thus, in accordance with the present invention, the degree of deacetylation, the functionalization and the molecular weight must be optimized for optimal efficacy. The polyglucosamine derivatives described herein have a number of properties which are advantageous, including solubility at physiologic (neutral) pH. In some embodiments, the polyglucosamine derivative is soluble up to a pH of 10. The polyglucosamine derivative described herein is soluble at pH 2 to pH 10. The polyglucosamine derivative described herein is soluble at pH 5 to pH 9. The polyglucosamine derivative described herein is soluble at pH 6 to pH 8. The polyglucosamine derivative described herein is soluble at pH 6.5 to pH 8. The polyglucosamine derivative described herein is soluble at pH 7 to pH 8. In some embodiments, the molecular weight of the polyglucosamine derivative is between 5 and 1,000 kDa. In some embodiments, the molecular weight of the polyglucosamine derivative is between 10 and 1,000 kDa. In some embodiments, the molecular weight of the polyglucosamine derivative is between 15 and 350 kDa. In some embodiments, the molecular weight of the polyglucosamine derivative is between 20 and 200 kDa. In some embodiments, the molecular weight of the polyglucosamine derivative is between 30 and 150 kDa.

Polyglucosamines with any degree of deacetylation (DDA) greater than 50% are used in the present invention, with functionalization between 2% and 50% of the total monomers on the polyglucosamine backbone. The degree of deacetylation determines the relative content of free amino groups to total monomers in the polyglucosamine polymer. Methods that can be used for determination of the degree of deacetylation of polyglucosamine include, e.g., ninhydrin test, linear potentiometric titration, near-infrared spectroscopy, nuclear magnetic resonance spectroscopy, hydrogen bromide titrimetry, infrared spectroscopy, and first derivative UV-spectrophotometry. Preferably, the degree of deacetylation of a soluble polyglucosamine or a derivatized polyglucosamine described herein is determined by quantitative infrared spectroscopy.

Percent functionalization by active derivitization of the amines is determined relative to the total number of monomers on the polyglucosamine polymer. Preferably, the percent functionalization of a derivatized polyglucosamine described herein is determined by H-NMR or quantitative elemental analysis. The degrees of deacetylation and functionalization impart a specific charge density to the functionalized polyglucosamine derivative. The resulting charge density affects solubility, and strength of interaction with tissue, biofilm components and bacterial membranes. The molecular weight is also an important factor in a derivatized polyglucosamine's mucoadhesivity and biofilm disrupting capability. Thus, in accordance with the present invention, these properties waist be optimized for optimal efficacy. Exemplary polyglucosamine derivatives are described in U.S. Pat. No. 8,119,780, which is incorporated herein by reference in its entirety.

The polyglucosamine derivatives described herein have a range of polydispersity index (PDT) between about 1.0 to about 3.0. The polyglucosamine derivatives described herein have a range of polydispersity index (PDI) between about 1.2 to about 2.8. The polyglucosamine derivatives described herein have a range of polydispersity index (PDI) between about 1.0 to about 2.5. The polyglucosamine derivatives described herein have a range of polydispersity index (PDT) between about 1.5 to about 2.0. As used herein, the polydispersity index (PDT), is a measure of the distribution of molecular weights in a given polymer sample. The PDI calculated is the weight averaged molecular weight divided by the number averaged molecular weight. This calculation indicates the distribution of individual molecular weights in a batch of polymers. The PDT has a value always greater than 1, but as the polymer chains approach uniform chain length, the PDT approaches unity (1). The PDT of a polymer derived from a natural source depends on the natural source (e.g., chitin or chitosan from crab vs. shrimp vs. fungi) and can be affected by a variety of reaction, production, processing, handling, storage and purifying conditions. Methods to determine the polydispersity include, e.g., gel permeation chromatography (also known as size exclusion chromatography); light scattering measurements; and direct calculation from MALDI or from electrospray mass spectrometry. Preferably, the PDI of a soluble polyglucosamine or a derivatized polyglucosamine described herein is determined by HPLC and multi angle light scattering methods.

The polyglucosamine derivatives (i.e., derivatized polyglucosamines) described herein have a variety of selected molecular weights that are soluble at neutral and physiological pH, and include for the purposes of this invention molecular weights ranging from 5-1,000 kDa. Derivatized polyglucosamines are soluble at pH up to about 10. Embodiments described herein are medium range molecular weight derivatized polyglucosamines (30-150 kDa, e.g., from about 30 to about 150 kDa). In some embodiments, the molecular weight of the derivatized polyglucosamine is between 10 and 1,000 kDa. In some embodiments, the molecular weight of the derivatized polyglucosamine is between 15 and 350 kDa. In some embodiments, the molecular weight of the derivatized polyglucosamine is between 20 and 200 kDa. In some embodiments, the molecular weight of the functionalized polyglucosamine is between 30 and 150 kDa.

The functionalized polyglucosamine derivatives described herein include the following:
  (A) Polyglucosamine-arginine compounds;
  (B) Polyglucosamine-natural amino acid derivative compounds;
  (C) Polyglucosamine-unnatural amino acid compounds;
  (D) Polyglucosamine-acid amine compounds;
  (E) Polyglucosamine-guanidine compounds; and
  (F) Neutral polyglucosamine derivative compounds,
  (A) Polyglucosamine-Arginine Compounds In some embodiments, the present invention is directed to polyglucosamine-arginine compounds, where the arginine is bound through a peptide (amide) bond via its carbonyl to the primary amine on the glucosamines of polyglucosamine:

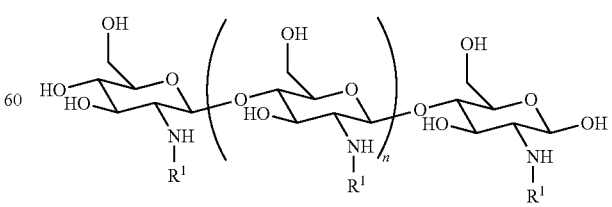

wherein each $R^1$ is independently selected from hydrogen, acetyl, and a group of the following formula:

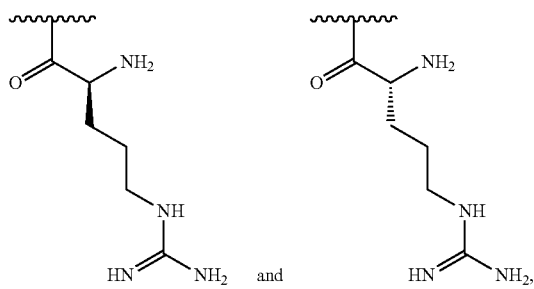 [SMILES: *C(=O)[C@@H](N)CCCNC(=N)N ; *C(=O)[C@H](N)CCCNC(=N)N]

or a racemic mixture thereof,
wherein at least 25% of $R^1$ substituents are H, at least 1% are acetyl, and at least 2% are a group of the formula shown above.

In some embodiments, a polyglucosamine-arginine compound is of the following formula

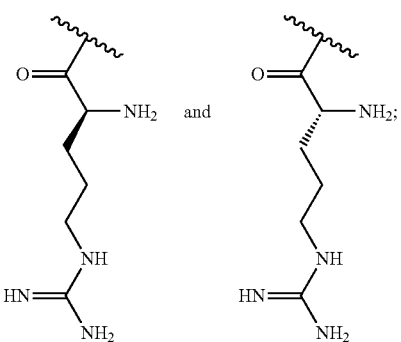

where m is 0.02-0.50; q is 0.50-0.01; s is 1; p+q+m=1; the percent degree of functionalization is m•100%; and X is selected from the group consisting of:

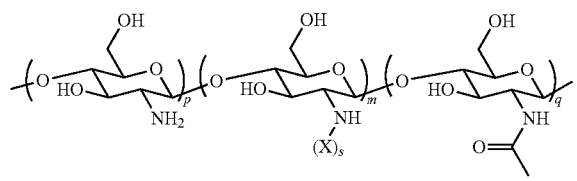

wherein the preparation is substantially free of compounds having a molecular weight of less than 5 kDa.

(B) Polyglucosamine-Natural Amino Acid Derivative Compounds

In some embodiments, the present invention is directed to polyglucosamine-natural amino acid derivative compounds, wherein the natural amino acid may be histidine or lysine. The amino is bound through a peptide (amide) bond via its carbonyl to the primary amine on the glucosamines of polyglucosamine:

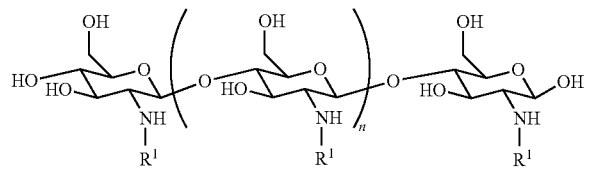

wherein each $R^1$ is independently selected from hydrogen, acetyl, and a group of the following formula:

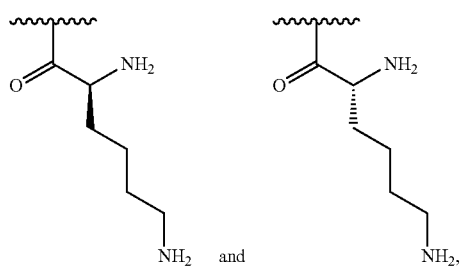 [SMILES: *C(=O)[C@@H](N)CCCCN ; *C(=O)[C@H](N)CCCCN]

or a racemic mixture thereof, wherein at least 25% of $R^1$ substituents are H, at least 1% are acetyl, and at least 2% are a group of the formula shown above; or a group of the following formula:

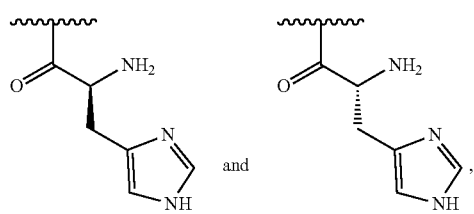 [SMILES: *C(=O)[C@@H](N)Cc1c[nH]cn1 ; *C(=O)[C@H](N)Cc1c[nH]cn1]

or a racemic mixture thereof, wherein at least 25% of $R^1$ substituents are H, at least 1% are acetyl, and at least 2% are a group of the formula shown above.

(C) Polyglucosamine-Unnatural Amino Acid Compounds

In some embodiments, the present invention is directed to polyglucosamine-unnatural amino acid compounds, where the unnatural amino acid is bound through a peptide (amide) bond via its carbonyl to the primary amine on the glucosamines of polyglucosamine:

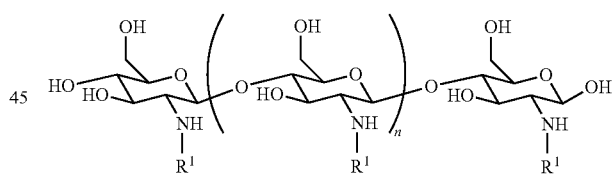

wherein each $R^1$ is independently selected from hydrogen, acetyl, and a group of the following formula:

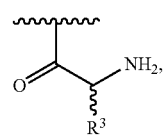

wherein $R^3$ is an unnatural amino acid side chain, and wherein at least 25% of $R^1$ substituents are H, at least 1% are acetyl, and at least 2% are a group of the formula shown above.

Unnatural amino acids are those with side chains not normally found in biological systems, such as ornithine (2,5-diaminopentanoic acid). Any unnatural amino acid may be used in accordance with the invention. In some embodiments, the unnatural amino acids coupled to polyglucosamine have the following formulae:

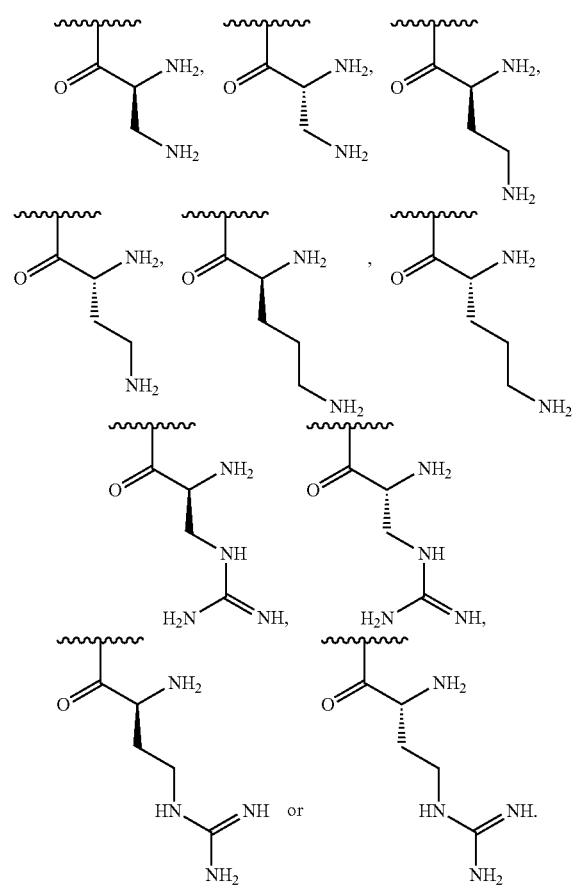

(D) Polyglucosamine-Acid Amine Compounds

In some embodiments, the present invention is directed to polyglucosamine-acid amine compounds, or their guanidylated counterparts. The acid amine is bound through a peptide (amide) bond via its carbonyl to the primary amine on the glucosamines of polyglucosamine:

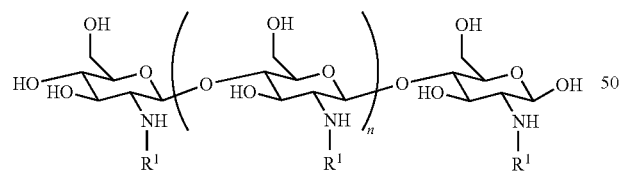

wherein each $R^1$ is independently selected from hydrogen, acetyl, and a group of the following formula:

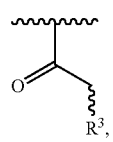

wherein $R^3$ is selected from amino, guanidino, and $C_1$-$C_6$ alkyl substituted with an amino or a guanidino group, wherein at least 25% of $R^1$ substituents are H, at least 1% are acetyl, and at least 2% are a group of the formula shown above In some embodiments, $R^1$ is selected from one of the following:

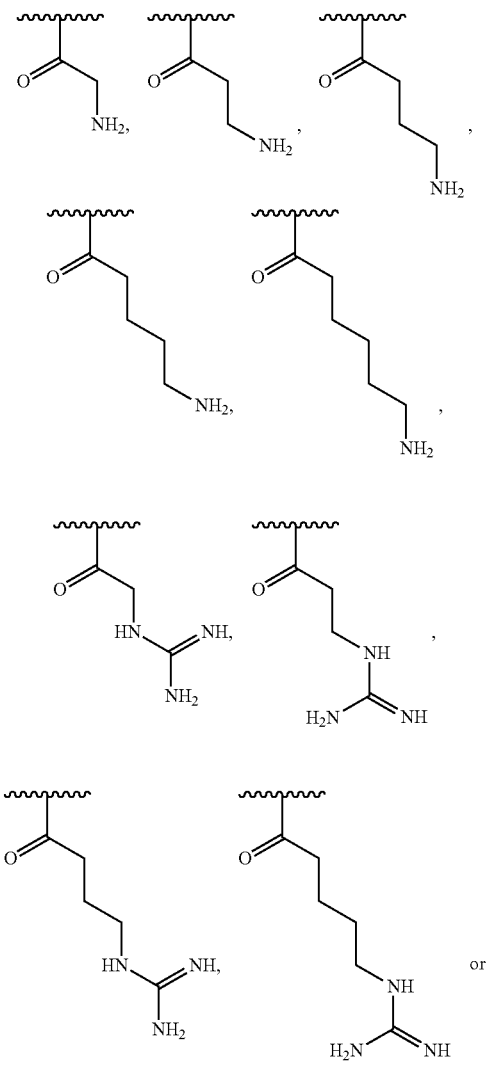

(E) Polyglucosamine-Guanidine Compounds

In some embodiments, the present invention is directed to polyglucosamine-guanidine compounds.

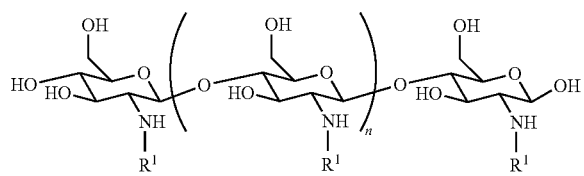

wherein each $R^1$ is independently selected from hydrogen, acetyl, and a group in which $R^1$, together with the nitrogen to which it is attached, forms a guanidine moiety; wherein at least 25% of $R^1$ substituents are H, at least 1% are acetyl, and at least 2% form a guanidine moiety together with the nitrogen to which it is attached.

(F) Neutral Polyglucosamine Derivative Compounds

In some embodiments, the present invention is directed to neutral polyglucosamine derivative compounds. Exemplary neutral polyglucosamine derivative compounds include those where one or more amine nitrogens of the polyglucosamine have been covalently attached to a neutral moiety such as a sugar:

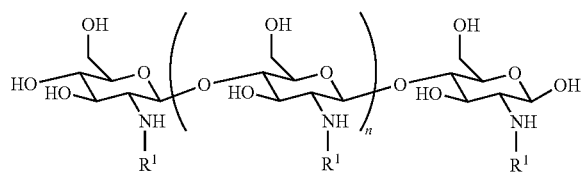

wherein each $R^1$ is independently selected from hydrogen, acetyl, and a sugar (e.g., a naturally occurring or modified sugar) or an α-hydroxy acid. Sugars can be monosaccharides, disaccharides or polysaccharides such as glucose, mannose, lactose, maltose, cellubiose, sucrose, amylose, glycogen, cellulose, gluconate, or pyruvate. Sugars can be covalently attached via a spacer or via the carboxylic acid, ketone or aldehyde group of the terminal sugar. Examples of α-hydroxy acids include glycolic acid, lactic acid, and citric acid. In some preferred embodiments, the neutral polyglucosamine derivative is polyglucosamine-lactobionic acid compound or polyglucosamine-glycolic acid compound. Exemplary salts and coderivatives include those known in the art, for example, those described in U.S. Pat. No. 8,119,780, the contents of which is incorporated by reference in its entirety.

In a preferred embodiment, the polyglucosamine derivative used in the composition is polyglucosamine-arginine, otherwise known as poly (acetyl, arginyl) glucosamine or PAAG. In some embodiments, the polyglucosamine-arginine is present in the composition at least 0.0008%. In some embodiments, the polyglucosamine-arginine is present in the composition at least 0.001%. In some embodiments, the polyglucosamine-arginine is present in the composition at least 0.003%. In some embodiments, the polyglucosamine-arginine is present in the composition at least 0.004%. In some embodiments, the polyglucosamine-arginine is present in the composition at least 0.001% to about 0.8%. In some embodiments, the polyglucosamine-arginine is present in the composition at least 0.003% to about 0.02%. In some embodiments, the polyglucosamine-arginine is present in the composition at least 0.003% to about 0.01%, In some embodiments, the polyglucosamine-arginine is present in the composition at least 0.004% to about 0.02%. In some embodiments, the polyglucosamine-arginine is present in the composition at least 0.004% to about 0.01%. In some embodiments, the polyglucosamine-arginine is present in the composition at least 0.001% to about 0.005%.

Surfactants

In some instances, the oral rinse may include one or more surfactants to provide a desirable foaming quality or to solubilize other insoluble components (e.g., benzoic acid). Surfactants generally include anionic, nonionic, cationic and zwitterionic or amphoteric compositions. Examples of surfactants include soaps, sulfates (e.g., sodium lauryl sulfate and sodium dodecyl benzene sulfonate), sodium lauryl sarcosinate, sorbitan esters of fatty acids, sulfobetaines (e.g., cocamidopropylbatine), and D-glucopyranoside $C_{10-16}$ alkyl oligomeric. In some embodiments, the surfactants include sodium lauryl sulphate, cocamidopropyl betaine, and D-glucopyranoside, oligomeric, $C_{10}$-$C_{16}$ alkylglycosides.

Preferably, the surfactant used in the compositions of the present invention is a non-ionic surfactant or anionic surfactant employed in an amount sufficient to help solubilize the flavoring agent. By sufficient amount it is meant that the surfactant is present in an amount that effectively assists in the solubilization of the flavoring agent.

In some embodiments, the surfactant is a nonionic surfactant. In some embodiments, the nonionic surfactant is a polysorbate. In some embodiments, the surfactant is Polysorbate 20 or Polysorbate 80. In a preferred embodiment, the surfactant is Polysorbate 20. In some embodiments of the invention the amount of surfactant present in the composition is about 0.1% to about 2%. In some embodiments of the invention the amount of surfactant present in the composition is about 0.5% to about 2.5%. In some embodiments of the invention the amount of surfactant present in the composition is about 1% to about 2%. In some embodiments of the invention the amount of surfactant present in the composition is about 1%.

Thickeners

A thickener is a substance that increases the viscosity of a solution or liquid/solid mixture without substantially modifying its other properties. Examples of thickening agents include thickening silica, polymers, clays, and combinations thereof (e.g., glycerin, xanthan gum, polyvinylpyrrolidone, hydroxyethyl cellulose, or sodium carboxymethylcellulose). A thickener may also reduce the total water content to help control undesirable growth of contaminants and microorganisms.

In a preferred embodiment, the thickener is glycerin. In some embodiments of the invention the amount of thickener present in the composition is about 5% to about 15%. In some embodiments of the invention the amount of thickener present in the composition is about 12.5%.

Preservatives

Examples of preservatives include anti-bacterial agents, anti-fungal agents (e.g., benzoic acid and sorbic acid), bacteriostatic agents (e.g., thimersol, phenyl mercuric acetate, phenyl mercuric nitrate, and sodium azide), fungistatic agents, and enzyme inhibitors.

In a preferred embodiment, the preservative is benzoic acid (or benzoate). In some embodiments of the invention the amount of preservative present in the composition is about 0.01% to about 4%. In some embodiments of the invention the amount of preservative present in the composition is about 0.2% to about 0.4%, In some embodiments of the invention the amount of preservative present in the composition is about 0.1%, Anti-Caries Agents Examples of anti-caries agents include water soluble fluoride salts, fluorosilicates, fluorozirconates, fluorostannites, fluoroborates, fluorotitanates, fluorogermanates, mixed halides and casine.

In a preferred embodiment, the anti-caries agent is a water soluble fluoride salt. In some embodiments, the water-soluble fluoride salt is sodium fluoride. In some embodiments, the sodium fluoride is present in the composition at about 0% to about 0.1%.

Anti-Calculus Agents

Examples of anti-calculus agents are typically acids or chelators that dissolve the mineral deposits and include alkali-metal pyrophosphates, hypophosphite-containing polymers, enzymes (e.g., lactoferrin), organic phosphocitrates, phosphocitrates, and polyphosphates.

Flavoring Agents

The flavoring agent may be anethole, anise oil, bay oil, benzaldehyde, bergamot oil, bitter almond, camphor, cedar leaf oil, chlorothymol, cinnamic aldehyde, cinnamon oil, citronella oil, clove oil, coal tar, eucalyptol, eucaltyptus oil, eugenol, guaiacol, lavender oil, menthol, mustard oil, peppermint oil, phenol, phenyl salicyclate, pine oil, pine needle oil, rosemary oil, sassafras oil, spearmint oil, spike lavender oil, storax, thyme oil, thymol, tolu balsam, turpentine oil, wintergreen oil, and boric acid.

Other flavor oils such as citrus oils, vanillin and the like may be incorporated to provide further taste variations.

The particular flavor oils and other taste-improving ingredients employed will vary depending upon the particular taste and feel desired. Those skilled in the art can select and customize these types of ingredients to provide the desired results.

In a preferred embodiment, the flavoring agent is peppermint oil. In some embodiments, the peppermint oil is present in the composition at about 0.1% to about 2%. In some embodiments, the peppermint oil is present in the composition at about 0.1% to about 0.3%. In some embodiments, the peppermint oil is present in the composition at about 0.2%.

As used herein, the words "preferred", "preferably" and variants refer to embodiments of the invention that afford certain benefits, under certain circumstances. Other embodiments may also be preferred, under the same or other circumstances. Recitation of one or more preferred embodiments do not imply that other embodiments are not useful or are intended to be excluded from the scope of the invention.

By "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity.

The oral care composition of the present invention may be in various forms including toothpaste, dentifrice, tooth gel, subgingival gel, mouth rinse, mouthwash, oral rinse, denture product, mouthspray, lozenge, chewable tablet or chewing gum. The oral care composition may also be incorporated onto strips or films for dissolution or for direct application or attachment to oral surfaces.

Active and other ingredients useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated application or applications listed.

Herein, the terms "tartar" and "calculus" are used interchangeably and refer to mineralized dental plaque Formulations and Routes of Administration The compounds described herein can be formulated in a variety of manners, including for oral treatment and oral delivery (e.g., administered orally). In some embodiments, oral rinse (mouthwash) is used for the oral delivery of a compound described herein, to reduce bacteria in the mouth, or to treat or prevent an oral disease or condition, e.g., dental plaque, gingivitis, oral lesions, dental caries, or halitosis. In some embodiments, dentifrice (e.g., toothpaste, liquid, tooth powder, tooth gel, or tooth strip), gum, lozenge, or sucker is used for the oral delivery of a compound described herein, to reduce bacteria in the mouth, or to treat or prevent an oral disease or condition, e.g., dental plaque, gingivitis, dental caries, or halitosis.

The compounds described herein (e.g., a soluble polyglucosamine or a derivatized polyglucosamine) can, for example, be administered for treatment in the oral cavity at concentrations from about 1 µg/mL to about 10 mg/mL, about 10 µg/mL to about 10 mg/mL, about 100 µg/mL to about 10 mg/mL, about 500 µg/mL to about 10 mg/mL, about 1 mg/mL to about 10 mg/mL, about 2 mg/mL to about 10 mg/mL, about 5 mg/mL to about 10 mg/mL, about 1 µg/mL to about 5 mg/mL, about 1 µg/mL to about 2 mg/mL, about 1 µg/mL to about 1 mg/mL, about 1 µg/mL to about 500 µg/mL, about 1 µg/mL to about 100 µg/mL, or about 1 µg/mL to about 50 µg/mL, for example, as required based on the severity of the oral disease and the compliance of the patient, for about 30 sec to about 2 minute, about 30 sec to about 1 minute, or about 1 minute to about 2 minute rinse. A preferred embodiment is a about 30 mL volume administration of from about 10 µg/mL to about 100 µg/mL of the compounds described herein for an about 30 sec to about 2 minute rinse. The compound described herein can be administered before or after the onset of the disorder described herein. The methods herein contemplate administration of an effective amount of compound or compound composition to achieve the desired or stated effect. Typically, the compositions of this invention will be administered from about 1 to about 6 times, about 1 to about 4 times, or about 2 to about 3 times per day.

Lower or higher doses than those recited above may be required. Specific dosage and treatment regimens for any particular patient will depend upon a variety of factors, including the activity of the specific compound employed, the age, body weight, general health status, sex, diet, time of administration, drug combination, the severity and course of the disease, condition or symptoms, the patient's disposition to the disease, condition or symptoms, and the judgment of the treating physician.

Bacterial Clumping

Bacterial population, e.g., in a body cavity or epithelial/mucosal surfaces in a subject, can be reduced (e.g., to a level closer to the normal microbial level) by clumping using compounds and compositions described herein. Described herein are also methods of treatment to reduce the colonization of e.g., the mouth, teeth, or throat by pathogenic bacteria.

This clumping can, in some embodiments, act as a "barrier," for example, when a composition described herein is used to contact a bacterial population so as to result in clumping of the bacteria onto the polyglucosamine derivative, and the resulting composition is discarded by the subject (e.g., spit out, for example, as an oral rinse).

The method of clumping (e.g., barrier clumping) includes the step of contacting compositions or compounds described herein (e.g., soluble polyglucosamines or derivatized polyglucosamines) with bacteria, e.g., in the mouth or epithelial/mucosal surfaces. The soluble polyglucosamine or polyglucosamine derivatives described herein can interact with more than one bacterium simultaneously, linking them via a part of the polymer chain. Thus, the contact can cause the bacteria to aggregate with one another. These bacteria within clumps are limited in their ability to bind to other surfaces, thereby creating a barrier to colonization by the bacteria. This barrier is a result of the decreased bacterial surface area available for colonization, the bacterial trapping within the aggregate as well as limitation of the exposure of bacterial surface receptors that are often used by bacteria to associate with biological or inert surfaces, thereby preventing the colonizing of pathogenic bacteria.

Polyglucosamine derivatives, e.g., polyglucosamine-arginine, act though physical means to reduce bacteria in the mouth, and can serve as an adjunct to normal mechanical oral hygiene. The polyglucosamine derivatives in the oral rinse act to prevent the adhesion of bacteria to the dental enamel by clumping the bacteria and allowing for easy removal from the oral cavity during rinsing through a physical interaction between the positively charged polyglucosamine-arginine and the negatively charged cell wall of oral bacteria.

The positively charged characteristic of polyglucosamine derivatives, e.g., polyglucosamine-arginine, allows the composition described herein to be effective in clumping and aggregating oral bacteria. The positively charged polymer interacts with the negatively charged cell wall of the oral bacteria electrostatically. This, in turn, allows the long polymer chains of polyglucosamine derivatives, e.g., polyglucosamine-arginine, to interact with the bacterial cell surface and bridge between bacteria cells. This interaction allows for clumping and aggregation of the oral bacteria cells and prevents them from adhering to oral surfaces. This mechanical action allows for easy removal of the bacteria from the oral cavity during rinsing.

Biofilm/Plaque

Methods and compositions described herein can be used to disrupt (e.g., reduce the viscosity of, or dissolve) a preformed biofilm in a subject, e.g., in the mouth. In the oral cavity, a preformed biofilm is referred to as a plaque.

As used herein, the term "dissolve" or "dissolving" means breaking up cohesion in a preformed biofilm such that some or all can be rinsed, flushed or washed away. Methods and compositions described herein can also be used to prevent the formation of a biofilm (e.g., reduce the ability of a biofilm to form) in the mouth of a subject.

A biofilm is a structured community of microorganisms encapsulated within a self-developed polymeric matrix and adherent to a living or inert surface. Biofilms are also often characterized by; surface attachment, structural heterogeneity, genetic diversity, complex community interactions, and an extracellular matrix of polymeric substances.

Formation of a biofilm begins with the attachment of free-floating microorganisms to a surface. This first bacterial colonization occurs through adhesion to the surface initially through weak, reversible van der Waals forces. If the bacteria are not immediately separated from the surface, they can anchor themselves more permanently. The first adherent bacteria facilitate the arrival of other cells by providing diverse adhesion sites and beginning to build the matrix that holds the biofilm together. The final stage of biofilm formation is typically known as development, and is the stage in which the biofilm is established and may only change in shape and size. This development of biofilm environment and communication pathway allows for the cells to become more antibiotic resistant.

The biofilm is held together and protected by a matrix of excreted polymeric compounds called the Extracellular Polymeric Substance (EPS). This matrix protects the cells within it and facilitates communication among them through biochemical signals.

Bacteria living in a biofilm can have different properties from free-floating bacteria of the same species, as the dense and protected environment of the film allows them to cooperate and interact in various ways. One benefit of this environment to the bacteria is increased resistance to detergents and antibiotics, as the dense extracellular matrix and the outer layer of cells protect the interior of the community.

Exemplary bacteria associated with biofilm in the mouth include *Streptococcus mutans, Streptococcus sanguis, Treponema denticola, Porphyromonas gingivalis, Aggregatibacter actinomycetemcomitans, Fusospirochetes, Veillonella*, and some forms of pathogenic *Lactobacilli, Actinomyces viscosus*, or *Nocardia* spp.

Exemplary bacteria associated with biofilm in the mouth also include bacteria causing oral diseases or conditions, e.g., dental plaque, gingivitis, dental caries, or halitosis. Exemplary bacteria associated with infections in the mouth also include bacteria causing tissue or wound infections in the mouth, ear, nose and throat.

As used herein, resistant microorganism or bacterium means an organism that has become resistant to an antibacterial agent. Also, resistant microorganism or bacterium means its effective minimum inhibitory concentration (MIC) has exceeded the effective dosage according to Clinical Laboratory Standards Institute (CLSI) resistance breakpoints, predefined national or internationally accepted limits, at or above which administration of an effective dose of antibiotic produces undesirable side effects. In some embodiments, the MIC of a resistant bacterium will be at least, 2, 5, 10, or 100 times greater than for that seen with a non-resistant bacterium for a selected anti-bacterial agent.

Exemplary oral diseases and conditions associated with biofilm can also include oral diseases and conditions characterized by the presence of one or more of the bacteria that cause resistant bacterial infections as described herein.

Treatment

The compositions and compounds described herein (e.g., a soluble polyglucosamine or a derivatized polyglucosamine) can be administered to a subject, e.g., in vivo, to treat, prevent, and/or diagnose a variety of disorders, including those described herein below.

As used herein, the term "treat" or "treatment" is defined as the application or administration of a composition or compound (e.g., a compound described herein (e.g., a soluble polyglucosamine or a derivatized polyglucosamine) to a subject, e.g., a patient, or application or administration of the composition or compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, the term "prevent" or "prevention" is defined as the application or administration of a composition or compound (e.g., a compound described herein (e.g., a soluble polyglucosamine or a derivatized polyglucosamine)) to a subject, e.g., a subject who is at risk for a disorder (e.g., a disorder described herein), or has a predisposition toward a disorder, with the purpose to avoid or preclude the disorder, or affect the predisposition toward the disorder (e.g., to prevent at least one symptom of the disorder or to delay onset of at least one symptom of the disorder).

As used herein, an amount of a composition or compound effective to treat a disorder, or a "therapeutically effective amount" refers to an amount of the composition or compound which is effective, upon single or multiple dose administration to a subject, in curing, alleviating, relieving or improving a subject with a disorder beyond that expected in the absence of such treatment.

As used herein, an amount of a composition or compound effective to prevent a disorder, or "a prophylactically effective amount" of the composition or compound refers to an amount effective, upon single- or multiple-dose administration to the subject, in preventing or delaying the occurrence of the onset or recurrence of a disorder or a symptom of the disorder.

As used herein, "administered in combination" or a combined administration of two agents means that two or more agents (e.g., compounds described herein) are administered to a subject at the same time or within an interval such that there is overlap of an effect of each agent on the patient. Preferably they are administered within 15, 10, 5, or 1 minute of one another. Preferably the administrations of the agents are spaced sufficiently close together such that a combinatorial (e.g., a synergistic) effect is achieved. Exemplary combinations of a derivatized polyglucosamine described herein and one or more of antimicrobial agent(s) such as an antibiotic are described, e.g., in US Publication US20100130443, which is incorporated by reference herein by its entirety. The combinations can have synergistic effect when used to treat a subject having a bacterial infection. The agents can be administered simultaneously, for example in a combined unit dose (providing simultaneous delivery of both agents). Alternatively, the agents can be administered at a specified time interval, for example, an interval of minutes, hours, days or weeks. Generally, the agents are concurrently bioavailable, e.g., detectable, in the subject.

In a preferred embodiment, the agents are administered essentially simultaneously, for example two unit dosages administered at the same time, or a combined unit dosage of the two agents. In another preferred embodiment, the agents are delivered in separate unit dosages. The agents can be administered in any order, or as one or more preparations that includes two or more agents. In a preferred embodiment, at least one administration of one of the agents, e.g., the first agent, is made within minutes, one, two, three, or four hours, or even within one or two days of the other agent, e.g., the second agent. In some cases, combinations can achieve synergistic results, e.g., greater than additive results, e.g., at least 1.5, 2.0, 5, 10, 20, 50, or 100 times greater than additive.

Subject

The subject can be a human or a non-human animal (e.g., dogs, cats, horses, elephants). In some embodiments, the subject has an oral disease or a symptom of oral disease. Exemplary oral diseases include gingivitis and dental caries. Exemplary symptoms of oral diseases include swollen gums; mouth sores; bright-red, or purple gums; shiny gums; swollen gums that emit pus; severe oral odor; gums that are painless; except when pressure is applied; gums that bleed easily, even with gentle brushing, and especially when flossing; gums that itch with varying degrees of severity; or toothache.

In some embodiments, the subject has oral diseases or conditions characterized by the presence of one or more of the bacteria described herein, e.g., *Streptococcus mutans, Streptococcus sanguis, Staphyococcus aureus* or drug resistant *Staphylococcus aureus* (MRSA), *Treponema denticola, Porphyromonas gingivalis, Aggregatibacter actinomycetemcomitans, Fusospirochetes, Veillonella*, and some forms of pathogenic *Lactobacilli, Actinomyces viscosus*, or *Nocardia* spp.

In some embodiments, the subject is at risk of having the oral diseases or conditions described herein.

Gingivitis

Compositions described herein can be used to treat or prevent gingivitis in a subject.

Gingivitis is a general term for gingival diseases affecting the gingiva (gums). Gingivitis can be defined as inflammation of the gingival tissue without loss of tooth attachment (i.e. periodontal ligament). Gingival inflammation can be induced by bacterial biofilms (also called plaque) adherent to tooth surfaces.

Gingivitis is usually caused by bacterial plaque that accumulates in the small gaps between the gums and the teeth and by calculus (tartar) that forms on the teeth. These accumulations may be tiny, even microscopic, but the bacteria in them produce foreign chemicals and toxins that cause inflammation of the gums around the teeth. This inflammation can cause deep pockets between the teeth and gums and loss of bone around teeth—an effect otherwise known as periodontitis. Pregnancy, uncontrolled diabetes mellitus and the onset of puberty increase the risk of gingivitis, due to hormonal changes that may increase the susceptibility of the gums or alter the composition of the dentogingival microflora. The risk of gingivitis is increased by misaligned teeth, the rough edges of fillings, and ill fitting or unclean dentures, bridges, and crowns, due to their plaque retentive properties. The drug phenytoin, birth control pills, and ingestion of heavy metals such as lead and bismuth may also cause gingivitis.

In some cases, the inflammation of the gingiva can suddenly amplify, such as to cause Acute Necrotizing Ulcerative Gingitivitis (ANUG). The etiology of ANUG is the overgrowth of a particular type of pathogenic bacteria (fusiform-spirochete variety) but risk factors such as stress, poor nutrition and a compromised immune system can exacerbate the infection. This results in the breath being extremely bad-smelling, and the gums feeling considerable pain and degeneration of the periodontium rapidly occurs. This can be treated with a 1-week course of Metronidazole antibiotic, followed by a deep cleaning of the gums by a dental hygienist or dentist and reduction of risk factors such as stress.

The symptoms of gingivitis include, e.g., swollen gums; mouth sores; bright-red, or purple gums; shiny gums; swollen gums that emit pus; severe oral odor; gums that are painless; except when pressure is applied; gums that bleed easily, even with gentle brushing, and especially when flossing; or gums that itch with varying degrees of severity.

Gingivitis can be treated or prevented using soluble polyglucosamines or derivatized polyglucosamines described herein in combination proper maintenance and/or with one or more of agents and/or therapeutics. For example, proper maintenance (varying from "regular cleanings" to periodontal maintenance or scaling and root planing) above and below the gum line, disrupts this plaque biofilm and removes plaque retentive calculus (tartar) to help remove the etiology of inflammation. The methods to prevent gingivitis include, e.g., regular oral hygiene that includes daily brushing and flossing; mouth wash using e.g., a saline solution or chlorhexidine; or rigorous plaque control programs along with periodontal scaling and curettage. In some embodiments, the administrations of a combination of agents and therapeutics are spaced sufficiently close together such that a synergistic effect is achieved.

Gingivitis can promote inflammation of the blood vessels, an important risk factor in inflammatory disorders in a subject, such as atherosclerosis and heart disease. People with gum disease are known, for instance, to have elevated levels of C-reactive protein (CRP), a marker for inflammation that is associated with an increased risk of coronary artery disease. It has also been shown that people with periodontal disease also have elevated levels of lipoprotein-associated phospholipase A2, another significant marker for inflammation that increases cardiac risk. Compositions described herein can be used to treat or prevent gingivitis-associated heart diseases or conditions in a subject.

Periodontitis

Compositions described herein can be used to treat or prevent periodontitis in a subject.

Periodontitis is a set of inflammatory diseases affecting the periodontium, i.e., the tissues that surround and support the teeth. Periodontitis involves the progressive loss of the alveolar bond around the teeth, and if left untreated can lead to the loosening and subsequent loss of teeth.

A diagnosis of periodontitis is established by inspecting the soft gum tissues around the teeth with a probe (e.g., a clinical examination) and by evaluating the patient's X-ray films (e.g., a radiographic examination), to determine the amount of bond loss around the teeth.

Periodontitis is caused by microorganisms that adhere to and grow on the tooth's surfaces, along with an overly aggressive immune response against these microorganisms.

Compositions described herein can be used in combination with one or more of agents and/or therapies to treat or prevent periodontitis in a subject. For example, periodontitis can be treated by e.g., nonsurgical scaling, debridement, root planing. Periodontal surgery may also be needed to stop progressive bond loss and regenerate lost bone by e.g., open flap debridement, osseous surgery, guided tissue regeneration, bone grafting. Periodontitis can be prevented by e.g., oral hygiene (e.g., proper brushing and flossing), dental sealants, or fluoride therapy. In some embodiments, the administrations of a combination of agents and therapeutics are spaced sufficiently close together such that a synergistic effect is achieved.

Dental Caries

Compositions described herein can be used to treat or prevent dental caries in a subject.

Dental caries, also known as tooth decay or cavity, is a disease where bacterial processes damage hard tooth structure (e.g., enamel, dentin and cementum). These tissues progressively break down, producing dental cavities (i.e., holes in the teeth). Bacteria associated with dental caries include, e.g., *Streptococcus mutans*.

The earliest sign of a new carious lesion is the appearance of a chalky white spot on the surface of the tooth, indicating an area of demineralization of enamel. This is referred to as incipient decay. As the lesion continues to demineralize, it can turn brown but will eventually turn into a cavitation. As the enamel and dentin are destroyed, the cavity becomes more noticeable. The affected areas of the tooth change color and become soft to the touch. Once the decay passes through enamel, the dentinal tubules, which have passages to the nerve of the tooth, can become exposed and cause the tooth to hurt. The pain may worsen with exposure to heat, cold, or sweet foods and drinks. Dental caries can also cause bad breath and foul tastes. In highly progressed cases, infection can spread from the tooth to the surrounding soft tissues. Complications of dental caries include, e.g., cavernous sinus thrombosis and Ludwig's angina.

Dental caries can be caused by infection of bacteria, e.g., *Streptococcus mutans, Streptococcus sanguis, Actinomyces viscosus*, and *Nocardia* spp. Other risk factors include, e.g., disorders or diseases affecting teeth (e.g., *Amelogenesis imperfecta*), the anatomy of teeth, fermentable carbohydrates, the frequency of which teeth are exposed to cariogenic (acidic) environments, reduced saliva (e.g., caused by medical conditions such as diabetes, or side effect of medications), or the use of tobacco.

Compositions described herein can be used in combination with one or more agents and/or therapies to treat or prevent dental caries in a subject. For example, dental caries can be treated by e.g., dental restoration or tooth extraction. Dental caries can be prevented by e.g., oral hygiene (e.g., proper brushing and flossing), dental sealants, or fluoride therapy. In some embodiments, the administrations of a combination of agents and therapeutics are spaced sufficiently close together such that a synergistic effect is achieved.

Dental Plaque

Compositions described herein can be used to treat (e.g., disrupt) or prevent dental plaque in a subject.

Dental plaque is biofilm (usually colorless) that builds up on the teeth. If not removed regularly, it can lead to dental cavities (caries) or periodontal problems (such as gingivitis).

The microorganisms that form the dental plaque include bacteria, e.g., *Streptococcus mutans* and anaerobes, with the composition varying by location in the mouth. Examples of such anaerobes include *Fusobacterium* and Actinobacteria. Those microorganisms close to the tooth surface can convert to anaerobic respiration and produce acids. Acids released from dental plaque lead to demineralization of the adjacent tooth surface, and consequently to dental caries. Saliva is also unable to penetrate the build-up of plaque and thus cannot act to neutralize the acid produced by the bacteria and remineralize the tooth surface. They also cause irritation of the gums around the teeth that could lead to gingivitis, periodontal disease and tooth loss. Plaque build-up can also become mineralized and form calculus (tartar).

Compositions described herein can be used in combination with one or more agents and therapies to treat or prevent dental plaque. For example, dental plaque can be prevented and removed by e.g., brushing thoroughly at least twice a day, with a fluoride toothpaste; using dental floss daily to remove plaque from between the teeth and under the gum line; checking teeth with plaque disclosing tablets to ensure removing tooth plaque; controlling diet (e.g., limiting sugary or starchy foods); and visiting dentist regularly for professional cleanings and dental examinations. In some embodiments, the administrations of a combination of agents and therapeutics are spaced sufficiently close together such that a synergistic effect is achieved.

Halitosis

Compositions described herein can be used to treat or prevent halitosis.

Halitosis, also known as; oral malodor, breath odor, mouth odor, foul breath, fege bosta, fetor oris, fetor ex ore, or bad breath are terms used to describe noticeably unpleasant odors exhaled in breathing. The origin of halitosis include, e.g., mouth, tongue, gum disease, nose, tonsils, stomach, or systemic diseases and specific sulfur-molecule generating bacteria such as *Solobacterium moorei*.

Compositions described herein can be used in combination with one or more of agents and therapies to treat or prevent halitosis. For example, treatment for halitosis include, e.g., gently cleaning the tongue surface, gargling, or maintaining oral hygiene. In some embodiments, the administrations of a combination of agents and therapeutics are spaced sufficiently close together such that a synergistic effect is achieved.

Oral Infection Treated by Antibacterials

The compositions and compounds described herein (e.g., soluble polyglucosamines or derivatized polyglucosamines) can be used alone or in combination with one or more antibiotics, to reduce bacteria in the mouth, or to treat or prevent an oral disease or condition, e.g., dental plaque, gingivitis, dental caries, or halitosis. General classes of antibiotics include, e.g., aminoglycosides, bacitracin, beta-lactam antibiotics, cephalosporins, chloramphenicol, glycopeptides, macrolides, lincosamides, penicillins, quinolones, rifampin, glycopeptide, tetracyclines, trimethoprim and sulfonamides. In some embodiments, the administrations of a combination of agents and therapeutics are spaced sufficiently close together such that a synergistic effect is achieved.

Exemplary antibiotics within the classes recited above are provided as follows. Exemplary aminoglycosides include Streptomycin, Neomycin, Framycetin, Parpmycin, Ribostamycin, Kanamycin, Amikacin, Dibekacin, Tobramycin, Hygromycin B, Spectinomycin, Gentamicin, Netilmicin, Sisomicin, Isepamicin, Verdamicin, Amikin, Garamycin, Kantrex, Netromycin, Nebcin, and Humatin. Exemplary carbacephems include Loracarbef (Lorabid). Exemplary carbapenems include Ertapenem, Invanz, Doripenem, Finibax, Imipenem/Cilastatin, Primaxin, Meropenem, and Merrem. Exemplary cephalosporins include Cefadroxil, Durisef, Cefazolin, Ancef, Cefalotin, Cefalothin, Keflin, Cefalexin, Keflex, Cefaclor, Ceclor, Cefamandole, Mandole, Cefoxitin, Mefoxin, Cefprozill, Cefzil, Cefuroxime, Ceftin, Zinnat, Cefixime, Suprax, Cefdinir, Omnicef, Cefditoren, Spectracef, Cefoperazone, Cefobid, Cefotaxime, Claforan, Cefpodoxime, Fortaz, Ceftibuten, Cedax, Ceftizoxime, Ceftriaxone, Rocephin, Cefepime, Maxipime, and Ceftrobriprole. Exemplary glycopeptides include Dalbavancin, Oritavancin, Teicoplanin, Vancomycin, and Vancocin. Exemplary macrolides include Azithromycin, Sithromax, Sumamed, Zitrocin, Clarithromycin, Biaxin, Dirithromycin, Erythromycin, Erythocin, Erythroped, Roxithromycin, Troleandomycin, Telithromycin, Ketek, and Spectinomycin. Exemplary monobactams include Aztreonam. Exemplary penicillins include Amoxicillin, Novamox, Aoxil, Ampicillin, Azlocillin, Carbenicillin, Coxacillin, Diloxacillin, Flucloxacillin Floxapen, Mezlocillin, Methicillin, Nafcillin, Oxacillin, Penicillin, and Ticarcillin. Exemplary polypeptides include Bacitracin, Colistin, and Polymyxin B. Exemplary quinolones include Ciprofloxacin, Cipro, Ciproxin, Ciprobay, Enoxacin, Gatifloxacin, Tequin, Levofloxacin, Levaquin, Lomefloxacin, Moxifloxacin, Avelox, Norfloxacin, Noroxin, Ofloxacin, Ocuflox, Trovafloxacin, and Trovan. Exemplary sulfonamides include Mefenide, Prontosil (archaic), Sulfacetamide, Sulfamethizole, Sulfanilamide (archaic), Sulfasalazine, Sulfisoxazole, Trimethoprim, Trimethoprim-Sulfamethoxazole (co-trimoxazole), and Bactrim. Exemplary tetracyclines include Demeclocyline, Doxycycline, Vibramycin, Minocycline, Minocin, Oxytetracycline, Terracin, Tetracycline, and Sumycin. Other exemplary antibiotics include Salvarsan, Chloamphenicol, Chloromycetin, Clindamycin, Cleocin, Linomycin, Ethambutol, Fosfomycin, Fusidic Acid, Fucidin, Furazolidone, Isoniazid, Linezolid, Zyvox, Metronidazole, Flagyl, Mupirocin, Bactroban, Nitrofurantion, Macrodantin, Macrobid, Platensimycin, Pyrazinamide, Quinupristin/Dalfopristin (Syncerid), Rifampin (rifampicin), and Tinidazole. In some embodiments, the exemplary antibiotics include xylitol, hydrogen peroxide, chlorhexidine, delmopinol, decapinol, hopchlorite, chlorine dioxide and cetylpyridinium chloride.

Oral Inflammation Treated by Anti-Inflammatories

The compositions and compounds described herein (e.g., soluble polyglucosamines and derivatized polyglucosamines) can be used alone or in combination with one or more anti-inflammatory drugs, e.g., steroidal anti-inflammatory drugs and non-steroidal anti-inflammatory drugs (NSAIDs), to reduce bacteria in the mouth, or to treat or prevent an oral disease or condition, e.g., dental plaque, gingivitis, dental caries, or halitosis. In some embodiments, the administrations of a combination of agents and therapeutics are spaced sufficiently close together such that a synergistic effect is achieved.

Exemplary steroidal anti-inflammatory drugs include glucocorticoids (corticosteroids), e.g., Hydrocortisone (Cortisol), Cortisone acetate, Prednisone, Prednisolone, Methylprednisolone, Dexamethasone, Betamethasone, Triamcinolone, Beclometasone, Fludrocortisone acetate, Deoxycorticosterone acetate (DOCA), and Aldosterone. Exemplary non-steroidal anti-inflammatory drugs include Aspirin, Choline and magnesium salicylates, Choline salicylate, Celecoxib, Diclofenac potassium, Diclofenac sodium, Diclofenac sodium with misoprostol, Diflunisal, Etodolac, Fenoprofen calcium, Flurbiprofen, Ibuprofen, Indomethacin, Ketoprofen, Magnesium salicylate, Meclofenamate sodium, Mefenamic acid, Meloxicam, Nabumetone, Naproxen, Naproxen sodium, Oxaprozin, Piroxicam, Rofecoxib, Salsalate, Sodium salicylate, Sulindac, Tolmetin sodium, and Valdecoxib. Examples of non-steroidal anti-inflammatory agents (e.g., peptides) include regulatory cytokines such as interleukins, e.g., IL-1, IL-4, IL-6, IL-10, IL-11, and IL-13.

Dry Mouth

The compositions and compounds described herein (e.g., soluble polyglucosamines and derivatized polyglucosamines) can be used alone or in combination of one or more agents (e.g., moisturizing agents), to reduce dry mouth (also referred to as xerostomia). In some embodiments, the compositions and compounds described herein (e.g., soluble polyglucosamines and derivatized polyglucosamines) can be used alone or in combination with one or more agents (e.g., moisturizing agents), to reduce (e.g., prevent) the symptoms of dryness of the mouth.

Dry mouth, or dry mouth syndrome or xerostomia, refers generally to the subjective symptom of dryness in the mouth (or oral dryness), which can e.g., change or result from change in the composition of saliva; or reduce or result from reduction of salivary flow (e.g., hyposalivation). Dry mouth can e.g., interfere with eating, talking, sleeping, and/or general comfort.

Dry mouth can be caused by certain drugs (e.g., in the elderly, e.g., the elderly who take several medications, have reduced salivary flow), by dehydration, chemotherapy, radiotherapy (e.g., involving the salivary glands), and other diseases (e.g., Sjogren's disease); and be present in persons who breathe through their mouths (e.g., mouthbreathing). Dry mouth may also have no identified cause, and/or result from a psychogenic reason.

Exemplary signs and symptoms of dry mouth are provided as follows. Dental caries (xerostomia related caries), e.g., tooth decay that progresses more aggressively than it would in a subject without dry mouth; ascending (suppurative) sialadenitis, an infection of the major salivary glands (usually the parotid gland) that may be recurrent; dysgeusia, an altered taste sensation (e.g., a metallic taste) and dysosmia, altered sense of smell; intraoral halitosis (bad breath); oral dysesthesia, a burning or tingling sensation in the mouth; mucosa that appears dry; dysphagia, or difficulty swallowing and chewing, especially when eating dry foods; fissured tongue with atrophy of the filiform papillae and a lobulated, erythematous appearance of the tongue; difficulty wearing dentures; mouth soreness and oral mucositis; dry, sore, and cracked lips and angles of mouth; and/or thirst.

TABLE 1. Comparison of S. mutans biofilms grown for 72 hours treated twice daily for 2 minutes to evaluate biofilm reduction between oral rinse products and active ingredients.

Figure 7:
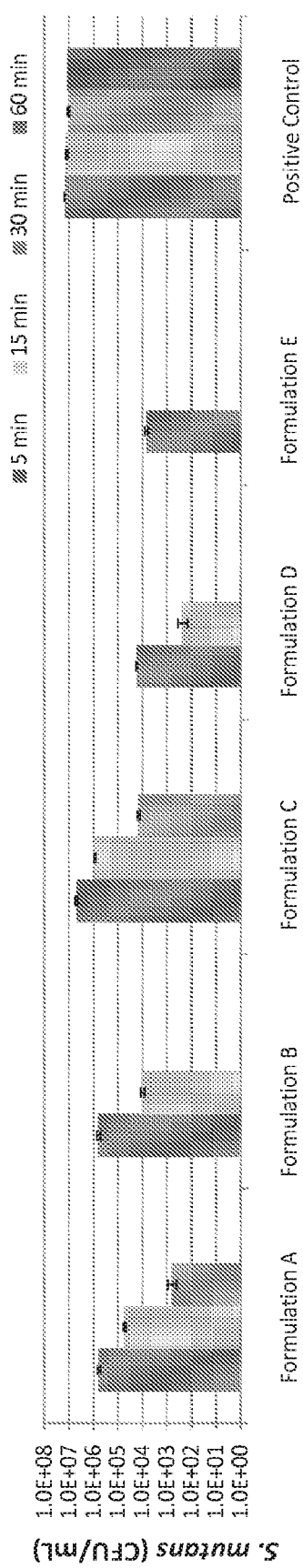
FIG. 7. Exemplary comparison of antibacterial activity of formulations containing PAAG, xylitol, sorbitol, polysorbate 20, peppermint oil, sodium fluoride, and sodium bicarbonate after 5, 15, 30, or 60 minutes against S. mutans.
Figure 8:
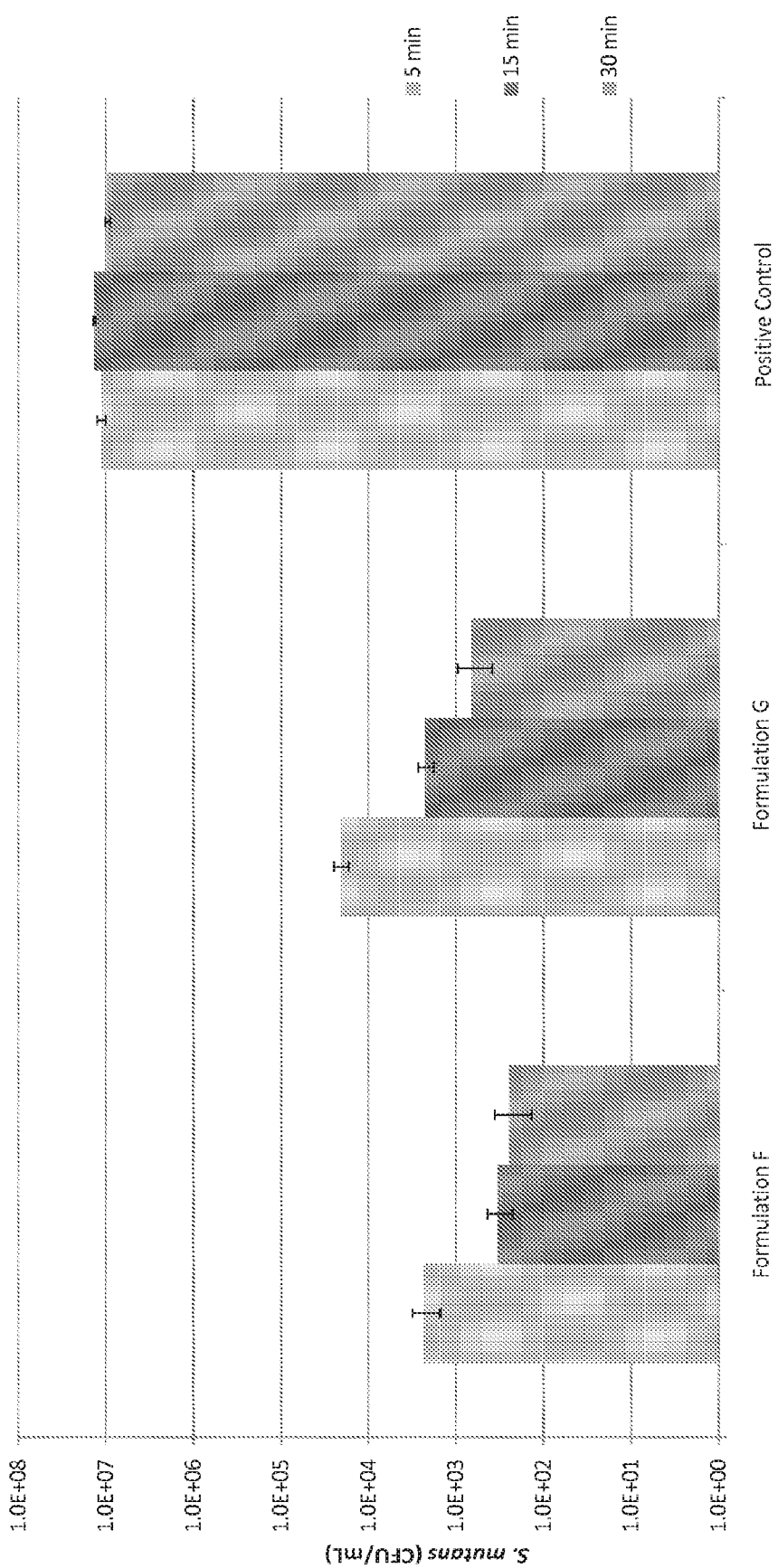
FIG. 8. Exemplary comparison of antibacterial activity of formulations containing PAAG, xylitol, sorbitol, polysorbate 20, sodium fluoride, benzoic acid, and peppermint oil, with and without glycerin, after a 5, 15, or 30-minute treatment, against S. mutans.

TABLE 2. Composition of different oral rinse formulations tested and described in Examples 7 and 8 (FIGS. 7 and 8).

TABLE 3. Exemplary combinations of PAAG and xylitol demonstrating synergy.

TABLE 4. Exemplary combinations of PAAG and xylitol demonstrating synergy.

EXAMPLES

In vitro models were used in comparing PAAG to common oral rinses and other active ingredients provide an indication of clinical activity and tolerance. PAAG was shown to aggregate oral pathogens and bacteria associated with malodor and caries.

These studies included a comparison of the biofilm (plaque) removing activity of five oral rinse formulations and active ingredients, including PAAG oral rinse against Streptococcus mutans biofilms. Treatment with PAAG oral rinse reduced oral biofilms as well as comparable products did. In contrast, epithelial cell viability was significantly preserved following treatment with PAAG compared to competing products and active ingredients. Furthermore, an unexpected synergistic effect of the oral rinse components with PAAG was demonstrated. The advantageous effect of the combination of xylitol, sorbitol, peppermint oil, sodium fluoride and glycerin was observed through significant reductions in the effective PAAG concentrations needed to achieve reductions in bacterial load.

Unless otherwise indicated, all percentages and ratios used are by weight of a component used per volume of total composition. Also, unless otherwise indicated, PAAG as used in the Examples below is 18-30% functionalized, 20-150 kDa PAAG.

Example 1: PAAG Aggregation Study of Planktonic Oral Bacteria

Figure 1:
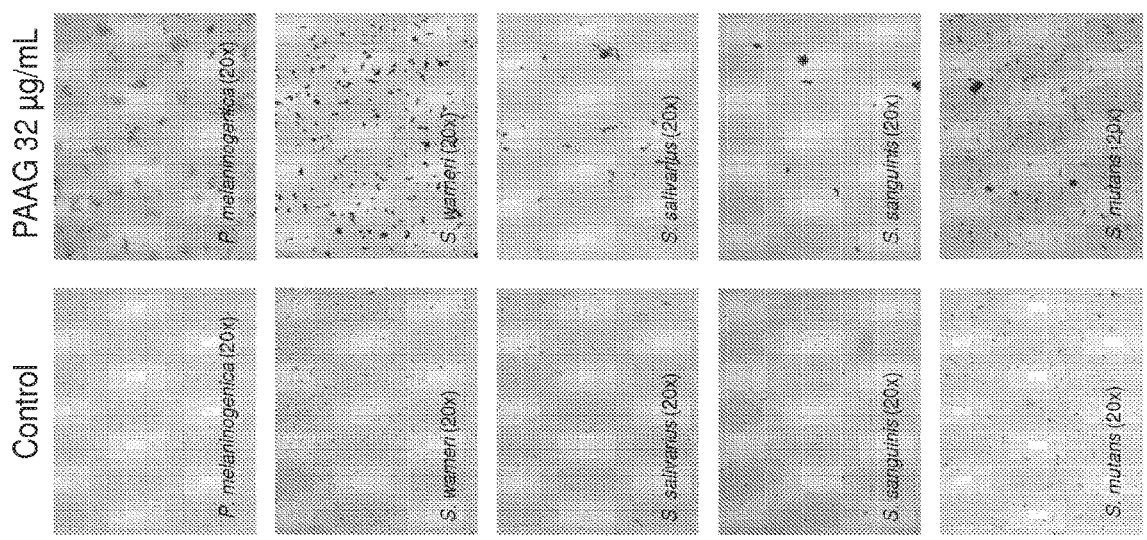
FIG. 1. Exemplary study shows that PAAG aggregates oral bacteria including those associated with disease and malodor.

Protocol:

Light microscopy was used to show aggregation of oral bacteria treated with PAAG. *Streptococcus mutans* ATCC 35668, *Staphylococcus warneri* ATCC 49454, *Streptococcus salivarius*, and *Streptococcus sanguinis* were grown in Brain-Heart Infusion (BHI) media anaerobically overnight at 37° C. *Prevotella melaninogeni* ATCC 25845 was grown in Chopped Meat Media (CMM) anaerobically for 72 hours at 37° C. Each strain was resuspended at approximately $10^8$ CFU/mL. PAAG (30% functionalized, 86 kDa) was applied at concentrations of 32 μg/mL for 2 minutes, stained with 0.4% crystal violet, and observed for clumping with a light microscope. Representative images are shown (FIG. 1).

Results:

PAAG maintains the ability to aggregate oral bacteria at relatively low concentrations found in the oral rinse formulation (32 µg/mL) at physiologic pH. Specifically, FIG. 1 shows *Prevotella melaninogenica, Staphylococcus warneri, Streptococcus salivarius, Streptococcus sanguinis*, and *Streptococcus mutans* are aggregated by 32 µg/mL PAAG after 2 minutes of treatment (right panels) compared to untreated controls (left panels).

Example 2: Reduction of Oral Biofilms by PAAG

Figure 2:
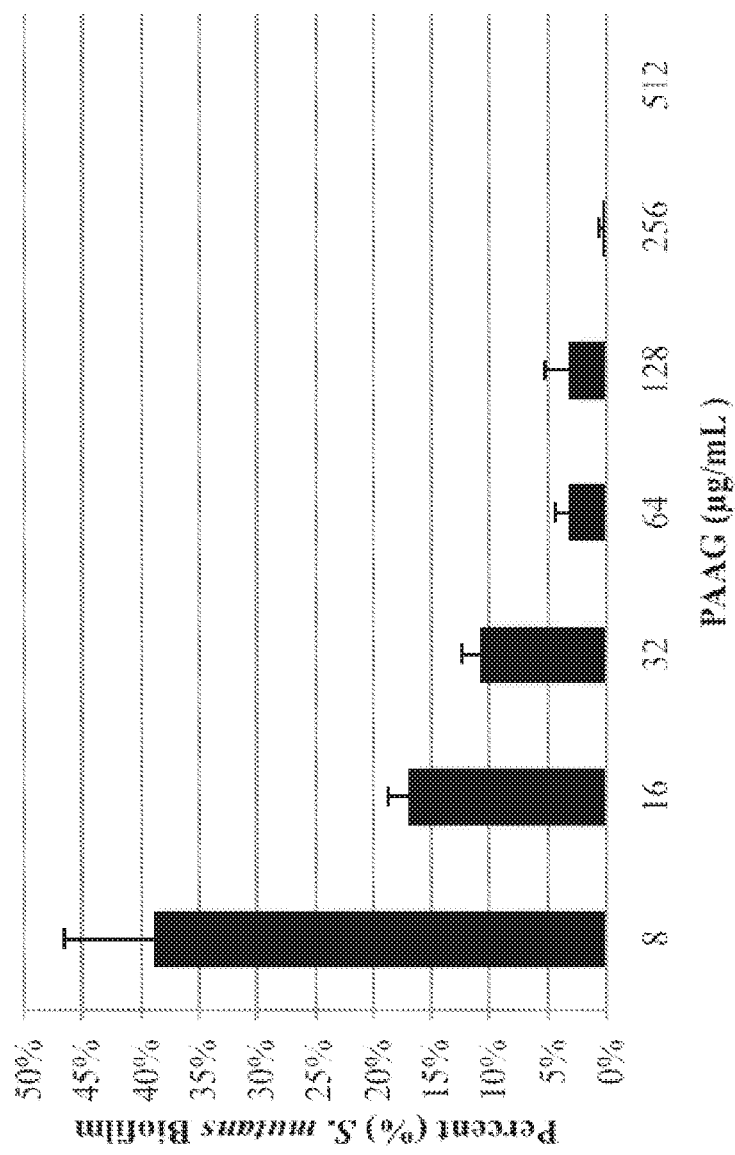
FIG. 2. Exemplary dose response of S. mutans biofilms treated with 8 to 512 μg/mL PAAG for 1 hour to evaluate biofilm reduction via CFU.
Figure 3:
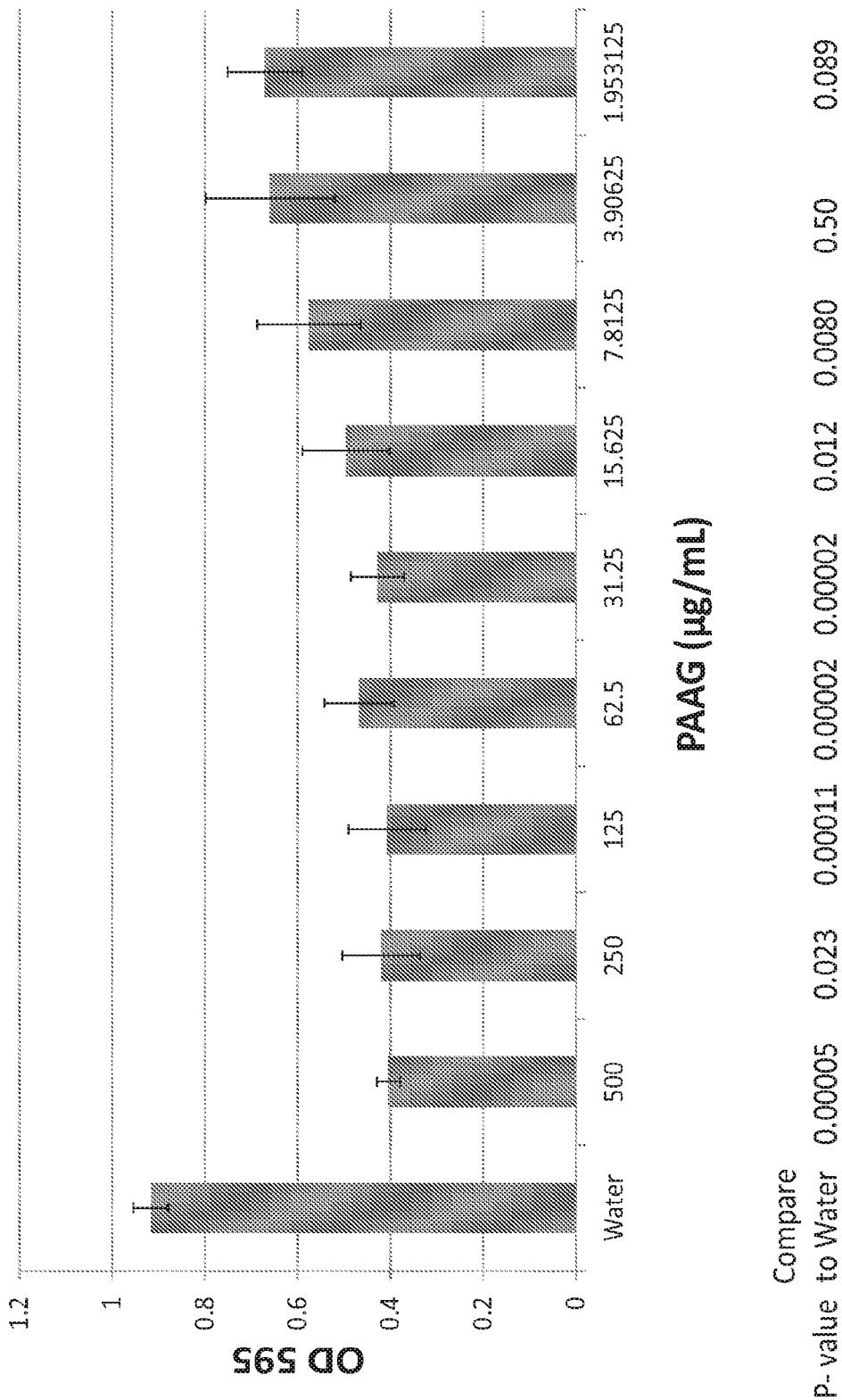
FIG. 3. Exemplary dose response of PAAG against S. mutans biofilms for biomass reduction.

Protocol:

Biofilms of *S. mutans* ATCC 35668 were grown on hydroxyapatite-coated pegs according to Minimum Biofilm Eradication Concentration (MBEC) Assay™ (Innovotech, Alberta, Canada) methods in BHI media supplemented with 1% sucrose anaerobically for 72 hours at 37° C. Biofilm reduction was analyzed using previously established methods against mature *S. mutans* biofilms (Harrison et al., 2005). For dose response studies that measured biofilm reduction based on colony forming unit (CFU) reduction, biofilms were treated with PAAG (30% functionalized, 86 kDa) from 8 to 512 µg/mL for 1 hour. The percent (%) biofilm remaining and standard error compared to water treated control was quantified via viable plate counts. A representative assay of two independent experiments is shown (FIG. 2). For dose response studies that measured biofilm biomass reduction, biofilms were treated with PAAG (30% functionalized, 86 kD) concentrations between 1.2 to 500 µg/mL for 1 hour. The biofilms were rinsed in PBS, and placed into 200 µl 95% ethanol each for 2 minutes to fix the biofilms. The MBEC-HTP biofilms were stained with 150 µl of 3% Crystal Violet dye each for 2 minutes, and rinsed five times with PBS. The remaining dye was solubilized via treatment with 150 µl of 95% ethanol for 1 minute. An aliquot (100 µl) of each sample was placed in a 96-well plate and the OD595 was measured (FIG. 3).

Results:

An exemplary dose response study examined the ability of PAAG to remove 72-hour *S. mutans* biofilms grown on hydroxyapatite-coated pegs after 1-hour treatment, and is shown in FIG. 2. The CFU remaining on the peg biofilm were enumerated to evaluate the remaining bacteria associated with the biofilm. The data show that the ability of PAAG to remove *S. mutans* biofilms may be dose dependent. Greater than 99% of *S. mutans* biofilm was removed when treated with 214 µg/mL of PAAG for 1 hour compared to water control. When *S. mutans* biofilms were treated with 32 µg/mL PAAG, the dose in the PAAG oral rinse, approximately 90% reduction was observed after 1-hour treatment (FIG. 2). The biomass measurements suggest a PAAG dose of 7.8 µg/mL was enough to cause a significant reduction in biofilm biomass compared to water control (p=0.008). The biomass was reduced significantly in 1 hour by all the higher doses (boxed are statistically significant values) however, no further dose response was observed beyond treatment with 31.25 µg/mL with a treatment of this frequency and duration. (FIG. 3).

Example 3: Comparative Biofilm Reduction Study of PAAG, Alone or in Combination with Other Ingredients, and Commercially Available Oral Rinses Protocol:

For comparative studies, biofilms were placed into a 96-well plate with PAAG oral rinse formulation ("Oral Formulation H"), other commercially available oral products (Biotene, Corsodyl, Peroxyl, or Listerine), and 32 µg/mL PAAG (30% functionalized, 86 kDa) and other active ingredients; 0.029% lactoferrin (Europharma Concepts, Clara, Co. Offaly, Ireland), 0.2% chlorhexidine gluconate (Spectrum Chemical Mfg. Co., Gardena, Calif., USA) 1.5% hydrogen peroxide, or 20% alcohol (Macron Chemicals, Center Valley, Pa., USA). PAAG Oral Formulation H contains sorbitol (17.5%), glycerin (10%), xylitol (2.5%), polysorbate 20 (1.5%), peppermint oil (0.2%), benzoic acid (0.3%), sodium fluoride (0.5%), and 23% functionalized, 37 kDa PAAG (0.0032%). Biofilms of *S. mutans* were grown on hydroxyapatite-coated pegs according to MBEC Assay™ methods for 72 hours, and then treated with the oral rinses or a water control. The corresponding active ingredients were also evaluated. The biofilms were exposed for 2-minutes, twice in a 6-hour interval to evaluate biofilm removal. Following treatment, biofilms were rinsed, fixed, and stained with 0.4% Crystal Violet, and remaining biofilm was quantitated via CFU or OD595 (Beenken and Smeltzer, 2003). Biofilms were analyzed in triplicate in at least 3 independent assays. Ratios were averaged from all assays and the percent biofilm reduced and standard error compared to water control is shown.

Results:

An exemplary percentage of biofilm biomass removed by each oral rinse compared to water is shown in TABLE 1. Following a two-minute treatment, twice daily PAAG Oral Formulation H (32.3±3.4%) was able to reduce more *S. mutans* biofilm than Corsodyl (18.9±4.5% biofilm reduction) and was as effective as Peroyl (32.4±4.7%) and Biotene (29.3±3.4%) containing hydrogen peroxide and lactoferrin as the active ingredients, respectively. Listerine was able to remove the most biofilm in the group (41.7±3.7%). Active ingredients assumed the same pattern in that alcohol (39.9±3.9%) and 1.5% hydrogen peroxide (36.9±3.8%) removed the most biofilm, while 0.0032% PAAG (27.7±2.8%) and 0.29% lactoferrin (25.6±4.3%) had similar activity. Chlorhexidine gluconate was the least effective (17.1±4.5%).

Example 4: Oral Rinse Comparative Epithelial Cell Viability Studies

Protocol:

Human epithelial cell monolayers of A431 (ATCC CRL-1555) were seeded in tissue culture treated 96-well plates at a density of $2 \times 10^4$ cells/well in DMEM media supplemented with 10% FBS, 1% Penicillin-Streptomycin, and 1% Amphotericin B. Seeded cells were incubated at 37° C. with 5% $CO_2$ for 48 hours. The media was removed and replaced with serum-free, antimicrobial-free media and rinsed one time for 30 seconds with PAAG Oral Formulation H, other oral products (Biotene, Corsodyl, Peroxyl, or Listerine), 32 µg/mL PAAG (30% functionalized, 86 kDa) and other active ingredients (0.029% lactoferrin, 0.2% chlorhexidine gluconate, 1.5% hydrogen peroxide, or 20% alcohol). Epithelial cell viability was determined by ATPLite Luminescence ATP Detection Assay System (PerkinElmer). Testing was done in duplicate.

Figure 4:
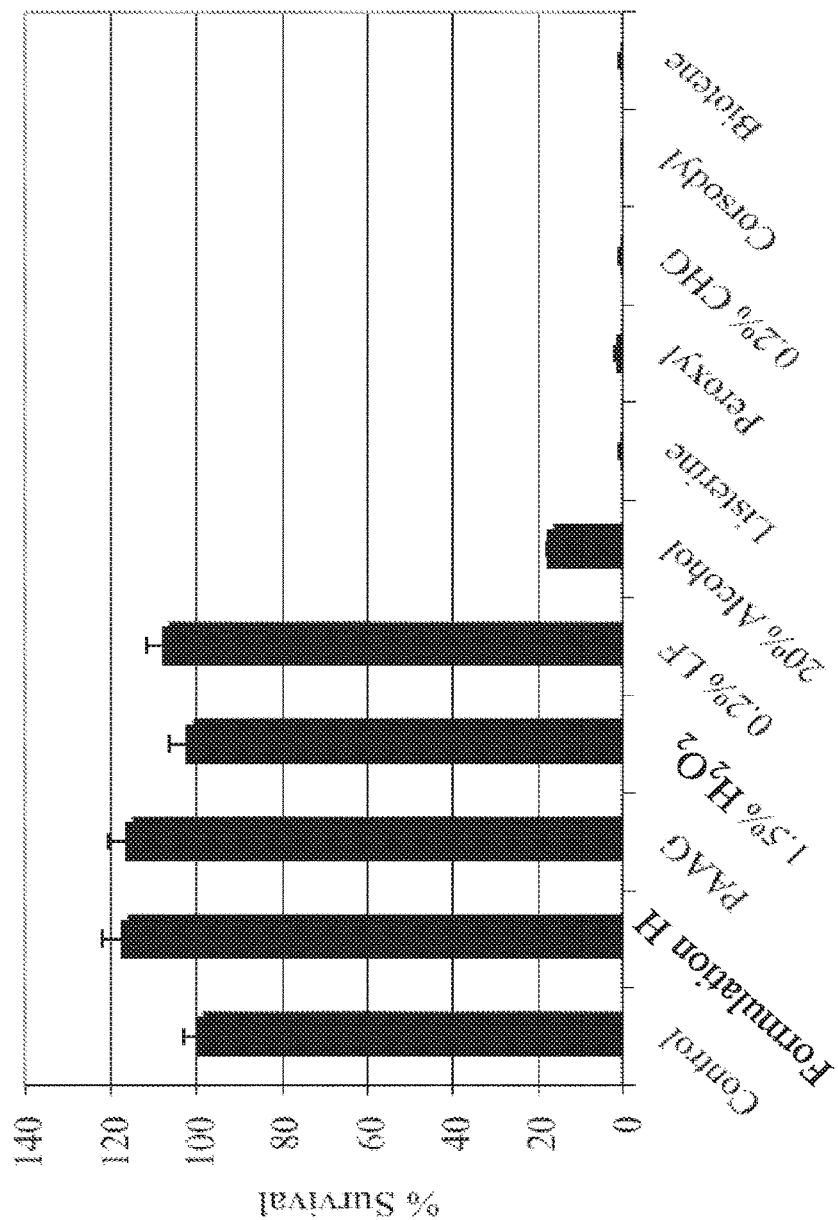
FIG. 4. The percent of A431 epithelial cell survival compared to media rinse control following 30 second exposure to oral rinses and corresponding active ingredients.

Results:

Epithelial cell viability was compared between PAAG and other oral active ingredients and oral rinse products. Human epithelial cell monolayers were rinsed once for 30 seconds with each treatment. Following treatment, the epithelial cells were evaluated with ATP LITE Luminecence assay that measured viability via ATP. The data was normalized to untreated cells to compare percent survival (FIG. 4). Compared to other oral rinse products, PAAG was the least cytotoxic to epithelial cells. PAAG was well tolerated compared to 20% alcohol and 0.2% chlorhexidine gluconate, common oral rinse active ingredients (FIG. 4). The cells were rinsed once with PAAG Oral Formulation H, other oral rinse products (Biotene, Corsodyl, Peroxyl, or Listerine), oral products active ingredients (0.0032% PAAG, 0.029% lactoferrin (LF), 0.2% chlorhexidine (CHG), 1.5% hydrogen peroxide, or 20% alcohol). PAAG Oral Formulation H contains sorbitol (17.5%), glycerin (10%), xylitol (2.5%), polysorbate 20 (1.5%), peppermint oil (0.2%), benzoic acid (0.3%), sodium fluoride (0.5%), and PAAG (0.0032%). Epithelial cell viability was determined by ATPLite Luminescence ATP Detection Assay System (Perkin Elmer) and compared to media rinsed cells. FIG. 4 shows that PAAG Oral Formulation H, 0.0032% PAAG, 1.5% hydrogen peroxide, and 0.2% lactoferrin maintain epithelial cell viability, while all other rinse treatments result in less than 20% viable cells remaining Example 5: Antibacterial Activity of Oral Rinse Components Separately and in Combination Protocol:

Antibacterial tests evaluated components of oral rinse in vitro for the ability to kill S. mutans. S. mutans was grown in Todd Hewitt broth overnight at 37° C. and resuspended in PAAG Oral Formulation (containing 32 µg/mL 23% functionalized, 37 kDa PAAG, 15% xylitol, 1.5% polysorbate 20, 1.5% peppermint oil) or individual ingredients at a concentration of about $10^6$ CFU/ml. The bacteria were treated with each oral rinse formulation for 1 or 2 hours, then resuspended in PBS, vortexed and sonicated for 10 minutes to break up aggregated bacteria. Aliquots were serially diluted and plated onto BHI agar to quantify growth via viable plate counts.

Figure 5:
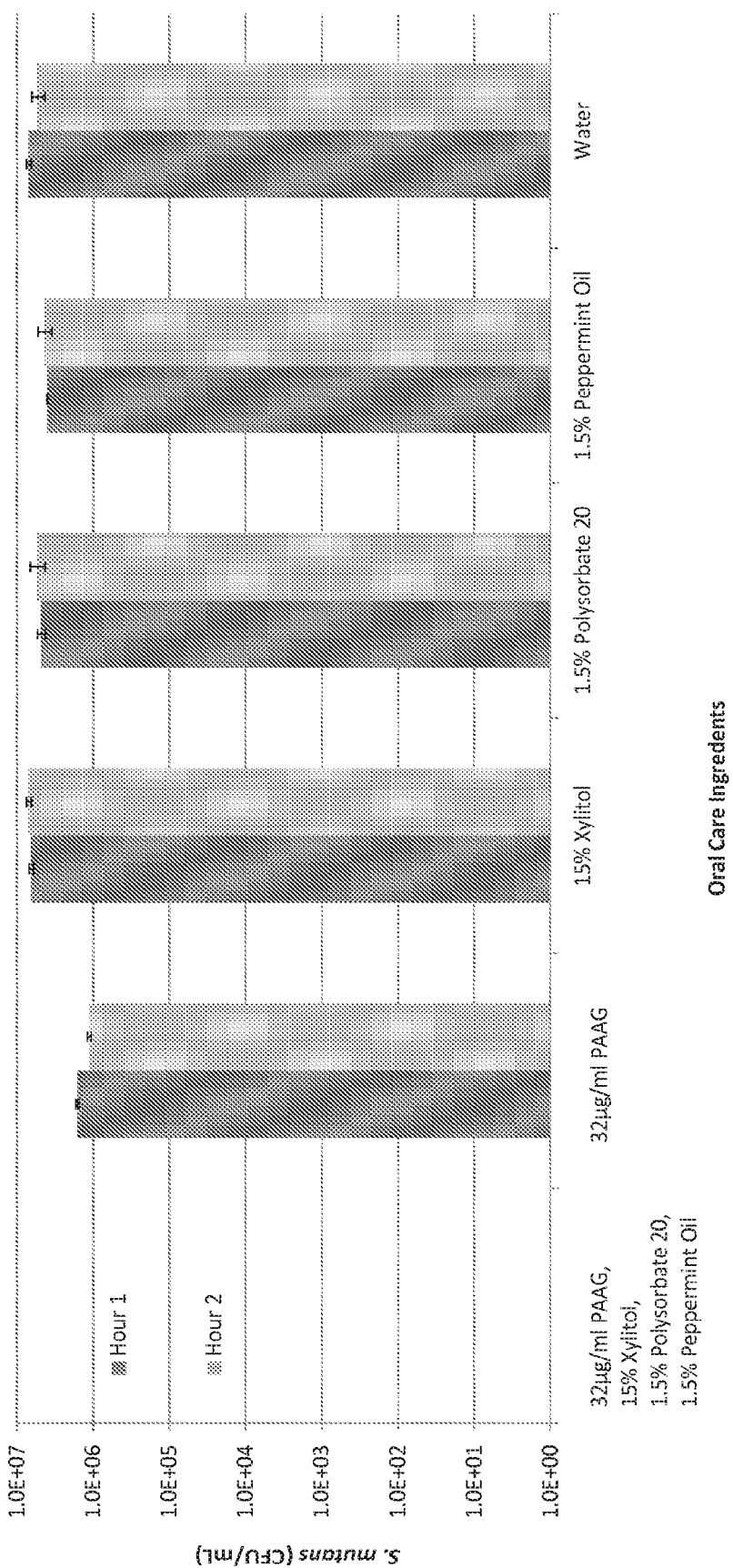
FIG. 5. Exemplary antibacterial activity of oral rinse components PAAG, xylitol, polysorbate 20, peppermint oil, and water, separately and in combination, after a 1 or 2 hour treatment with S. mutans.

Results:

The exemplary data shows that the components selected are synergistic. FIG. 5 illustrates that while the individual components independently have little antibacterial activity, the combination of PAAG and xylitol, polysorbate 20 and peppermint oil together is significantly more antibacterial.

Example 6: Antibacterial Activity of PAAG with Non-Fermentable Sugars

Protocol:

Antibacterial tests evaluated PAAG with non-fermentable sugars in vitro for the ability to kill S. aureus (MRSA MW-2). S. aureus was grown in Todd Hewitt broth overnight at 37° C. and resuspended in water at a concentration of about $10^6$ CFU/ml. The bacteria were treated with either xylitol or sorbitol solution at concentrations between 1-25% (w/v) with and without 200 ppm PAAG (28% functionalized, 37 kDa) for 1-hour. The bacteria were then resuspended in PBS, serially diluted and plated onto BHI agar to quantify growth via viable plate counts.

Figure 6:
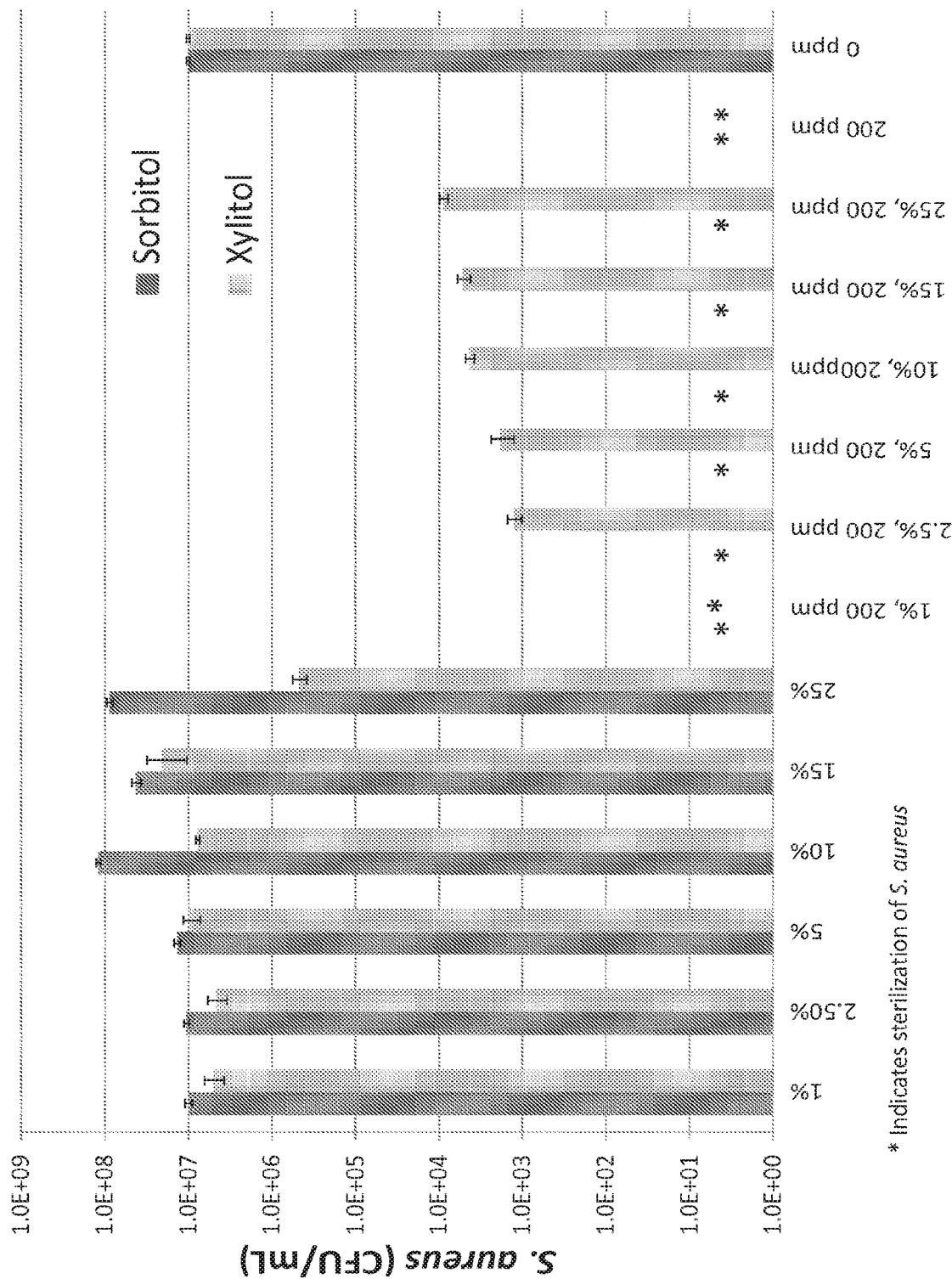
FIG. 6. Exemplary comparison of antibacterial activity of 200 ppm PAAG with and without 1-25% of a 70% (w/v) sorbitol solution or xylitol against S. aureus.

Results:

Exemplary data presented in FIG. 6 shows exemplary antibacterial activity of sorbitol or xylitol, with and without 200 ppm PAAG. Antibacterial activity was maintained when sorbitol was added to 200 ppm PAAG. Xylitol interferes with the antibacterial activity in a dose dependent manner when used with PAAG at 200 ppm against S. aureus suggesting lower concentrations may demonstrate synergy. * indicates that there are no CFU's remaining.

Example 7: Synergy of Antibacterial Activity of PAAG with Non-Fermentable Sugars and Other Components Protocol:

Antibacterial tests evaluated components of oral rinse in vitro for the ability to kill S. mutans. S. mutans was grown in Todd Hewitt broth overnight at 37° C. and resuspended in PAAG Oral Formulations (containing 23% functionalized, 37 kDa PAAG or 30% functionalized, 86 kDa PAAG) and components as listed on TABLE 2 at a concentration of about $10^6$ CFU/ml. The bacteria were treated with each oral rinse formulation for 5, 15, 30, or 60 minutes, then resuspended in PBS, vortexed and sonicated for 10 minutes to break up aggregated bacteria. Aliquots were serially diluted and plated onto BHI agar to quantify growth via viable plate counts.

Results:

Exemplary data presented in FIG. 7 shows that PAAG used in combination with sorbitol, xylitol or peppermint oil may be more antibacterial than PAAG used alone. Polysorbate 20 was used to emulsify the peppermint oil. Formulations A through E were tested to show optimal antibacterial activity of specific components of the formulation. Formulation A demonstrated interference of antibacterial activity by sodium bicarbonate. Formulation B showed excellent antibacterial activity within 30 minutes with 10% xylitol and sodium fluoride. Formulations C, D, and E further suggest a synergistic relationship between non-digestible sugars xylitol and sorbitol, peppermint oil and sodium fluoride. Formulations C and D showed excellent antibacterial activity within 30 minutes with 17.5% sorbitol, and that sodium fluoride does not interfere with the antibacterial activity. Formulation E (with 0.5% peppermint oil) showed that the peppermint oil concentration can be lowered and antibacterial activity may be maintained, illustrating that unexpected synergy may be observed even after a 15-minute treatment (when comparing Formulation E (with 0.5% peppermint oil) with Formulation D (with 1% peppermint oil)).

Example 8: Comparison of Antibacterial Activity of Oral Rinse Formulations Demonstrates Synergy of PAAG with Glycerin Protocol:

Antibacterial tests evaluated components of oral rinse in vitro for the ability to kill S. mutans. S. mutans was grown in Todd Hewitt broth overnight at 37° C. and resuspended in PAAG Oral Formulations (containing 23% functionalized, 37 kDa PAAG) and components as listed on TABLE 2 at a concentration of about $10^6$ CFU/ml. The bacteria were treated with each oral rinse formulation for 5, 15, or 30 minutes, then resuspended in PBS, vortexed and sonicated for 10 minutes to break up aggregated bacteria. Aliquots were serially diluted and plated onto BHI agar to quantify growth via viable plate counts.

Results:

Exemplary data illustrated in FIG. 8 shows that glycerin has a synergistic effect with PAAG. Formulations F and G were tested to optimize the amount of specific components of the formulation. Formulation F compared to control shows excellent antibacterial activity within 5 minutes. Further, when compared to Formulation G (without glycerin), Formulation F (with 10% glycerin) was more effective.

Example 9: Comparison of the Anti-Biofilm Activity of the Active Ingredients of the Oral Formulation Protocol:

The *S. mutans* biofilms were grown according to MBEC™ for High-throughput Screening methods (Innovotech) on a hydroxyapatite-coated peg lid placed in trough containing BHI media supplemented with 1% sucrose rocking for 72 hours. The pegs were treated twice daily with PAAG (30% functionalized, 86 kD) active ingredients (FIG. 9) at 8-hour intervals for 2-minutes. The biofilms were rinsed in PBS, and the pegs were removed and placed into 200 µl 95% ethanol each for 2 minutes to fix the biofilms. The MBEC-HTP biofilms were stained with 150 µl of 3% Crystal Violet dye each for 2 minutes, and rinsed five times with PBS. It was noted that chlorhexidine appears to "fix" the biofilm to the pegs. The bacteria may or may not be viable because OD measured biofilm biomass, not viable CFUs. The stained and rinsed MBEC-HTP biofilms were then placed in 150 µL ethanol for 1-minute to remove the dye/biofilm. Then 100 µL of the ethanol and dyed biofilm suspension was placed into a 96-well plate and the OD595 was measured to quantify the remaining stained biofilm biomass.

Figure 9:
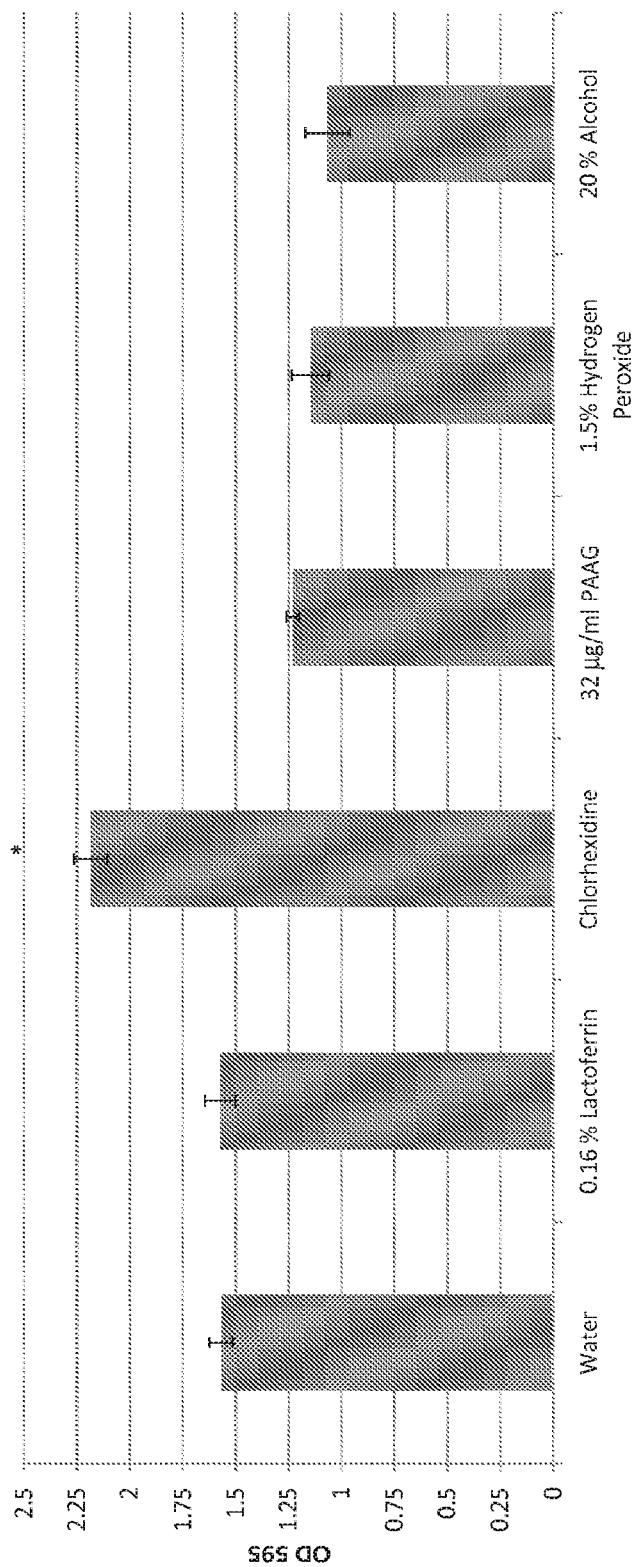
FIG. 9. Exemplary MBEC peg biofilm biomass reduction assay of PAAG compared to other oral rinse active ingredients.

Results:

Exemplary data shown in FIG. 9 indicates that a significant reduction in *S. mutans* biofilm biomass occurs when treated with 32 µg/mL PAAG ($p=0002$), similar to treatment with 1.5% hydrogen peroxide ($p=0012$) or alcohol ($p=0009$). P values are compared to water control. The treatment is similar to the expected patient use. Lactoferrin and chlorhexidine at this frequency and dose condition did not significantly reduce *S. mutans* biofilm biomass compared to water control.

Example 10: Comparative Oral Formulation Biofilm Biomass Reducing Activity

Protocol:

The *S. mutans* biofilms were grown according to MBEC™ for High-throughput Screening methods (Innovotech, Edmonton, AB Canada) on a hydroxyapatite coated peg lid placed in trough containing BHI media supplemented with 1% sucrose rocking for 72 hours. The pegs were treated for 1-hour or twice in one day for 2 minutes each treatment with an 8-hour interval in between. The biofilms were rinsed in PBS, and then the pegs were removed and placed into 200 µl 95% ethanol each for 2 minutes to fix the biofilms. The pegs were then stained with 150 µl of 3% Crystal Violet dye each for 2 minutes then rinsed five times with PBS. 100 µL of the ethanol and dyed biofilm suspension was then placed into a 96-well plate and the OD595 was measured to quantify the remaining stained biofilm biomass.

Formulations F (PAAG 37 kDa, 23% functionalized) and H (PAAG 86 kDa, 30% functionalized) contain the complete oral rinse formulation ingredients: 17.5% sorbitol, 10% glycerin, 1.5% Polysorbate 20, 0.2% Peppermint oil, 2.5% xylitol, 0.3% benzoic acid, 0.05% sodium fluoride, 0.0032% PAAG.

Figure 10:
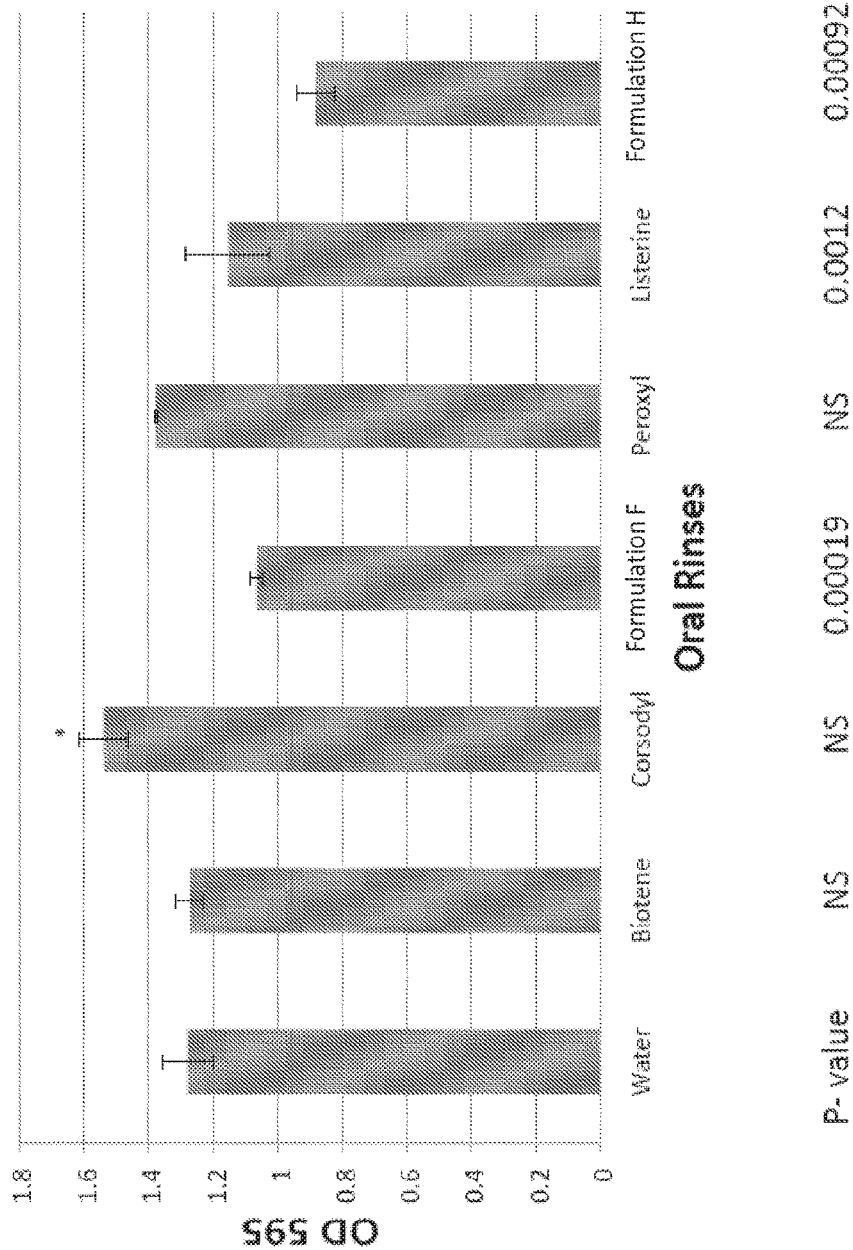
FIG. 10. Exemplary MBEC peg biofilm biomass reduction assay of PAAG-based oral rinse compared to other products (1-hour treatment).
Figure 11:
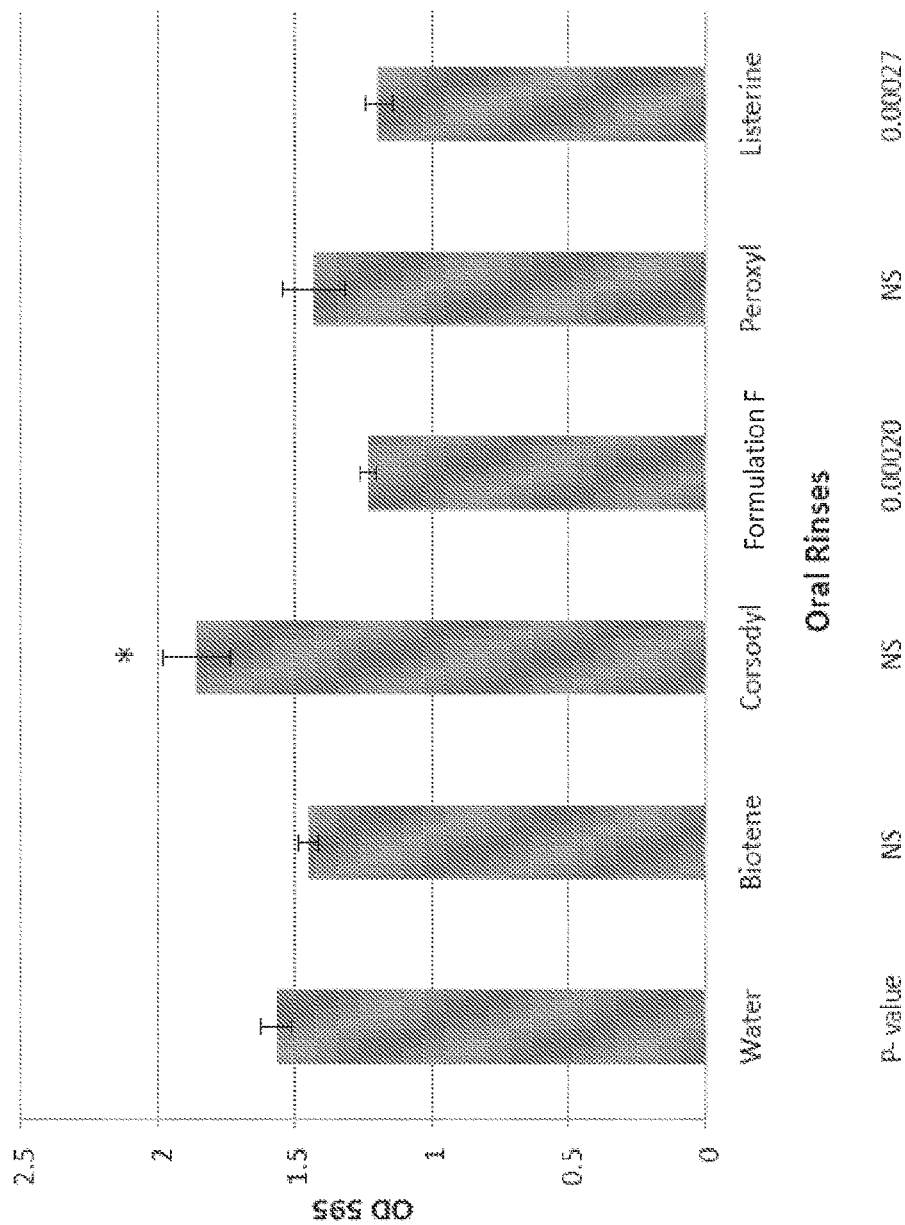
FIG. 11. Exemplary MBEC peg biofilm reduction assay of PAAG-based oral rinse compared to other products (twice daily treatment).

Results:

FIG. 10 show that PAAG Formulations F ($p=0.0002$) and H ($p=0.0009$) significantly reduced *S. mutans* biofilms after 1-hour treatment, similar to and more effective than Listerine ($p=0.0012$). FIG. 11 show that biofilms treated twice in one day with oral rinse for 2 minutes each treatment with an 8 hour interval in between, have similar biofilm reduction to those treated for just 1-hour. PAAG oral rinse Formulation F significantly ($p=0.0002$) reduced *S. mutans* biofilm compared to control, as did treatment with Listerine ($p=0.0003$). Other oral rinse treatments tested that did not significantly reduce *S. mutans* biofilm biomass included Biotene, Corsodyl and Peroxyl, which list lactoferrin, chlorhexidine, and hydrogen peroxide as active ingredients, respectively.

Example 11: Comparative Oral Formulation Biofilm Viability Reducing Activity Protocol:

Antibacterial tests evaluated components of oral rinse in vitro for the ability to kill *S. mutans*. *S. mutans* was grown in Todd Hewitt broth overnight at 37° C. and resuspended in PAAG Oral Formulation F (PAAG 37 kDa, 23% functionalized), Formulation H (PAAG 86 kDa, 30% functionalized), or other oral rinse products at a concentration of about $10^6$ CFU/ml. The bacteria were treated with each oral rinse formulation twice in one day for 2 minutes each treatment with an 8-hour interval in between, then resuspended in PBS, vortexed and sonicated for 10 minutes to break up aggregated bacteria. Aliquots were serially diluted and plated onto BHI agar to quantify growth via viable plate counts.

Figure 12:
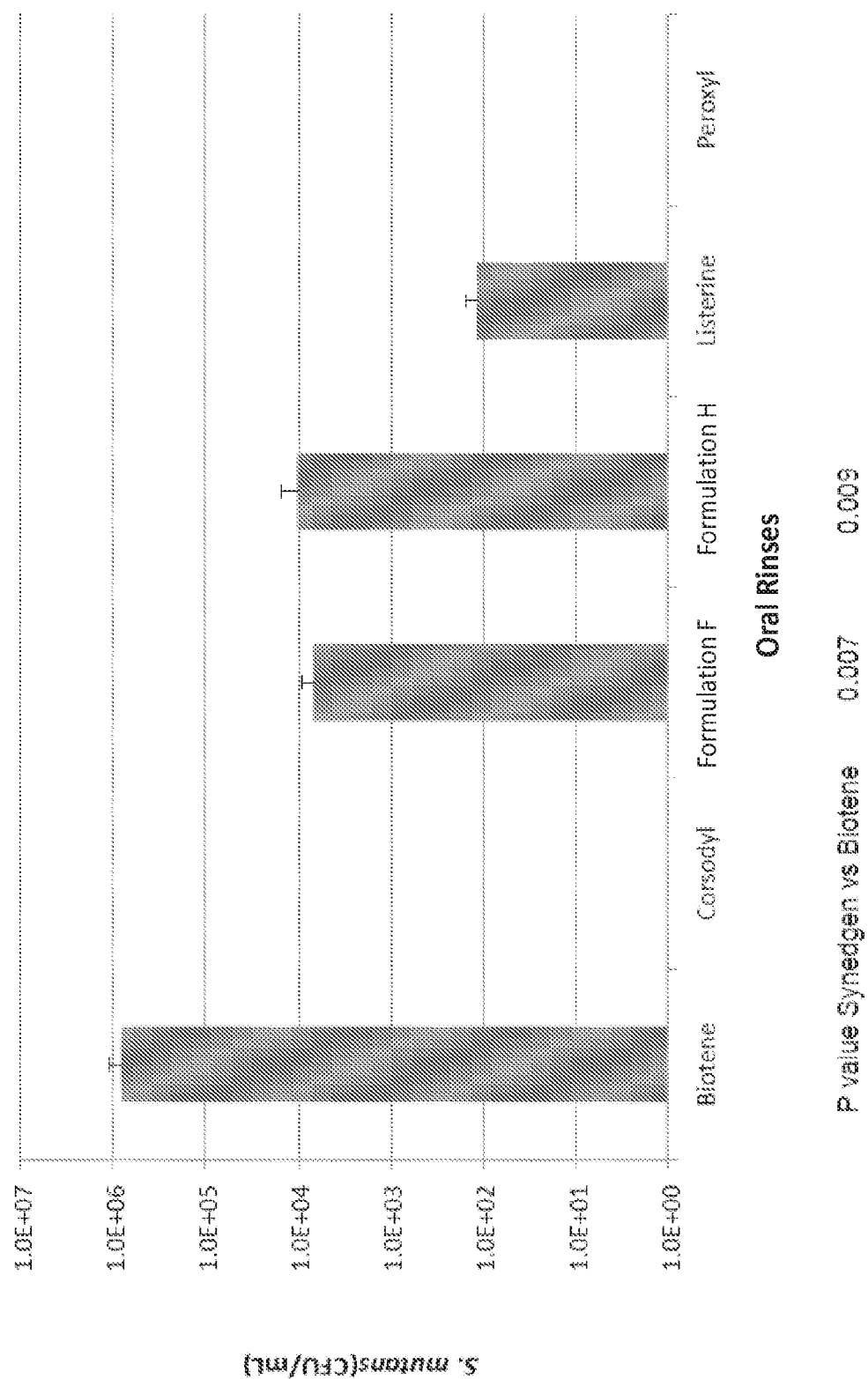
FIG. 12. Exemplary MBEC peg biofilm viability reduction assays of PAAG-based and other oral rinse products (twice daily treatment).

Results:

Formulations F (PAAG 37 kDa, 23% functionalized) and H (PAAG 86 kDa, 30% functionalized) contain the complete oral rinse formulation ingredients: 17.5% sorbitol, 10% glycerin, 1.5% Polysorbate 20, 0.2% Peppermint oil, 2.5% xylitol, 0.3% benzoic acid, 0.05% sodium fluoride, 0.0032% PAAG. In FIG. 12, PAAG Formulations F ($p=0.007$) and H ($p=0.009$) show significant antibacterial reductions of *S. mutans* biofilms after treatment compared to Biotene. Note that the strong antiseptics (Corsodyl, Listerine, and Peroxyl) are more effective at killing bacteria than the PAAG oral rinse but were found less effective at reducing biofilm biomass.

Example 12: Antibacterial Activity of Oral Rinses Against Bacteria that Cause Halitosis Protocol:

Antibacterial tests evaluated PAAG in vitro for their ability to kill *S. warneri*. The halitosis-specific bacteria *S. warneri* was grown in Todd Hewitt broth overnight at 37° C. and resuspended in water at a concentration of about $10^6$ CFU/ml. The bacteria were treated with each oral rinse formulation for 15 minutes, then resuspended in PBS, vortexed and sonicated for 10 minutes to break up aggregated bacteria. Aliquots were serially diluted and plated onto BHI agar to quantify growth via viable plate counts.

Figure 13:
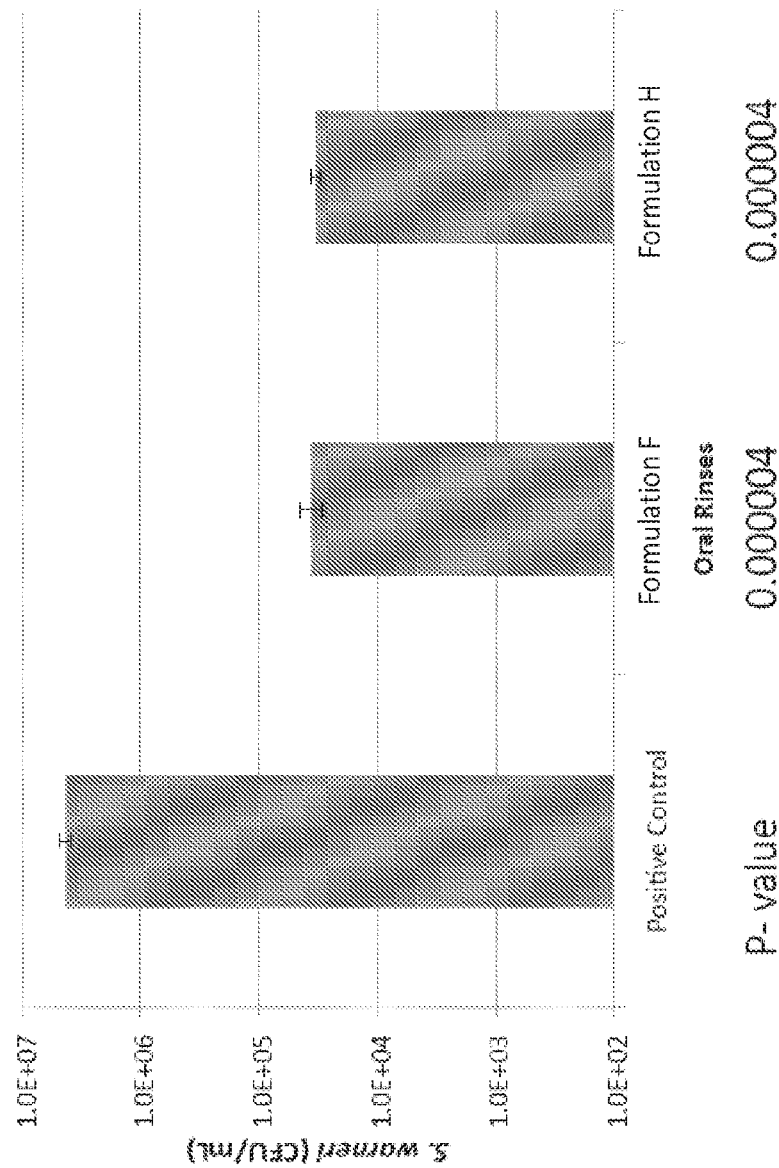
FIG. 13. Exemplary antibacterial activity of PAAG oral rinse against Staphylococcus warneri, bacteria that cause halitosis.

Results:

Formulations F (PAAG 37 kDa, 23% functionalized) and H (PAAG 86 kDa, 30% functionalized) contain the complete oral rinse formulation ingredients: 17.5% sorbitol, 10% glycerin, 1.5% Polysorbate 20, 0.2% Peppermint oil, 2.5% xylitol, 0.3% benzoic acid, 0.05% sodium fluoride, 0.0032% PAAG. As shown on FIG. 13, both Formulations F (p=3.80E-06) and H (p=3.77E-06) show significant antibacterial reductions of *S. warneri* as compared with the untreated control.

Example 13: Synergistic Combination of PAAG and Xylitol in Planktonic *Streptococcus mutans*

Protocol:

Xylitol was tested with PAAG (29% functionalized, 21 kDa) against planktonic *Streptococcus mutans* by a 1-hour treatment followed by plating and viable CFU enumeration. Increasing concentrations (50 mg/mL, 100 mg/mL, and 150 mg/mL) of xylitol were tested with PAAG at 16, 8, 4, and 2 µg/mL. A 2-log or greater reduction from the more active agent was defined as synergistic. Anything under a 2-log reduction but over a 1-log reduction was considered additive.

Results:

The results of these exemplary experiments are shown on TABLE 3, and suggest that the lower concentrations of PAAG and higher concentration of xylitol were synergistic (highlighted cells). Concentrations of xylitol and PAAG were then selected based on these experiments.

Example 14: Synergistic Combination of PAAG and Xylitol in Oral Biofilm of *Streptococcus mutans*

Protocol:

This experiment examined if the same synergistic effect (observed and described in Example 14) could be seen in oral biofilm of *S. mutans*. Planktonic bacteria often have lower inhibition concentrations than sessile bacteria; therefore higher concentrations of PAAG and xylitol were selected. An oral biofilm of *S. mutans* was grown on hydroxyapatite-coated pegs according to the minimum biofilm eradication concentration (MBEC) assay for 72 hours, and then the hydroxyapatite plate was treated with several concentrations of PAAG (29% functionalized, 21 kDa) and xylitol for 4 hours. Bacteria were treated with water as a positive control. After the 4-hour treatment, the hydroxyapatite pegs were sterilely removed from the plates, placed in 1.5 mL centrifuge tubes filled with 200 µL of sterile water, and sonicated for 10 minutes. 200 µl were then removed, diluted, and plated for CFU enumeration. Anything greater than a 2-log reduction from the more active agent was defined as synergistic.

Figure 14:
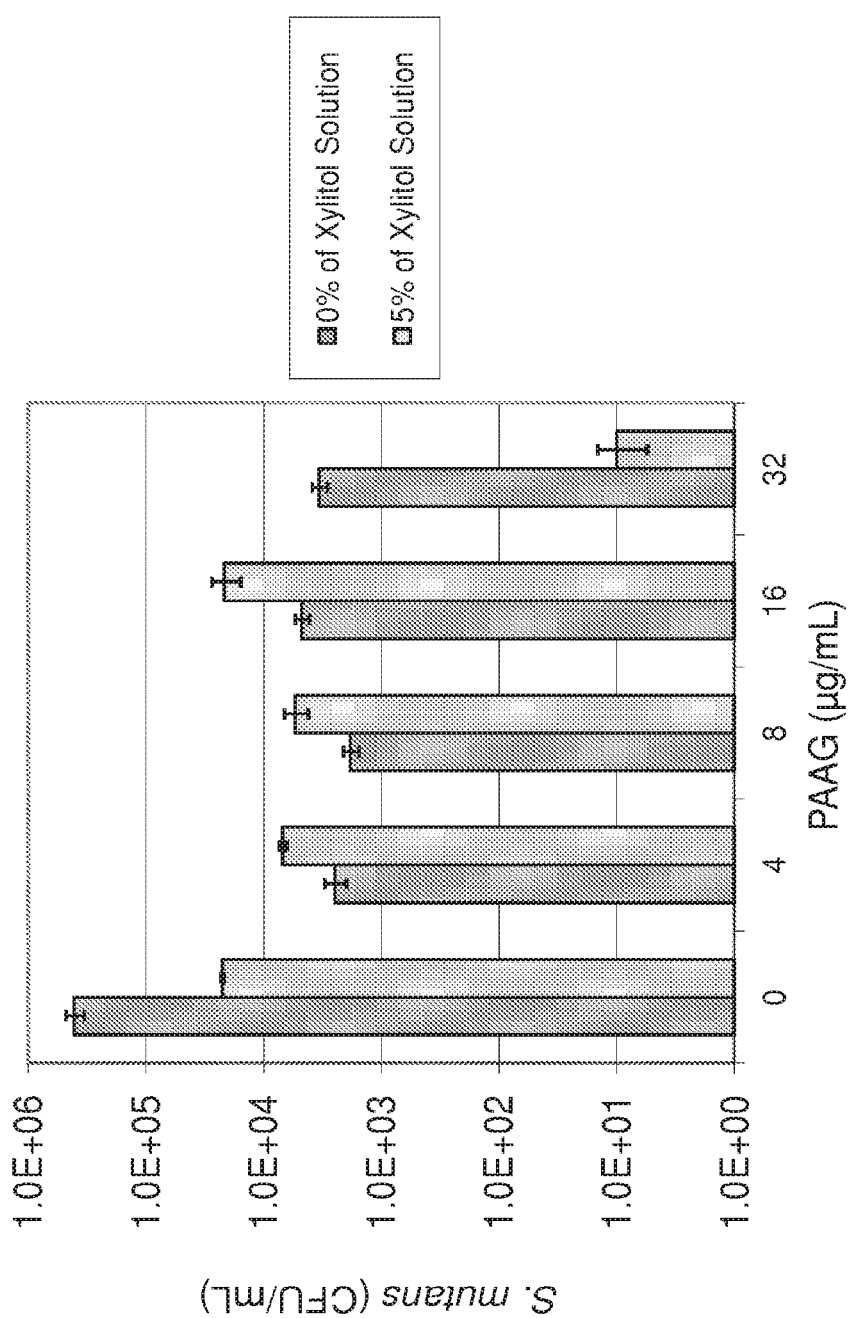
FIG. 14. Exemplary bactericidal activity of combinations of PAAG and xylitol demonstrating synergy.
Figure 15:
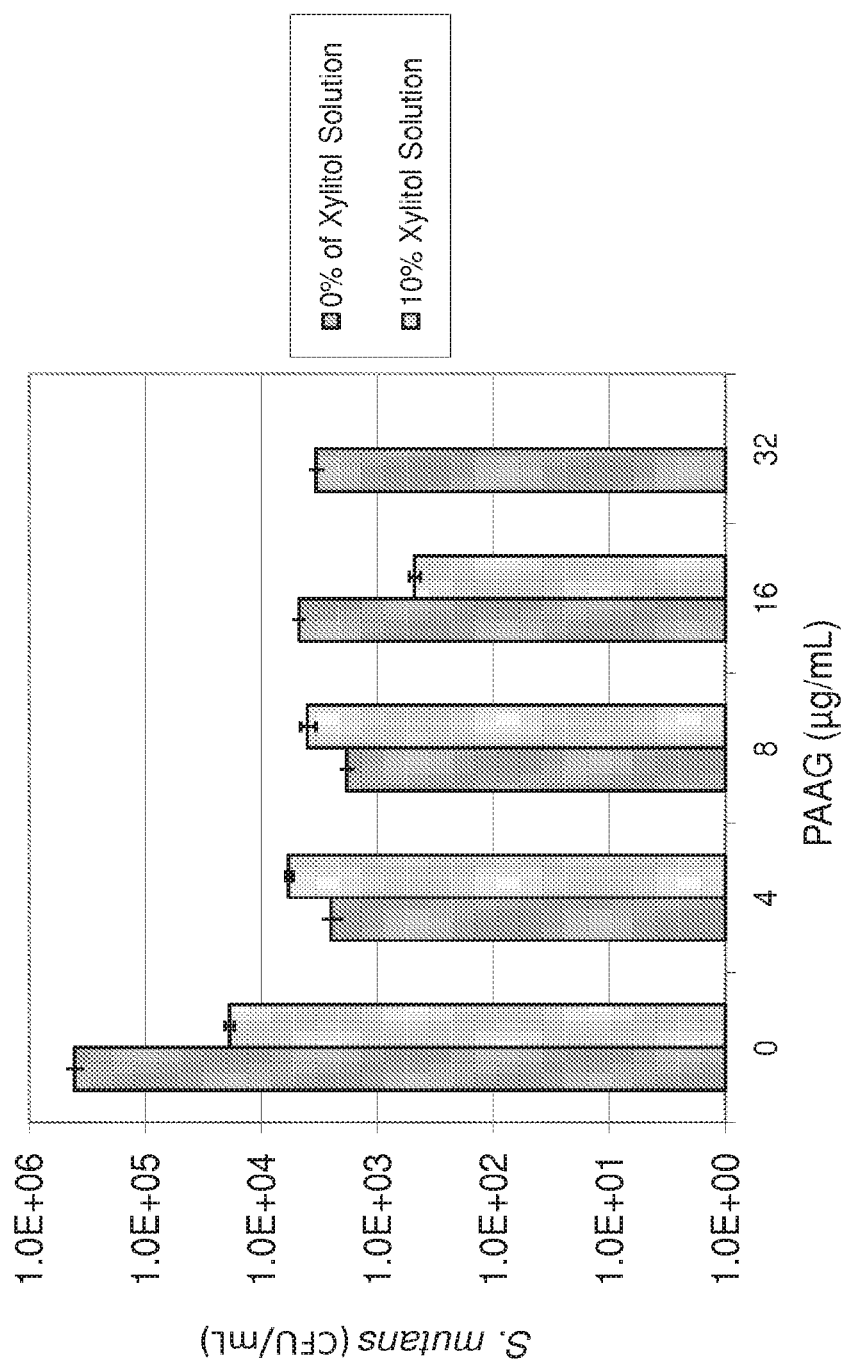
FIG. 15. Exemplary bactericidal activity of combinations of PAAG and xylitol demonstrating synergy.

Results:

PAAG at 32, 16, 8, and 4 µg/mL with xylitol at 20%, 10%, and 5% were tested. The results of these exemplary experiments are shown on FIG. 14 and FIG. 15. A reduction greater than 2-logs was seen at 32 µg/mL with xylitol at both 5% and 10%, suggesting synergistic effects at these concentrations. TABLE 4 presents the quantitative synergistic measurement for PAAG at 32 µg/mL.

Example 15: Synergistic Combination of PAAG and Sorbitol in Oral Biofilm of *Streptococcus mutans*

Protocol:

A range of sorbitol concentrations (0-25% w/v) was mixed with a range of PAAG concentrations (4-32 µg/mL, 86 kDa, 30% functionalized). *S. mutans* was exposed to each for 30 minutes before being neutralized with D/E neutralization broth, then diluted and plated for measurement of viable plate counts (CFU). Synergy in bactericidal assay was defined as a greater than 2-log reduction as observed beyond the most active agent.

Figure 16:
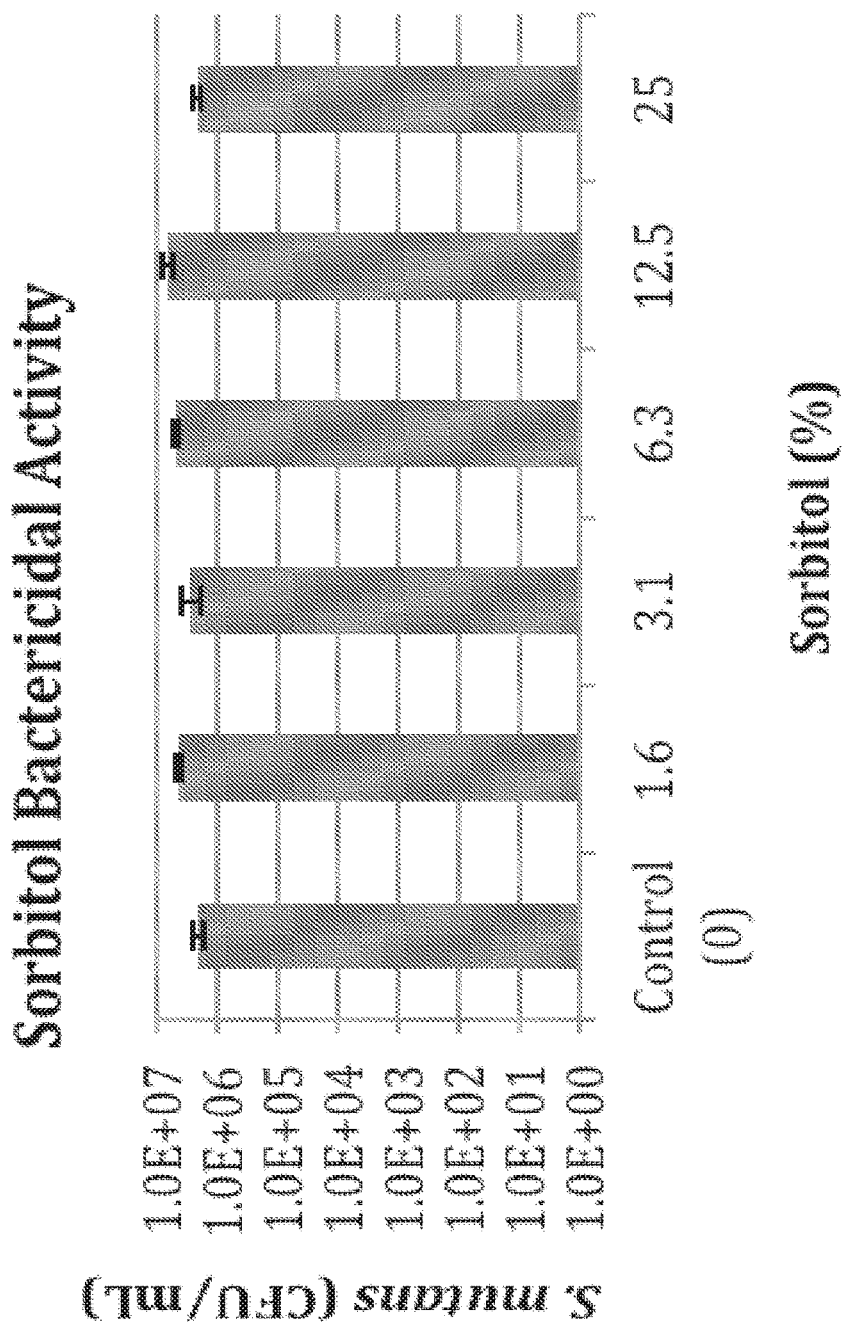
FIG. 16. An exemplary study shows that sorbitol has no effect on viability of S. mutans after 30 minute treatment.
Figure 17:
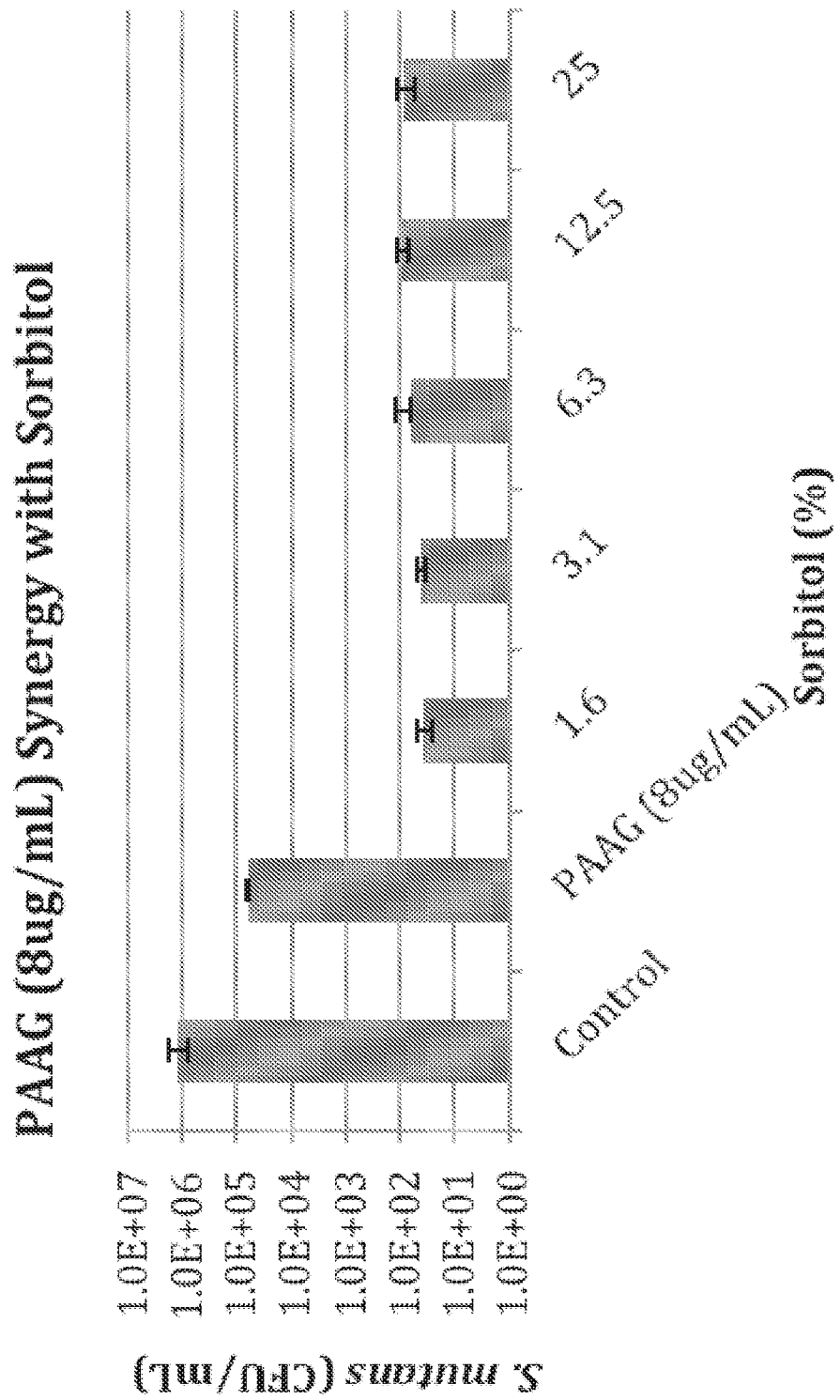
FIG. 17. PAAG (8 μg/mL) bactericidal activity demonstrates synergy with increasing sorbitol concentrations.

Results:

In these exemplary studies the sorbitol concentration did not affect bacterial viability (FIG. 16). PAAG was the most active agent in each study. The 8 µg/mL PAAG treatment reduced *S. mutans* viability in 30 minutes by approximately 1-log to $10^5$ CFU/mL (FIG. 17). The addition of sorbitol at all concentrations tested showed greater than a 2-log reduction in *S. mutans* CFU/mL beyond 8 µg/mL PAAG treatment alone, suggesting that the presence of sorbitol facilitates synergistic antibacterial activity.

Figure 18:
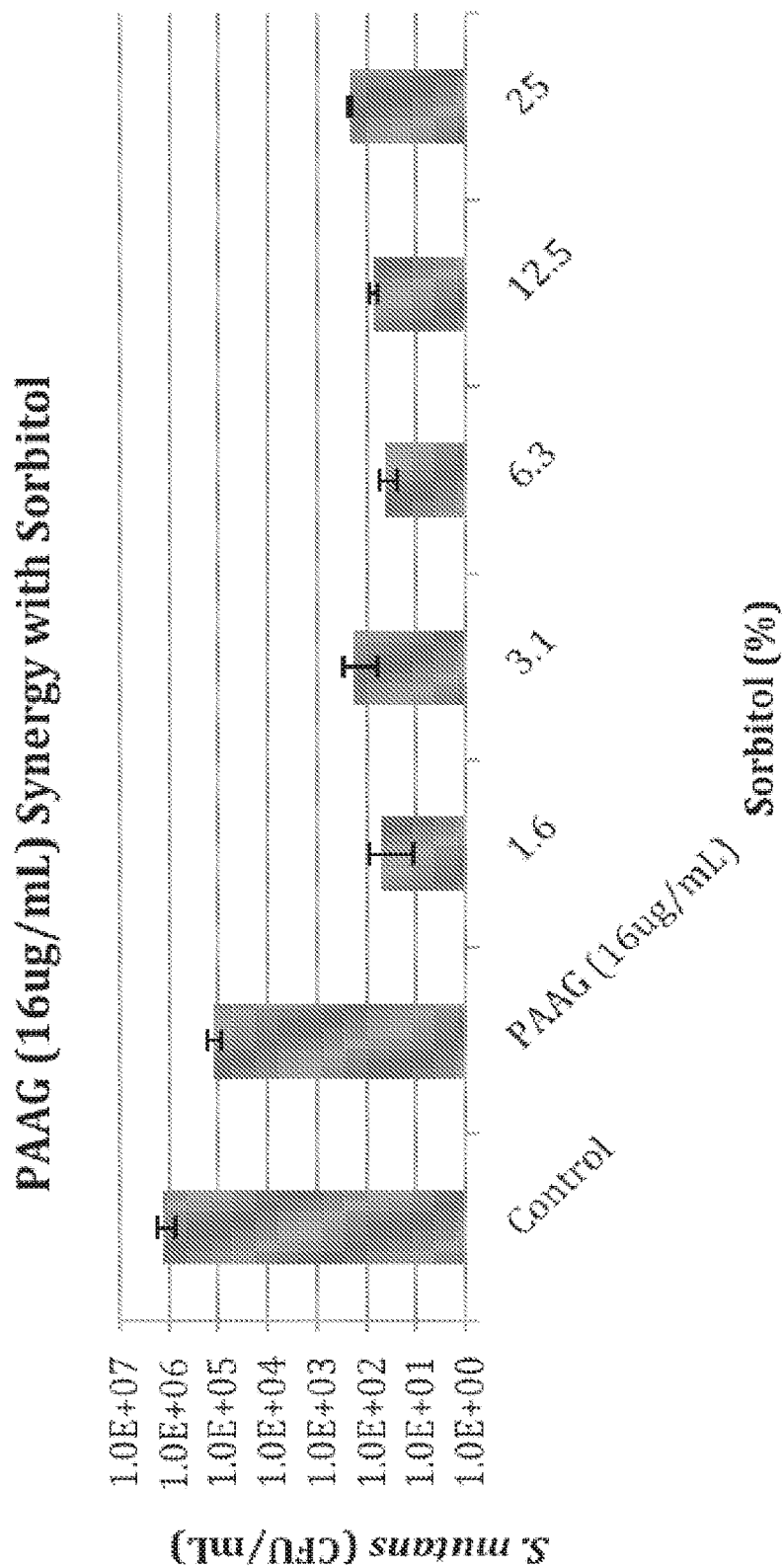
FIG. 18. PAAG (16 μg/mL) bactericidal activity against S. mutans demonstrates synergy with increasing sorbitol concentrations.

A 16 µg/mL PAAG treatment with reduced *S. mutans* viability in 30 minutes by approximately 1-log to $10^5$ CFU/mL (FIG. 18). The addition of sorbitol at all concentrations tested showed a greater than 2-log reduction in *S. mutans* CFU/mL beyond 16 µg/mL PAAG treatment alone, suggesting that the presence of sorbitol facilitates synergistic antibacterial activity.

Figure 19:
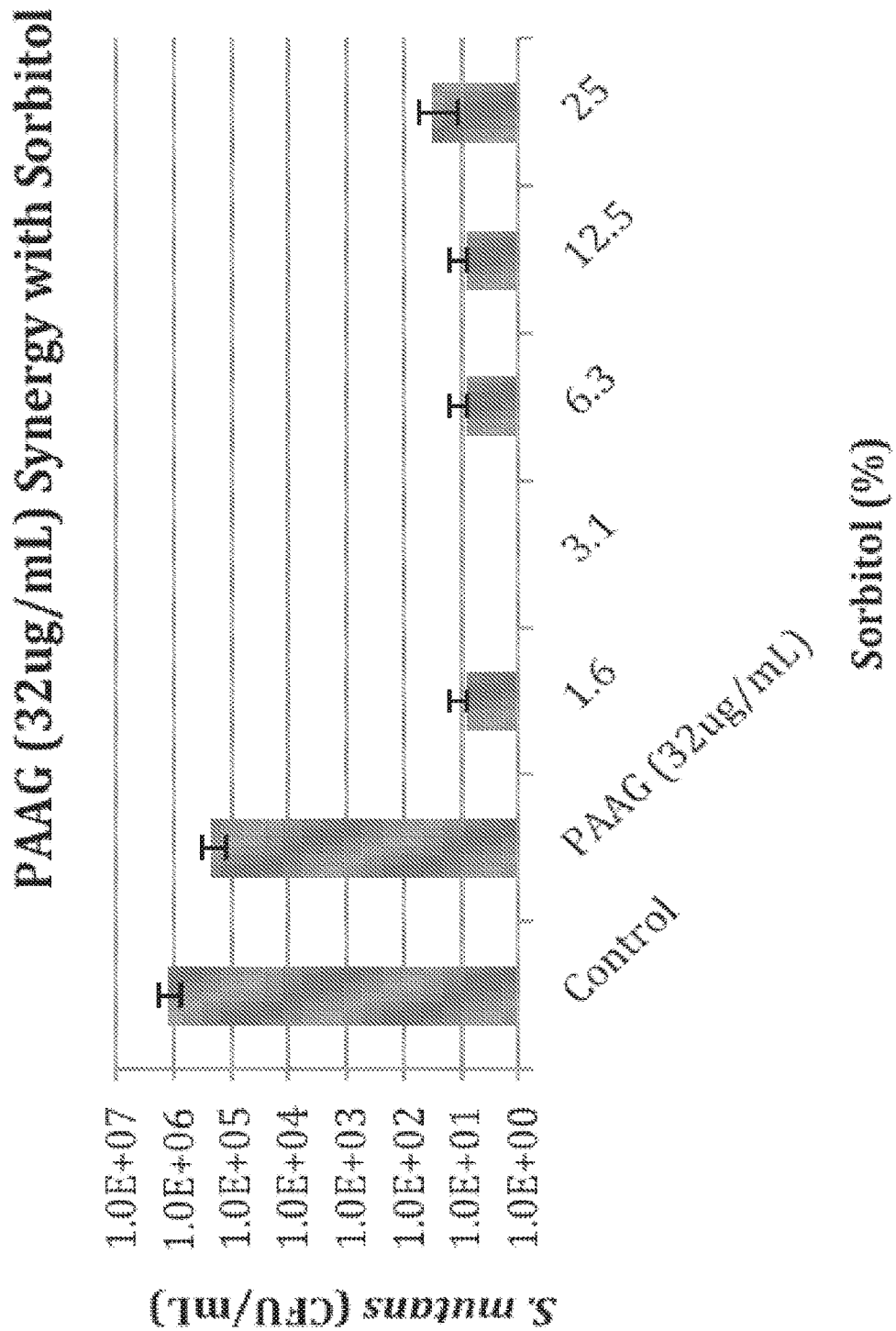
FIG. 19. PAAG (32 μg/mL) bactericidal activity against S. mutans demonstrates synergy with increasing sorbitol concentrations.

A 32 µg/mL PAAG treatment with reduced *S. mutans* viability in 30 minutes by approximately 0.5-log to $5\times10^5$ CFU/mL (FIG. 19). The addition of sorbitol at all concentrations tested showed a greater than 2-log reduction in *S. mutans* CFU/mL beyond 32 ug/mL PAAG treatment alone, suggesting that the presence of sorbitol facilitates synergistic antibacterial activity.

Figure 20:
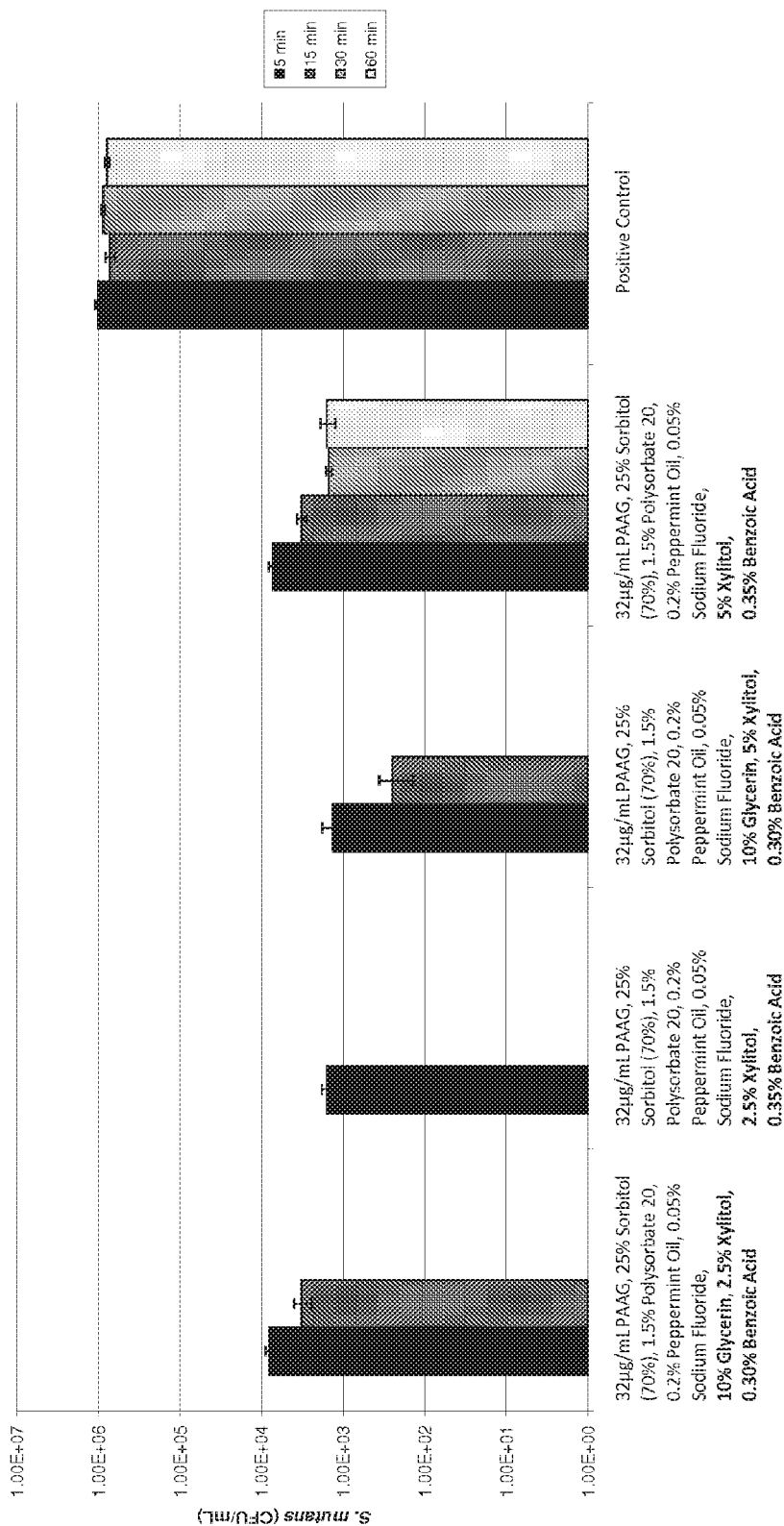
FIG. 20. Optimization studies of antibacterial activity and mouth feel and taste.

Example 16: Optimization of Oral Rinse Formulation for Antibacterial Activity, Taste, and Mouth Feel Summary:

Development of the oral rinse formulation required balancing the antibacterial activity, taste, and mouth feel to satisfy specific requirements determined by distributors based on current market information. To this end, the use of glycerol, sorbitol, xylitol, peppermint oil and benzoic acid were balanced with PAAG to maintain and optimize antibacterial activity and specific mouth feel and taste. Specifically, this study examined the impact of 10% glycerol in the formulation with either 2.5% or 5% xylitol. The formulation containing 5% xylitol without glycerol was less antibacterial, and the other formulations had an undesirable taste. Benzoic acid was also slightly modified (0.3-0.35%) in an attempt to increase possible synergistic antibacterial activity while maintaining acceptable formulation taste. The sugars' ability to mask the taste of polysorbate 20 and benzoic acid, while maintaining strong antibacterial activity was best accomplished by the 32 µg/mL PAAG (86 kDa, 30% functionalized), 17.5% Sorbitol, 1.5% Polysorbate 20, 0.2% Peppermint Oil, 0.05% Sodium Fluoride, 10% Glycerin, 2.5% Xylitol, 0.30% Benzoic Acid formulation. FIG. 20 presents the formulations tested in this optimization study.

Example 17. Flow Cell Assay for Determining Change in Oral Biofilm Biomass

Protocol:

A flow cell chamber (Biosurface Technologies) consisted of two channels recessed to accept 3 polycarbonate coupons. *S. mutans* ATCC 35668, *S. warneri* ATCC 49454 were grown overnight in BHI media at 37° C. under anaerobic conditions and transferred to 25 mL BHI to achieve a 1 McFarland standard suspension in a 1:1 ratio. As adapted from Rutegren (Rutegren et. al., 1992), each flow cell channel was primed with approximately 10 mL of the bacterial suspension. An IsmaTec Low Flow, High Accuracy Multichannel Peristaltic Pump (IBI Scientific) facilitated an initial 1-hour attachment phase, at a flow rate of 1.5 mL/min. Following the attachment phase, the polycarbonate coupons were rinsed with BHI media supplemented with 1% sucrose, then continuously pumped in at a flow rate of 0.24 mL/min for at least 6 hours. The polycarbonate coupons were rinsed for 2 minutes at approximately 15 mL/min with either water or PAAG Oral Rinse Formulation H (as described on TABLE 2) at 200 µg/mL or 32 µg/mL PAAG (86 kDa, 30% functionalized) concentration, then media pumping was resumed overnight. Rinses were repeated at 22 and 26 hours post-attachment. The polycarbonate coupons were then removed and rinsed. Excess water was drained from the coupons, then dried in a humid chamber 37° C. for 10 minutes. The coupons were then removed, and wet weight was recorded. Each coupon was sonicated in a glass vial containing 5 mL sterile water with an ultrasonic liquid processor (Misonix XL-2000) for 30 seconds to remove less cohesive biofilm material, then the wet weight was recorded again. A final sonication for 10 minutes removed the total adherent bacteria. Serial dilutions enumerated viable CFU in triplicate. Fold change was calculated using the net difference over each respective control value. Significance for statistical difference was calculated by using a ratio paired Student's t-test. Pairing of student's t-test was done by matching control and treated values based off of their corresponding coupon location.

Results:

In these exemplary experiments, mixed oral bacterial populations (S. mutans and S. warneri) were used to initiate biofilm growth to examine biofilm cohesion in a flow cell model. This experiment examined the ability of PAAG to reduce the cohesion of mixed biofilms. The PAAG oral rinse formulation was tested at two concentrations (32 µg/mL and 200 µg/mL formulation), and worked equally well. The fold change in S. mutans and S. warneri oral biofilm biomass following a twice-daily treatment with PAAG Oral Rinse Formulation H compared to control (N=2) was calculated using the net difference over each respective control value. Significance for statistical difference was calculated by using a ratio paired Student's t-test. Pairing of student's t-test was done by matching control and treated values based off their corresponding coupon location. Cumulative data from three independent experiments (**p value≤0.01) showed that significant reduction in the fold change in biomass of PAAG treated versus control (p≤0.004) was observed with both PAAG oral rinse treatments.

TABLE 1

| Treatment | Percent (%) Biomass Reduced |
|---|---|
| 20% Alcohol | 39.9 ± 3.9 |
| 1.5% $H_2O_2$ | 36.9 ± 3.8 |
| 0.0032% PAAG | 27.7 ± 2.8 |
| 0.2% Lactoferrin | 25.6 ± 4.3 |
| 0.2% Chlorhexidine | 17.1 ± 4.5 |
| Listerine | 41.7 ± 3.7 |
| Peroxyl | 32.4 ± 4.7 |
| Formulation H | 32.3 ± 3.4 |
| Biotène | 29.3 ± 3.4 |

TABLE 2

| Formulation | A | B | C | D | E | F | G | H* |
|---|---|---|---|---|---|---|---|---|
| Sorbitol | 0 | 0 | 0 | 25% | 25% | 25% | 25% | 25% |
| Xylitol | 15% | 10% | 10% | 0 | 0 | 2.5% | 2.5% | 2.5% |
| Glycerin | 0 | 0 | 0 | 0 | 0 | 10% | 0 | 10% |
| PAAG | 32 µg/ml | 32 µg/ml | 32 µg/ml | 32 µg/ml | 32 µg/ml | 32 µg/ml | 32 µg/ml | 32 µg/ml |
| Polysorbate 20 | 1.5% | 1% | 0.5% | 1% | 0.5% | 1.5% | 1.5% | 1.5% |
| Peppermint Oil | 1.5% | 1% | 0.5% | 1% | 0.5% | 0.2% | 0.2% | 0.2% |
| Sodium Bicarbonate | 0.1% | 0 | 0 | 0 | 0 | 0 | 0 | 0 |
| Benzoic Acid | 0 | 0 | 0 | 0 | 0 | 0.3% | 0.35% | 0.3% |
| Sodium Fluoride | 0 | 0.1% | 0 | 0.1% | 0 | 0.05% | 0.05% | 0.05% |

Formulations A-G: PAAG: 23% functionalized, 37 kDa.
*Formulation H PAAG: 30% functionalized and 86 kDa.

TABLE 3

| | 5% Xylitol | 10% Xylitol | 15% Xylitol |
|---|---|---|---|
| 16 µg/mL PAAG | 3.2 | 3.9 | 5.9 |
| 8 µg/mL PAAG | 1.1 | 3.1 | 4.4 |
| 4 µg/mL PAAG | 1.5 | 2.0 | 2.5 |
| 2 µg/mL PAAG | 1.2 | 1.5 | 1.5 |

TABLE 4

| | 5% Xylitol | 10% Xylitol |
|---|---|---|
| 31 mg/mL PAAG | 2.2 | 3.5 |

The invention claimed is:

1. A method of treating dry mouth, the method comprising administering to a subject an oral care aqueous composition comprising:

sorbitol present in the composition at an amount from about 5% to about 35% by weight of the composition;

xylitol present in the composition at an amount from about 2% to about 15% by weight of the composition; and a poly (acetyl, arginyl) glucosamine (PAAG), wherein PAAG comprises the following formula (I):

formula (I)

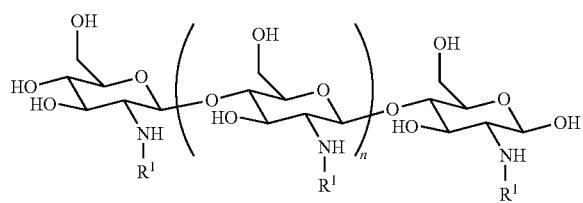

wherein:
n is an integer between 20 and 6000; and
each $R^1$ is independently selected for each occurrence from hydrogen, acetyl,

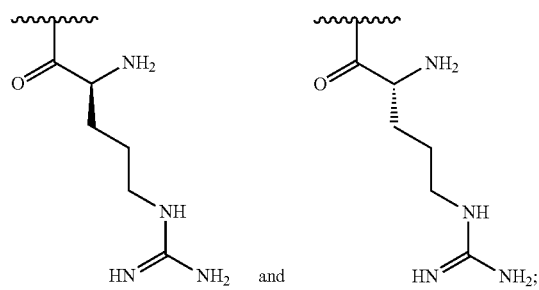 [SMILES: *C(=O)[C@@H](N)CCCNC(=N)N ; *C(=O)[C@H](N)CCCNC(=N)N]

wherein at least 25% of $R^1$ substituents are H, at least 1% of $R^1$ substituents are acetyl, and at least 2% of $R^1$ substituents are

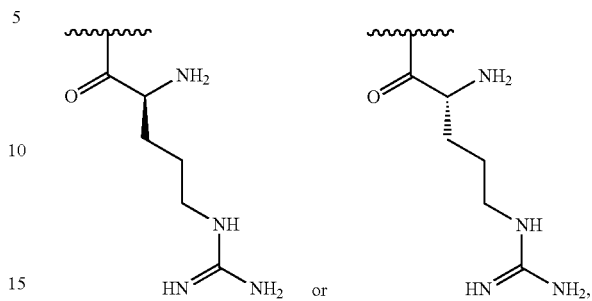

the molecular weight of the PAAG is from 20 to 200 kDa, and wherein the PAAG is present in the composition at an amount of at least 0.003% to about 0.05% w/v of the composition.

2. The method of claim 1, wherein the composition further comprises:
   glycerin; and
   a flavoring agent.

3. The method of claim 1, wherein the PAAG is functionalized at from about 5% to about 50%.

4. The method of claim 1, wherein the pH is from about 6 to about 8.

* * * * *